(12) United States Patent
Geser et al.

(10) Patent No.: US 7,823,584 B2
(45) Date of Patent: Nov. 2, 2010

(54) ATOMIZER

(75) Inventors: Johannes Geser, Ingelheim am Rhein (DE); Burkhard P. Metzger, Ingelheim am Rhein (DE); Christian Goldberg, Gelsenkirchen (DE); Michael Schyra, Wuppertal (DE); Ralf Thoemmes, Willich (DE); Birgit Westmeier, Dortmund (DE); Guido Schmiedel, Dortmund (DE); Hubert Kunze, Dortmund (DE); Georg Boeck, Laupheim (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 1023 days.

(21) Appl. No.: 11/466,941

(22) Filed: Aug. 24, 2006

(65) Prior Publication Data

US 2007/0062518 A1     Mar. 22, 2007

(30) Foreign Application Priority Data

Aug. 24, 2005    (DE) ................... 10 2005 039 921

(51) Int. Cl.
| | | |
|---|---|---|
| B05B 3/02 | (2006.01) | |
| B05B 7/30 | (2006.01) | |
| B05B 1/32 | (2006.01) | |
| A61M 11/00 | (2006.01) | |
| A61M 5/30 | (2006.01) | |
| B67D 7/22 | (2010.01) | |
| B67D 7/84 | (2010.01) | |
| B67D 7/08 | (2010.01) | |
| B67B 1/00 | (2006.01) | |

(52) U.S. Cl. .................... 128/200.17; 128/200.14; 222/36; 222/38; 222/162; 222/153.11; 222/153.13; 239/71; 239/318; 239/538; 604/70; 604/71

(58) Field of Classification Search ............ 128/200.14, 128/200.21, 200.22, 200.23, 203.12–203.15, 128/203.19, 203.21, 203.23, 203.24; 222/36–38, 222/162, 153.11, 153.13; 239/71, 321–322, 239/318, 537–541, 589; 604/68–72
See application file for complete search history.

(56) References Cited

U.S. PATENT DOCUMENTS

| 4,565,302 A | * | 1/1986 | Pfeiffer et al. ............... 222/38 |
| 4,817,822 A | | 4/1989 | Rand et al. |
| 5,277,334 A | | 1/1994 | Malinconico |
| 5,482,030 A | | 1/1996 | Klein |

(Continued)

FOREIGN PATENT DOCUMENTS

DE    100 61 723 C2    7/2002

(Continued)

Primary Examiner—Justine R Yu
Assistant Examiner—Rachel T Young
(74) Attorney, Agent, or Firm—Roberts Mlotkowski Safran & Cole, P.C.; David S. Safran

(57) ABSTRACT

An atomizer for a fluid, in particular, a fluid for medical aerosol therapy. In order to allow simplified operation and improved safety in use, the atomizer has a counter device for counting the number of operations of the atomizer and the number of containers inserted. The atomizer is locked against further operation and/or against removal of the current container or insertion of a new container, if a certain number of operations of the atomizer and/or a certain number of containers inserted has/have been reached or exceeded.

57 Claims, 36 Drawing Sheets

U.S. PATENT DOCUMENTS

| | | | |
|---|---|---|---|
| 5,564,414 A * | 10/1996 | Walker et al. | 128/200.23 |
| 5,740,792 A * | 4/1998 | Ashley et al. | 128/203.15 |
| 5,954,689 A * | 9/1999 | Poulsen | 604/71 |
| 5,964,416 A | 10/1999 | Jaeger et al. | |
| 6,149,054 A | 11/2000 | Cirrillo et al. | |
| 6,360,744 B1 * | 3/2002 | Myrman et al. | 128/203.15 |
| 6,510,847 B1 | 1/2003 | Helgesson et al. | |
| 6,659,307 B1 * | 12/2003 | Stradella | 222/23 |
| 7,306,116 B2 | 12/2007 | Fuchs | |
| 7,322,352 B2 * | 1/2008 | Minshull et al. | 128/203.15 |
| 2003/0100867 A1 | 5/2003 | Fuchs | |
| 2003/0188741 A1 * | 10/2003 | Scarrott et al. | 128/200.23 |
| 2004/0015126 A1 * | 1/2004 | Zierenberg et al. | 604/72 |
| 2004/0094147 A1 | 5/2004 | Schyra et al. | |
| 2004/0149772 A1 * | 8/2004 | Ouyang | 222/36 |
| 2005/0011515 A1 * | 1/2005 | Lee et al. | 128/200.23 |
| 2006/0037612 A1 * | 2/2006 | Herder et al. | 128/203.15 |
| 2006/0163276 A1 | 7/2006 | Wong et al. | |

FOREIGN PATENT DOCUMENTS

| | | |
|---|---|---|
| WO | WO 91/14468 A1 | 10/1991 |
| WO | WO 96/06011 A2 | 2/1996 |
| WO | WO 97/12687 A1 | 4/1997 |
| WO | 98/56444 A1 | 12/1998 |
| WO | 01/93932 A1 | 12/2001 |
| WO | 03/063754 A1 | 8/2003 |
| WO | WO 2005/080001 A1 | 9/2005 |
| WO | WO 2005/080002 A1 | 9/2005 |

* cited by examiner

ATOMIZER

BACKGROUND OF THE INVENTION

1. Field of the Invention

The present invention concerns an atomizer having a container with a fluid, at least one counter device for counting at least one of the operations of the atomizer and the number of containers inserted, and a housing part for at least one inserting and exchanging the container, the housing part being mounted on or detachable from the atomizer for inserting and/or exchanging the container.

2. Description of Related Art

An atomizer going by the trademark RESPIMAT® in the form of an inhaler is known, as represented by the basic principle of International Patent Application Publication WO 91/14468 A1 (corresponding to U.S. Pat. Nos. 5,497,944 and 5,662,271) and in a specific embodiment in FIGS. 6a, 6b of International Patent Application Publication WO 97/12687 A1 (corresponding to U.S. Pat. Nos. 6,726,124 and 6,918, 547) and in FIGS. 1 and 2 of the accompanying drawings of this application. The atomizer has as a reservoir for an atomizing fluid, an insertable, rigid container with an inner bag with the fluid and a pressurizer with a drive spring for feeding and atomization of the fluid.

For the purpose of completeness of the disclosure of the present patent application, reference is made as a precaution to the full disclosure content of both International Patent Application Publications WO 91/14468 A1 and WO 97/12687 A1 and their corresponding U.S. patents noted above. Generally, the disclosure there preferably relates to an atomizer with a spring pressure on the fluid of 5 to 200 MPa, preferably 10 to 100 MPa, with a fluid volume delivery for each stroke of between 10 and 50 μl, preferably between 10 and 20 μl, and most preferably approximately 15 μL. Here, the fluid is converted into an aerosol, the droplets of which have an aerodynamic diameter of up to 20 μm, preferably between 3 and 10 μm. The disclosure there further relates preferably to an atomizer with a cylinder-like form and a size of approximately 9 cm to approximately 15 cm in length and approximately 2 cm to approximately 5 cm in width and a nozzle jet fanning of between 20° and 160°, preferably between 80° and 100°. These values also apply to the atomizer according to the present invention as particularly preferred values.

Before use for the first time, the known atomizer is opened by detaching a lower housing part and a sealed container is inserted in the atomizer. Here, the container is opened by a delivery tube, which when the container is inserted, is introduced into the container as far as the inner bag. Then, the lower housing part is pushed back on.

By rotating the lower housing part of the atomizer the drive spring can be tensioned and fluid can be sucked into a pressure chamber of the pressurizer. During tensioning, the container is displaced within the atomizer with a stroke motion into the housing lower part, and when tensioned for the first time, the bottom is pierced by a piercing element in the housing lower part for aeration. Following manual operation of a locking element, the fluid in the pressure chamber is placed under pressure by the drive spring and without any propellant gas is delivered via a nozzle into a mouthpiece as an aerosol.

The empty container, following opening of the atomizer, can be exchanged for a full container and the atomizer can continue to be used.

German Patent Application DE 102 39 443 A1 and the corresponding U.S. Patent Application Publication 2004/0094147 A1 disclose a blocking device for a locking tensioning mechanism with spring-operated drive. The blocking device can be used, in particular, for a high pressure atomizer according to WO 97/12687 A1 (corresponding to U.S. Pat. Nos. 6,726,124 and 6,918,547), and after a specified number of operations, to block the further use of the atomizer in that the rotation of two housing parts of the atomizer relative to each other is prevented, in particular, through a blocking element in the form of a spring.

German Patent DE 195 49 033 C1 and the corresponding U.S. Pat. No. 6,149,054, which represent the starting point for the present invention, disclose a mechanical counter for a dosing device for the dosing of powder, liquid or gas substances. The dosing unit is used, in particular, for atomization of a medicine. The medicine is contained in a reservoir which is pushed into the dosing device. The counter is arranged in the dosing unit such that it cannot be detached. The counter allows counting of the number of doses from each reservoir and the number of reservoirs that are used with the dosing unit. A problem here is that if the counter states are not noted, faulty operations may result, such as the sucking in of air from an empty reservoir or use of more reservoirs than are permitted.

German Patent Application DE 100 61 723 A1 discloses a counter for counting dosed releases of fluid, paste or solid products and a device for the dosed release of such products. The counter works mechanically and has two counting rings which are arranged coaxially to a longitudinal axis of the counter. The counter also comprises an axially displaceable switch element, which runs across a stationary curved surface in such a way that the axial displacement is converted into a rotary movement of a counting ring. The counter can be positioned in a detachable or non-detachable manner on an aerosol container.

SUMMARY OF THE INVENTION

A primary object of the present invention is to provide an atomizer that is simple to operate and has improved safety in use.

The above object is achieved by an atomizer as described below.

An initial aspect of the present invention is that the counter device or at least a first counter of the counter device for counting the number of operations of the atomizer, is arranged on a housing part of the atomizer that can be detached in order to insert and/or change the container, wherein the atomizer is locked against further operation and/or against removal of the current container or insertion of a new container, if a certain number of operations of the atomizer has been reached or exceeded. The locking under these conditions is in the following also referred to as "first locked state." The enforced locking of the atomizer on reaching or exceeding a specified number of operations of the atomizer leads to simple operation and improved safety in use, since the user, even if not noticing an optional display of the previously performed or remaining operations of the atomizer, is protected from improper operation. In particular, it is possible to prevent sucking in air from an empty or almost empty container in an undesirable manner which can, in particular, lower the dosing accuracy.

The term "operation" of the atomizer can, with the present invention, generally include fluid withdrawal, fluid delivery, pressurization, atomization and/or tensioning of the atomizer or any other manipulation of the atomizer associated with its use.

The term "locking" or "locked," in the case of the present invention, in particular, covers both the blocking or prevention and the free running or disengagement of a drive train, of an operation, or manipulation of an operating component or the like, for example, in order to block or prevent or disable an operation, tensioning of the atomizer, changing of the container, detachment of the housing part or the like.

Of particular preference is that the container can only be mounted in the atomizer, removed from the atomizer and/or changed with the housing part and with the counter device or at least with the first counter. The inseparable connection between the container and the counter device or the first counter provides a comprehensible registration of the operations of the atomizer with the respective container. In particular, here, the counter value cannot be reset or deleted, thereby allowing later checking, for example, by the user or a third party, such as a doctor.

According to a second, also independently achievable, aspect of the present invention, the counter device is designed in such a way that the atomizer is locked against further operation and/or against removal of the current container or insertion of a new container, if a certain number of containers is used, and if necessary, also a certain number of operations of the atomizer with the current container have been reached or exceeded. The locking under these conditions is referred to in the following as the "second locked state." The stated container counting and locking leads to simple operation and improved safety in use, since use of the atomizer beyond a specified, permitted number of containers is excluded without the user having to pay attention to a display of the number of containers already used or the like.

Particular preference is in the first or second locked state for a locking element, such as a button, that is operated to trigger the delivery and/or atomization of fluid, to be locked. This makes intuitive use easier and makes it clear to the user in a simple manner that the atomizer is locked.

Alternatively or additionally, tensioning of a pressurizer or a drive spring of the atomizer in the first or second locked state can be locked. This also makes it clear to a user in a simple manner that the atomizer is locked.

Alternatively or additionally, removal of the housing part of the atomizer in the first or second locked state can be locked. This, in turn, allows intuitive identification of a locked state by a user.

According to a third, also independently achievable aspect of the present invention, the container counter device has an operating element so that the counter device can detect a movement or position of the container associated with fluid withdrawal, fluid delivery, pressurization and/or atomization and can count this as an operation of the atomizer. This leads to a particularly safe registration of operations of the atomizer, and accordingly, to safe counting. This is conducive to simple operation and improved safety in use, since faulty operation or operating errors, such as repeated operation of an operating element when the atomizer is not tensioned or without withdrawal of fluid, are not detected and counted as operations of the atomizer.

Further advantages, features, characteristics and aspects of the present invention will become apparent from the following description of preferred embodiments in conjunction with the accompany drawings.

DETAILED DESCRIPTION OF THE INVENTION

In the figures, for the same or the like parts, the same reference numbers are used, with the corresponding or comparable characteristics and advantages being arrived at even if a repeated description is dispensed with.

Figure 1:
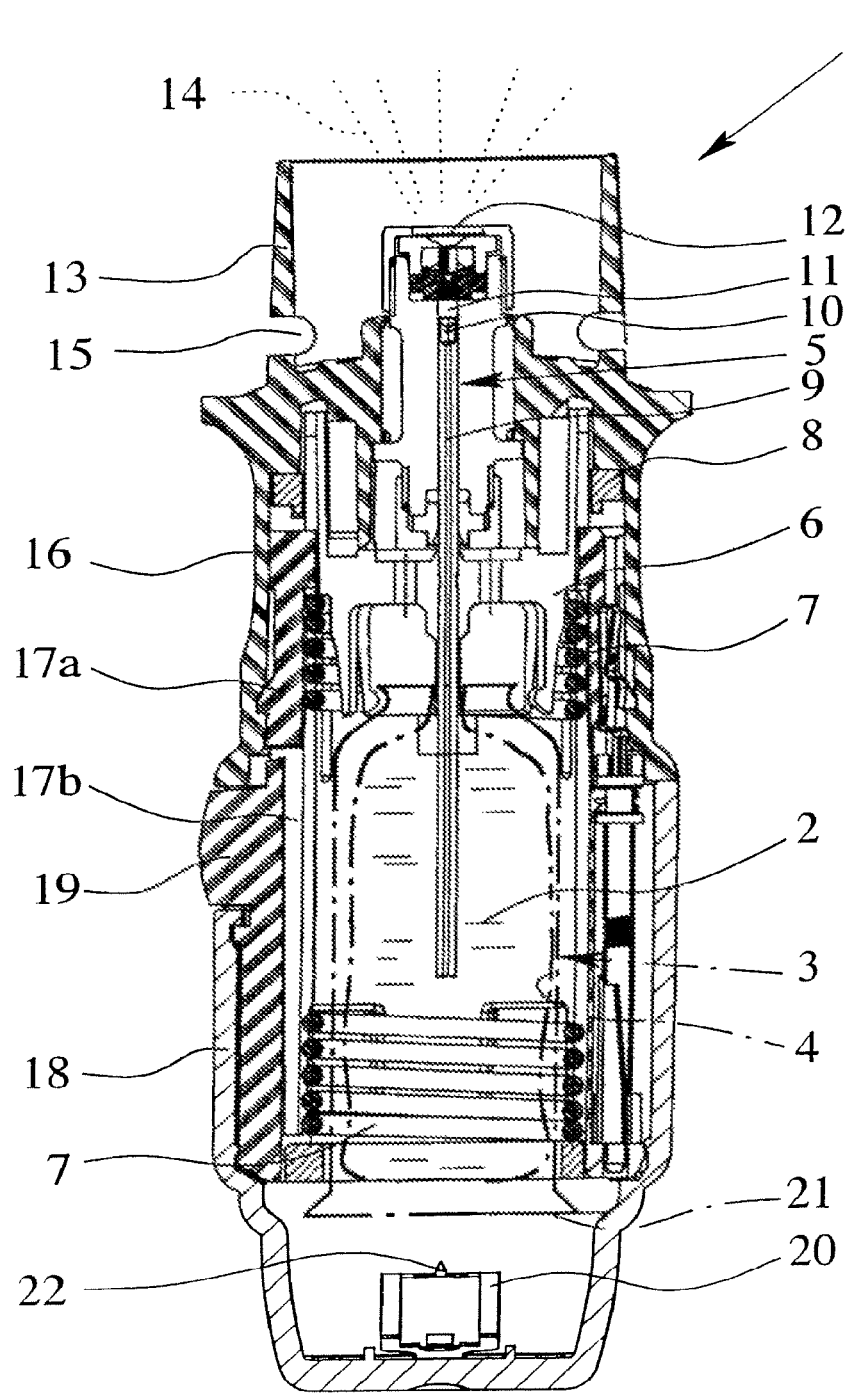
FIG. 1 is a schematic cross-section of a known atomizer in the un-tensioned state.
Figure 2:
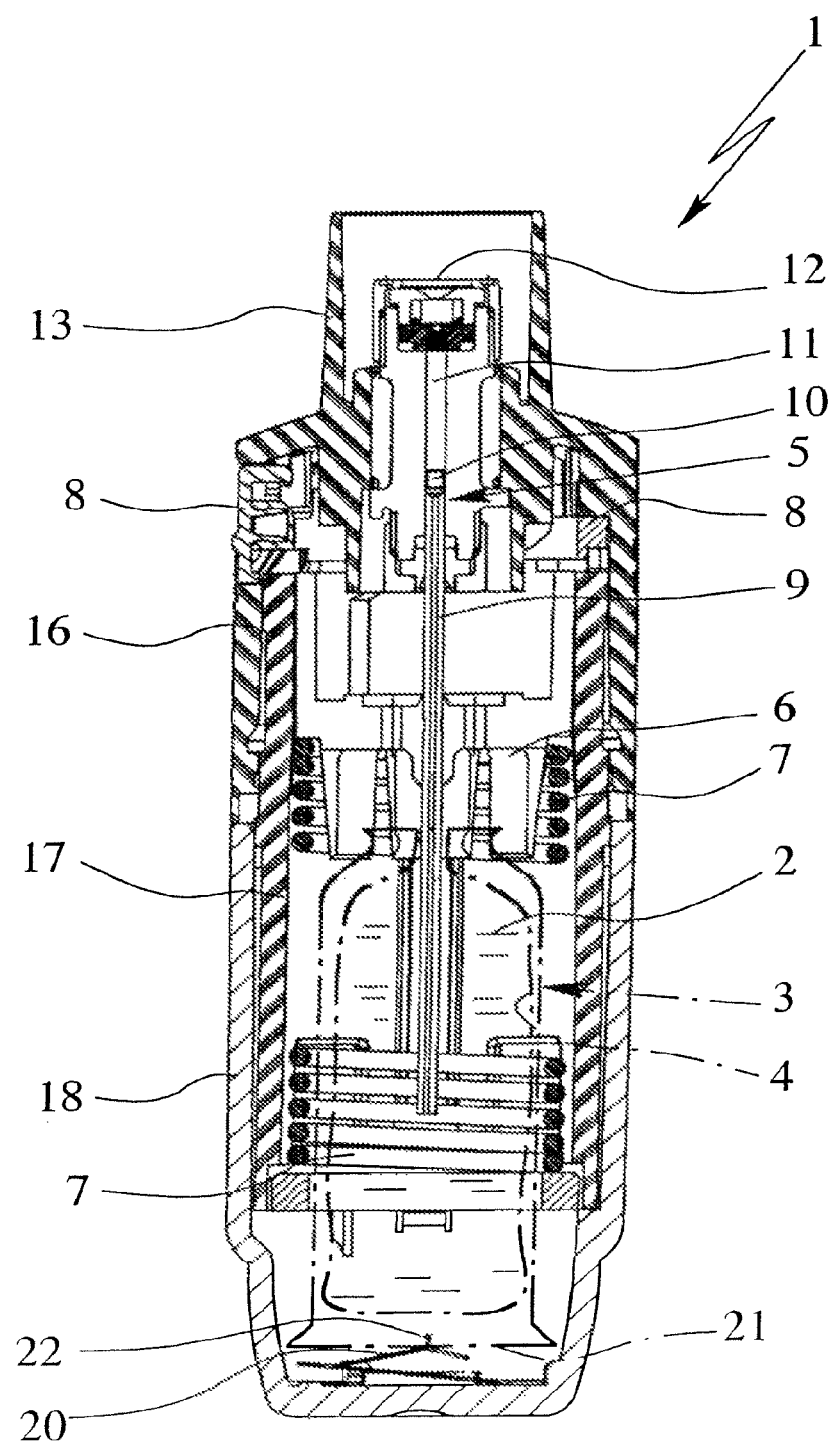
FIG. 2 is a schematic cross-section of the known atomizer in the tensioned state, rotated by 90° relative to the view in FIG. 1.

FIGS. 1 & 2 show a known atomizer 1 for atomization of a fluid 2, in particular, a highly efficacious pharmaceutical product or the like, in a schematic representation in the un-tensioned state (FIG. 1) and the tensioned state (FIG. 2). The atomizer 1 is, in particular, designed as a portable inhaler and works preferably without propellant gas.

Upon atomization of the fluid 2, preferably a liquid, in particular, a therapeutic or pharmaceutical product, an aerosol is formed which can be breathed in or inhaled by the user (not shown). Normally, inhalation takes place at least once per day, in particular, several times per day, preferably at defined time intervals, according to the illness of the user (patient).

The known atomizer 1 has an insertable and preferably exchangeable container 3 with the fluid 2. The container 3 thus forms a reservoir for the fluid 2 to be atomised. The container 3 preferably contains a sufficient quantity of fluid 2 or active substance, in order for example to provide up to 200 dosing units, therefore by way of example up to 200 atomizations or applications. A typical container 3, as disclosed in WO 96/06011 A1, holds a volume of approximately 2 to 10 ml.

The container 3 has an essentially cylindrical or cartridge-like design and, when the atomizer 1 has been opened, can be inserted in this, and if necessary, exchanged from below. Preferably, it has a rigid design, in particular, wherein the fluid 2 is held in a collapsible bag 4 in the container 3.

The atomizer 1 also has a pressurizer 5 for delivery and atomization of the fluid 2, in particular, in each case, in a defined, if necessary, adjustable dosing quantity. The pressurizer 5 has, in particular, a holder 6 for the container 3, a drive spring 7, shown only in part, that is assigned to it with a manually operated locking element 8 for unlocking, a delivery tube 9 with a non-return valve 10, a pressure chamber 11 and a discharge nozzle 12 in the vicinity of a mouthpiece 13. The container 3 is secured in the atomizer 1 via the holder 6 so that the delivery tube 9 is inserted into the container 3. The holder 6 is preferably designed in such a way that the container 3 can be exchanged.

When the drive spring 7 is axially tensioned (tensioning stroke), the holder 6 with the container 3 and the delivery tube 9 is displaced downwards (as viewed in the drawings) and fluid 2 is sucked out of the container 3 into the pressure chamber 11 of the pressurizer 5 via the non-return valve 10.

With the subsequent unlocking (atomization stroke) of the drive spring 7, following operation of the locking element 8, the fluid 2 is placed under pressure in the pressure chamber 11, in that the delivery tube 9 with its now closed non-return valve 10 is moved back upwards again by the drive spring 7 and now serves as a plunger. This pressure propels the fluid 2 through the discharge nozzle 12, by means of which it is atomized into an aerosol 14, as show in FIG. 1. The droplet size of the particles for a device of the type like the RESPIMAT® has already been described at the beginning.

A user, not shown, can inhale the aerosol 14, as a result of which air can be sucked into the mouthpiece 13 via at least one air vent 15.

The atomizer 1 has a housing upper part 16 and an inner part 17 (FIG. 2) that rotates in relation thereto with an upper part 17*a* and a lower part 17*b* (FIG. 1). On the inner part 17, a manually operating housing part 18 is secured preferably by means of a holding element 19 in a detachable fashion, in particular, by pushing it on. The housing part 18 can be detached from the atomizer 1 for insertion and/or exchanging of the container 3.

The housing part 18 can be rotated relative to the housing upper part 16, by which it takes with it the lower part 17*b* of the inner part 17. In this way, the drive spring 7 is tensioned via a gear (not shown) that operates on the holder 6 in the axial direction. With the tensioning, the container 3 is moved axially downwards until the container 3 has adopted an end position as shown in FIG. 2. In this state, the drive spring 7 is tensioned. During the atomization process (atomization stroke), the container 3 is moved back by the drive spring 7 into its starting position. The container 3 therefore performs a linear or stroke movement during the tensioning process and during the atomization process.

The housing part 18 preferably forms a cap-like housing lower part and surrounds or overlaps, if necessary, a lower free end area of the container 3. When the drive spring 7 is tensioned, the container 3 moves with its end area further into the housing part 18 or with the front end of it, wherein an axially working spring 20 arranged in the housing part 18 comes up against the container floor 21 and the container 3 or a seal in its base is pierced with a piercing element 22 during the initial contact for aeration.

The atomizer 1 has a counter device 23, which counts operations of the atomizer 1, preferably, by registering the rotations of the lousing part 18 or inner part 17 in relation to the housing upper part 16.

In the following, the design and the method of working of preferred embodiments of the atomizer are explained in more detail, with references being made to the other figures but only essential differences compared to the atomizer 1 according to FIGS. 1 & 2 being emphasized. Therefore, the statements concerning FIGS. 1 & 2 apply accordingly or in addition. Furthermore, any desired combination of characteristics of the atomizer 1 according to FIGS. 1 & 2 and the atomizer 1 according to the embodiments described in the following or between them is possible.

FIGS. 3 to 17 show a atomizer 1 according to a first embodiment of the present invention. FIG. 3 shows atomizer 1 in a schematic cross-section in the delivered state. The housing upper part 16, with the pressurizer 5 and other parts of the atomizer 1, is preferably separate from the housing part 18 with the container 3 in the delivered state.

FIG. 4 shows a schematic cross-section of the housing part 18 with the container 3 in the delivered state, wherein the opening of the housing part 18 with the container 3 is covered by a protective cap 24 that can be removed for assembly purposes. The protective cap 24 supports the container 3 which is still sealed at its free end in its delivered state, which at the time of assembly is introduced into the housing upper part 16 or inner part 17. At its base end, the container 3, in this state, is axially moved away from the piercing element 22, and thus, is sealed at the base end. Preferably, the container 3 cannot be separated from the housing part 18, but can only be exchanged with the housing part 18, in that the container 3, following initial insertion in the atomizer 1 can generally be changed or exchanged again.

Figure 5:
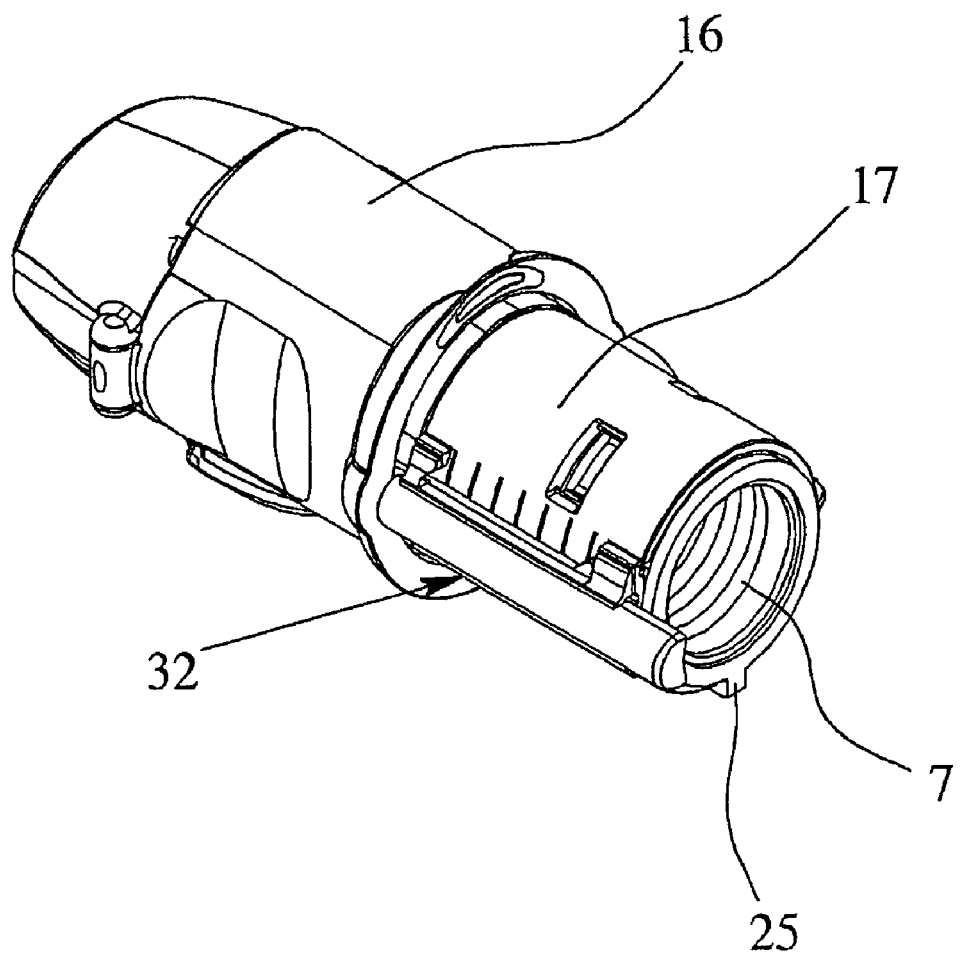
FIG. 5 is a perspective view, diagonally from below, of the housing upper part of the FIG. 3 embodiment.

FIG. 5 shows the housing upper part 16 of the atomizer 1 in the delivered state in which it is without the housing part 18 and without the container 3.

Figure 6:
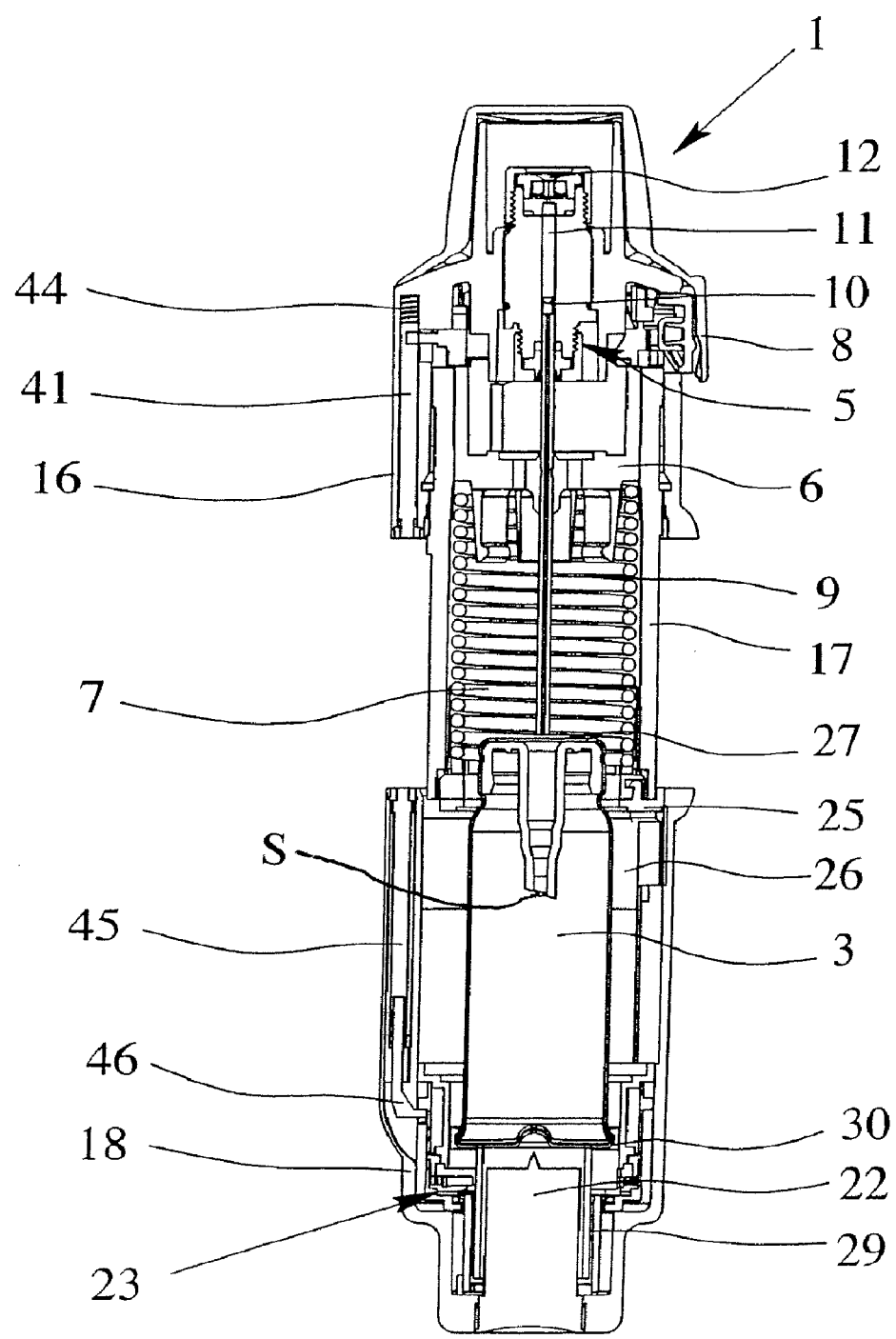
FIG. 6 is a schematic cross-sectional view of the atomizer according to FIG. 3 with the housing part partially drawn back.

To insert the container 3 into the housing upper part 16 of the atomizer 1, the housing part 18 with the container 3 is pushed onto the housing upper part 16 in the tensioned state—thus, with the tensioned pressurizer 5 or tensioned drive spring 7. FIG. 6 shows the state of the initial slide-on.

Optionally, coding is provided so that only the right or permitted housing part 18, in particular only with the permitted container 3 or the permitted fluid 2 in the container 3, can be positioned on or coupled to the housing upper part 16 in this way. For optional coding, in the example shown at the free end of the housing upper part 16, a first coding element 25 (see also FIG. 5) is arranged which, for example, forms a radial nose with a certain circumferential width and which extends radially to a certain extent. The first coding element 25 fits a complementary second coding element 26 (see, FIGS. 3 & 6), in particular, a complementary axial groove in the housing part 18, so that the housing part 18 can only be mounted on or slid onto the housing upper part 16 if the coding is correct. The "interrogation" of the coding preferably takes place before the delivery tube 9 or another delivery element opens the container 3, in particular, pierces a seal of the container 3.

Figure 7:
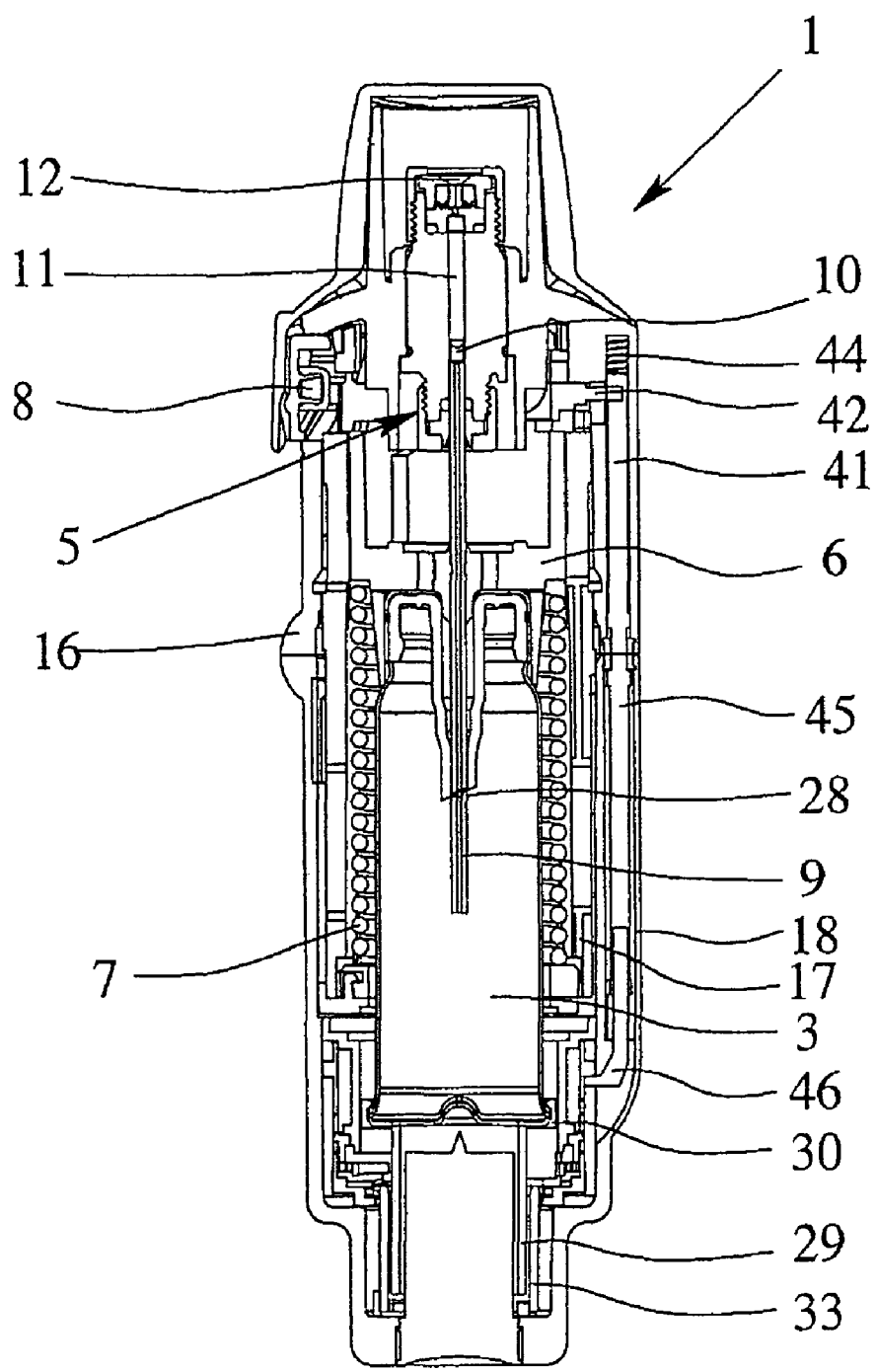
FIG. 7 is a schematic cross-sectional view of the atomizer according to FIG. 3 with the housing part fully drawn back (in the tensioned state)

With the further mounting or sliding of the housing part 18 on the housing upper part 16, the delivery tube 9 initially pierces the seal 27 and breaks through an optional septum S as shown in FIG. 7 (the unbroken septum S being shown in FIG. 6), which shows the atomizer 1 with the fully mounted housing part 18 in a schematic cross-section.

In the course of the mounting or sliding-on, the head of the container 3 is gripped with the holder 6—in particular, in a clamped latched and/or detachable manner. Since the housing part 18 sits on the housing upper part 16 in the clamped state, in which the holder 6 that can move in a stroke-like or linear fashion into the housing upper part 16 is in a bottom position shown in FIG. 7, it is ensured that the container 3 comes into contact with the holder 6 and—where necessary—its base end is pushed against the piercing element 22 and is thereby pierced for aeration. Preferably, in doing so, a connection is established between the, for example, pot- or beaker-shaped, piercing element 22 and the container 3 such that, in the subsequent linear or axial or stroke-like movements of the container 3 (together with the holder 6) for pressurization, fluid withdrawal and or fluid delivery, the piercing element 22 remains in contact with the container 3 or the container base 21, and therefore follows the linear or axial movement of the container 3.

Figure 8:
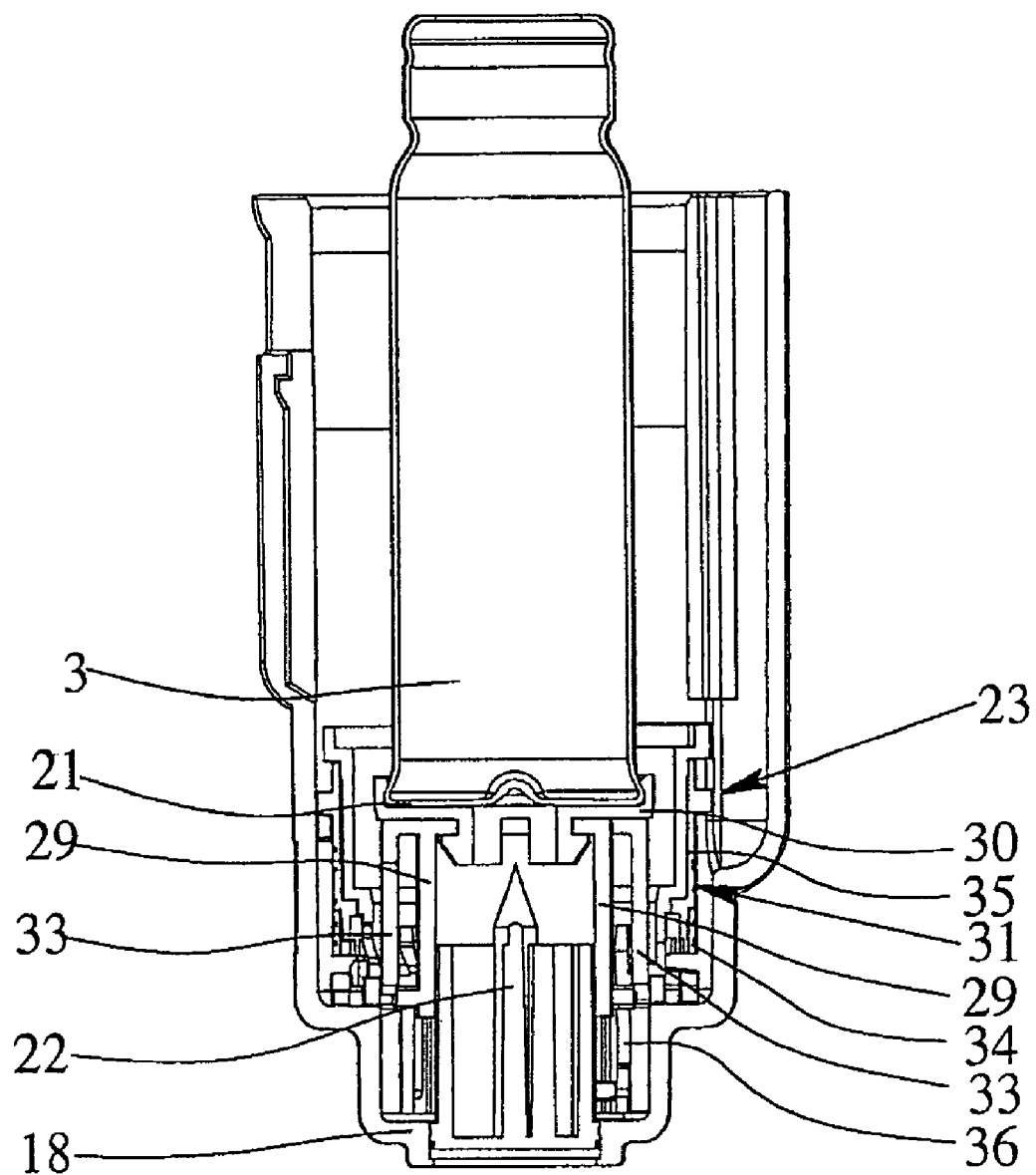
FIG. 8 is an enlarged schematic cross-sectional view of the lower section of FIG. 7 in an initially tensioned state.

The partial schematic cross-section according to FIG. 8 shows the atomizer 1 in the area of the container base 21 and the free end of the housing part 18 at the time of initial tensioning. Therefore, the container 3 is still essentially in its upper axial end position in the illustration according to FIG. 8. The piercing element, in the example shown is in particular indirectly held via the connection element 29 in a latched or clamped fashion by an adapter 30 arranged on the container 3, so that the piercing element 22 remains constantly in contact with the container base 21 or keeps a corresponding air vent in the container floor 21 open. As a result of this aeration, the bag 4 in the container 3 can collapse when fluid is withdrawn without a vacuum building up in the container 3.

The adapter 30 is preferably made from plastic and is, in particular, mounted in a non-detachable fashion on the container 3, preferably being clamped, glued or molded thereto, or cast onto it. Basically, the adapter 30 can be integral with the container 3 or can be formed by the container itself. The adapter 30 is preferably made from a material that is also suitable for the following functions that have still to be explained, in particular plastic.

The counter device 23 is designed for counting the operations of the atomizer 1 and/or the number of containers 3 inserted—preferably both. In particular, the counter device 23 has a first counter 31 for counting operations of the atomizer 1, as indicated by way example in FIG. 8, and a second counter 32 for counting the number of containers 3 inserted or used, as indicated by way of example in FIG. 5.

When counting the operations of the atomizer 1, in particular, each withdrawal of fluid 2 from the container 3, each tensioning of the pressurizer 5 or the drive spring 7 or each atomization is registered and counted as an operation of the atomizer 1. In particular, therefore, a fluid withdrawal, fluid delivery, pressurization and/or atomization is registered and counted as an operation. Basically, however, it is also possible to register and count any other operation of the atomizer 1. In the following, the counting of operations of the atomizer 1 is also referred to as "operations counting" for short.

Particular preference is for operations counting to take place preferably by the linear, axial and/or stroke-like movement or position of the container 3 or any other part of the atomizer 1, such as the holder 6 or the delivery tube 9 being registered. Registration of the movement or position for operations counting is in particular understood to mean at least the movement in one direction and/or the leaving or arrival at, at least, an end position being registered and counted as an operation of the atomizer 1.

The greatest preference is for the tensioning stroke, the atomization stroke or the reaching or leaving of the end position of the container 3 with the tensioned pressurizer 5 or tensioned drive spring 7—thus, the lower end position in the figures—to be registered and counted as an operation of the atomizer 1. This results in various advantages.

The counter device 23 registers the movement of the container 3 in a preferably mechanical fashion. In particular, the counter device 23 altogether works purely mechanically. However, basically an optical, electrical, inductive, capacitive and/or other contact-free registration of the movement of the container 3 is possible.

With mechanical movement registration, it is advantageous to register and count the tensioning stroke or the reaching of said end position in the tensioned state. The necessary mechanical work for mechanical registration and driving of the counter device 23 or at least the first counter 31 must then only be provided during the tensioning. This can be achieved without a problem, since the tensioning preferably takes place manually. Accordingly, during the atomization or tension release process—thus, the pressurization and atomization through the force of the drive spring 7—no mechanical work is used for counting so that the spring energy can be used exclusively for achieving optimum atomization.

On the other hand, if the atomization stroke or the leaving of said end position is registered in the tensioned state, this has the advantage that the actual atomization process is counted as an operation of the atomizer 1.

In the following, using the first embodiment, just the registration of the tensioning stroke is explained further. Basically, however, any other registration and counting is possible, in particular, also the registration of the atomization stroke or the reaching or leaving of the end position.

The atomizer 1 is tensioned according to the embodiment shown in FIGS. 1 & 2 by the housing part 18 being rotated relative to the housing upper part 16, wherein the drive spring 7 is tensioned in the axial direction via a gear (not shown) that acts upon the holder 6 and the container 3, and in the course of the tensioning, moves from its (upper) end position in the un-tensioned state to its (lower) end position in the tensioned state in a linear or stroke-like fashion, together with the holder 6 and the delivery tube 9, into the housing part 18. In FIG. 8, the container 3 is at the start of the tensioning movement and is therefore still in or relatively close to its upper end position in the un-tensioned state.

In the example shown, the adapter 30 is preferably mounted on the container 3 in such a way that it cannot rotate and is provided with the preferably rotating connecting element 29 which, for its part, has at least one preferably arm-like operating element 33. The operating element 33 transmits the linear movement to the first counter 31, in particular to a first counting ring 34 of the first counter 31. In FIG. 8, a second counting ring 35 of the counter 31 is shown. The coupling of the two counting rings 34, 35 is explained further by means of FIG. 10.

The connecting element 29 or the operating element 33 is deflected via a suitable guide, in particular a sliding block guide having at least one guide surface 36 that is inclined relative to the direction of movement of the container 3, such that the linear or axial tensioning movement of the container 3 is converted into a rotary movement of the connecting element 29, operating element 33 and/or at least first counting ring 34, so that the first counting ring 34 is turned further by one increment or one counter step for each tensioning stroke.

Figure 9:
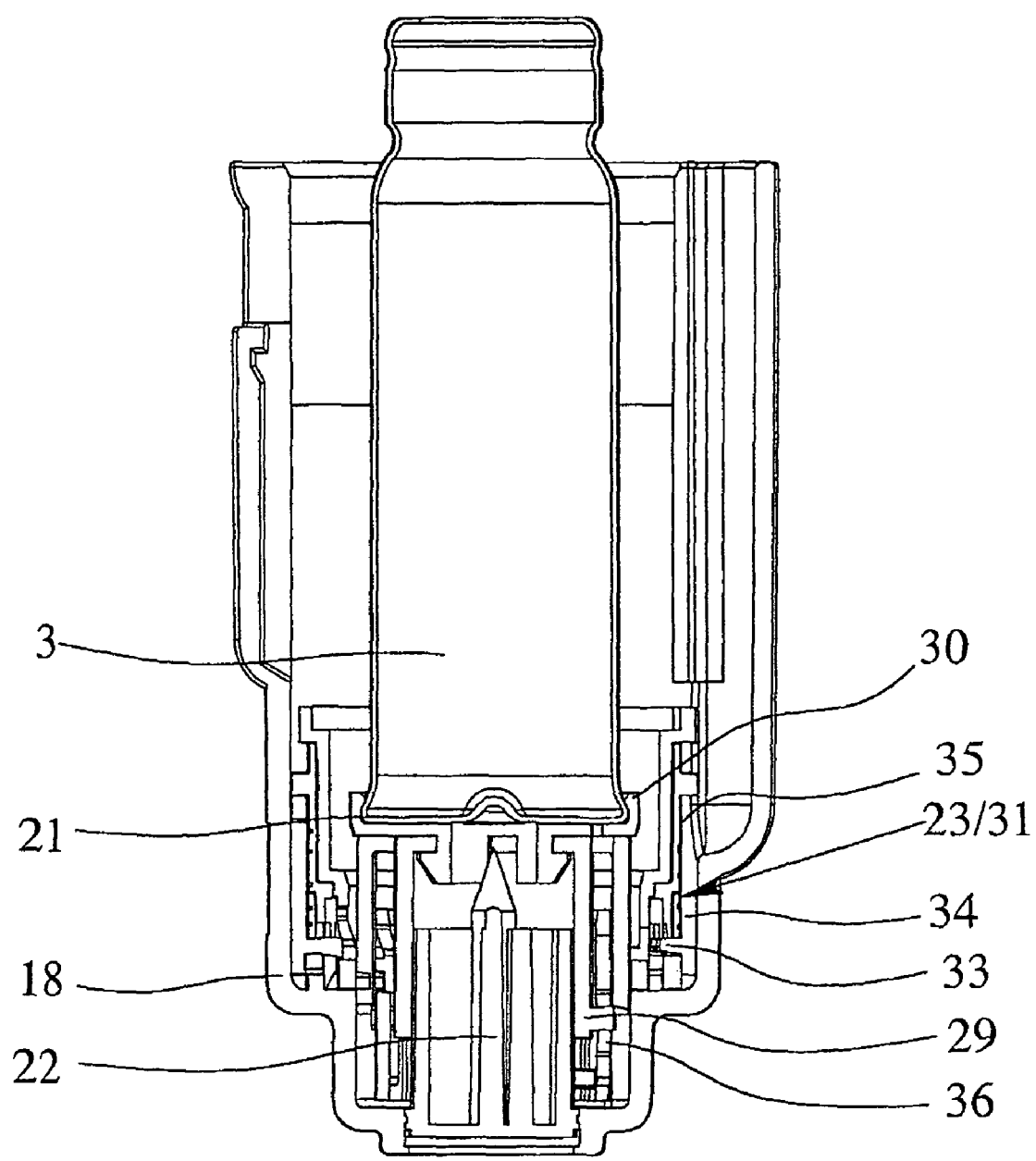
FIG. 9 is a schematic cross-sectional view according to FIG. 8 with further tensioning.

FIG. 9 shows how the connecting element 29 or the at least one operating element 33, in the course of the further tensioning movement, engages the first counting ring 34 and is rotated on the basis of the sliding block guide. In particular, an enforced guidance is envisaged so that, for each tensioning, the first counting ring 1 is forced to rotate further by one counter step.

As already explained, instead of the tensioning movement, however, the atomization stroke of the container 3 can be registered during the pressurization and atomization. The registration can take place by a corresponding or the like mechanism. In particular, the sliding block guide or another forcible guide converts the outward movement into a rotary movement for the first counting ring 34.

The sliding block guide is preferably designed in such a way that the container 3 cannot be detached from the housing part 18, but is at least movable essentially in a stroke-like fashion only, where this is necessary for the tensioning and atomization strokes when using the atomizer 1.

Figure 10:
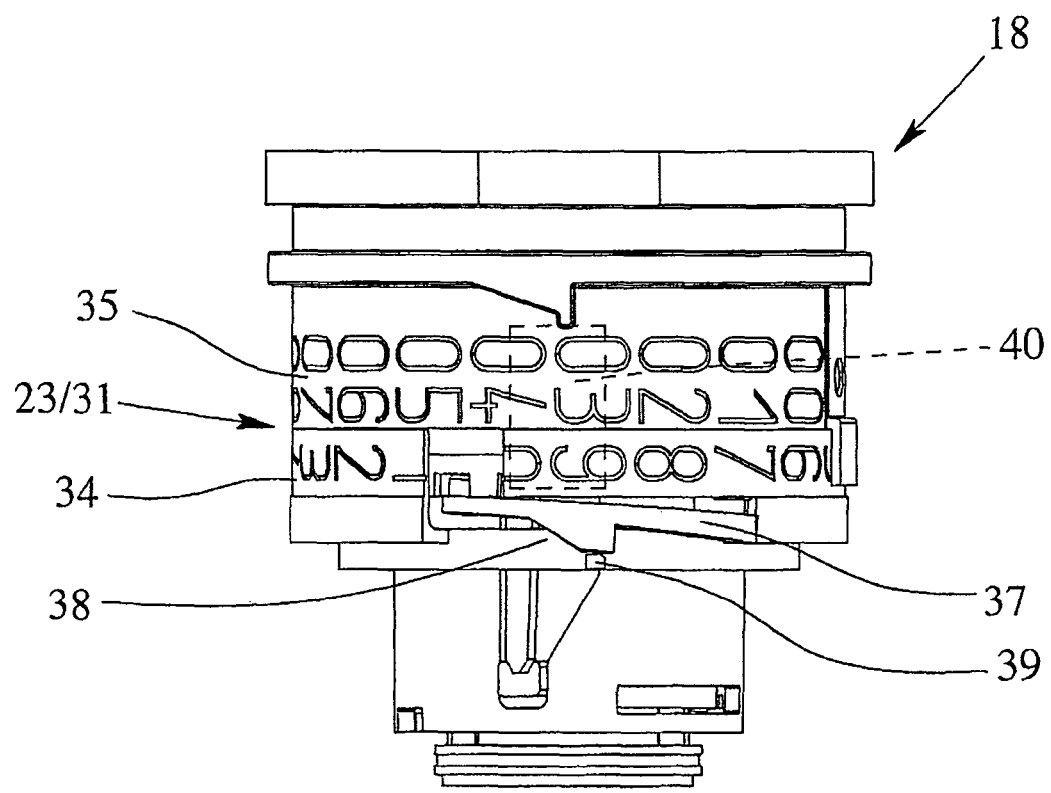
FIG. 10 is a schematic cross-sectional view of the lower end of the atomizer according to FIG. 7 with a first counter of a counting device of the atomizer and with a see-through lower housing part.

The schematic view according to FIG. 10 shows a possible coupling between the first counting ring 34 and the second counting ring 35. In the example shown, the first counter 31 has a transport arm 37, which is carried with it by the first counting ring 34 and when it reaches a certain counting position is deflected via a ramp 38, and for example, an operating nose 39 on the housing side in such a way that its front end engages in the second counting ring 35 at the front end or in another manner. The second counting ring 35 is then further rotated along with the first counting ring 34 by one increment or one counter step. Then, the second counting ring is decoupled so that the first counting ring 34 can count a defined number of counter steps without turning with it the second counting ring 35 with it.

In order to guard against unintentional rotation of counting rings 34, 35, catches, detent pawls or the like (not shown) can be provided. In particular, with regard to the realization possibilities and further considerations on the design of the first and/or second counters 31, 32 reference is also made to German Patent Application DE 100 61 723 A1.

By preference, numbers or other symbols on the counting rings 34, 35 and an assigned, not expressly shown window, in the housing part 18 or the like constitute a display device 40.

The first counter 31 is used for operations counting. It can preferably be reset or set or be adjusted by a user. Rather, it is provided that the first counter 31 is supplied in a preset state.

Particularly preferable is for the first counter 31 to be preset so that at the time of the first use, initially, a number of strokes (tensioning movements and tension release movements) can be performed in order to fill the atomizer 1, in particular the delivery tube 9, the pressure chamber 11 and similar completely with the fluid 2 before first use. These so-called priming strokes are preferably not counted by the counter 31 or indicated by the display device 40.

If required, the first counter 31 or the display device 40 can be designed in such a way that the number of operations of the atomizer 1 already performed (in particular without priming strokes) or the number of operations of the atomizer 1 that are still available are displayed to the user.

The counter device 23 or at least the first counter 31 is preferably designed in such a way that the atomizer 1 is locked against further operation and/or against removal of the current container 3 or insertion of a new container 3, if a certain number of operations of the atomizer 1 is reached or exceeded. The locking under these conditions—thus, if no further operation with the current container 3 should be permitted—is referred to for short as the "first locked state".

Figure 11:
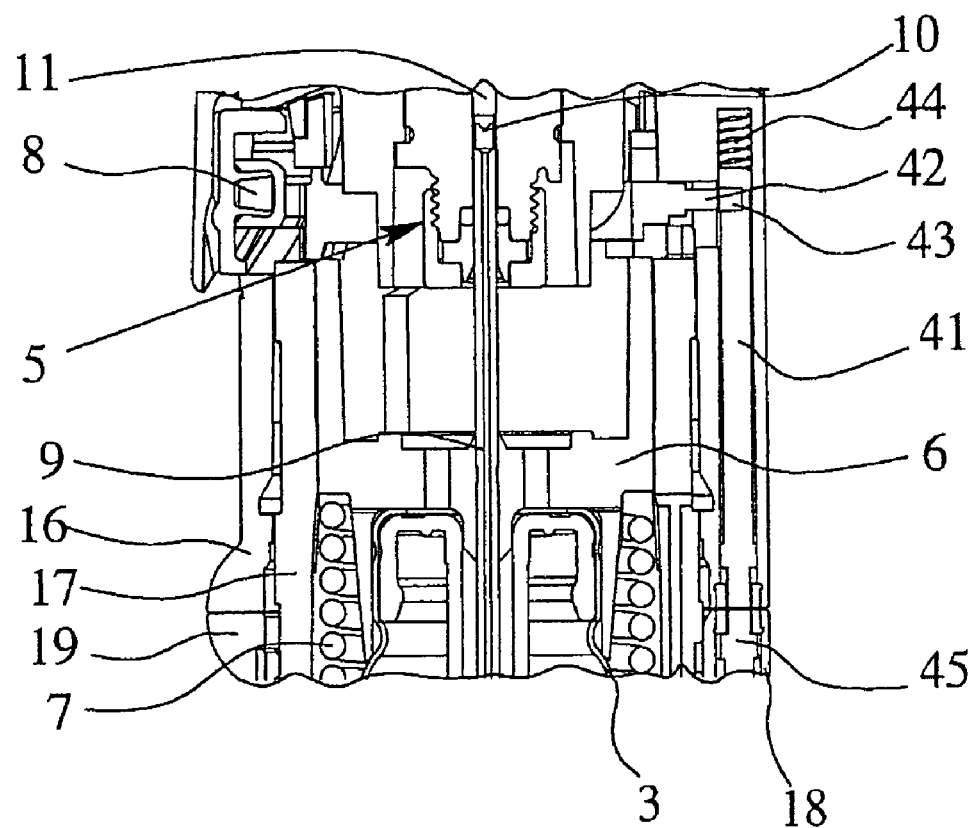
FIG. 11 is an enlarged view of an intermediate section of the atomizer as shown FIG. 7.

For locking in the first locked state the proposed atomizer 1 preferably has an operating lock. FIG. 7 and the enlargement of a section of FIG. 7 according to FIG. 11 show a preferred embodiment. The operating lock has a lock part 41 which in the unlocked state shown does not block a manual operation of the locking element 8 for releasing tension in the drive spring 7—thus a triggering of a pressurization and atomization stroke. Rather, in this state the preferably key-shaped locking element 8 can be pressed by the user in the atomizer 1—in particular diagonally to the longitudinal or movement axis of the container 3—wherein a projection or extension 42 on a circular section on the side opposite the locking element 8 is engaged in a corresponding recess 43 of the lock part 41.

The lock part 41 is pre-tensioned downwards by a spring 44 in the illustrations and is guided by a control part 45, that can be slid longitudinally or axially in the housing part 18, and is held against the force of the spring 44 in the unblocked or locked state in the position shown in FIGS. 7 & 11, in which the projection 42 can engage in the recess 43.

Figure 12:
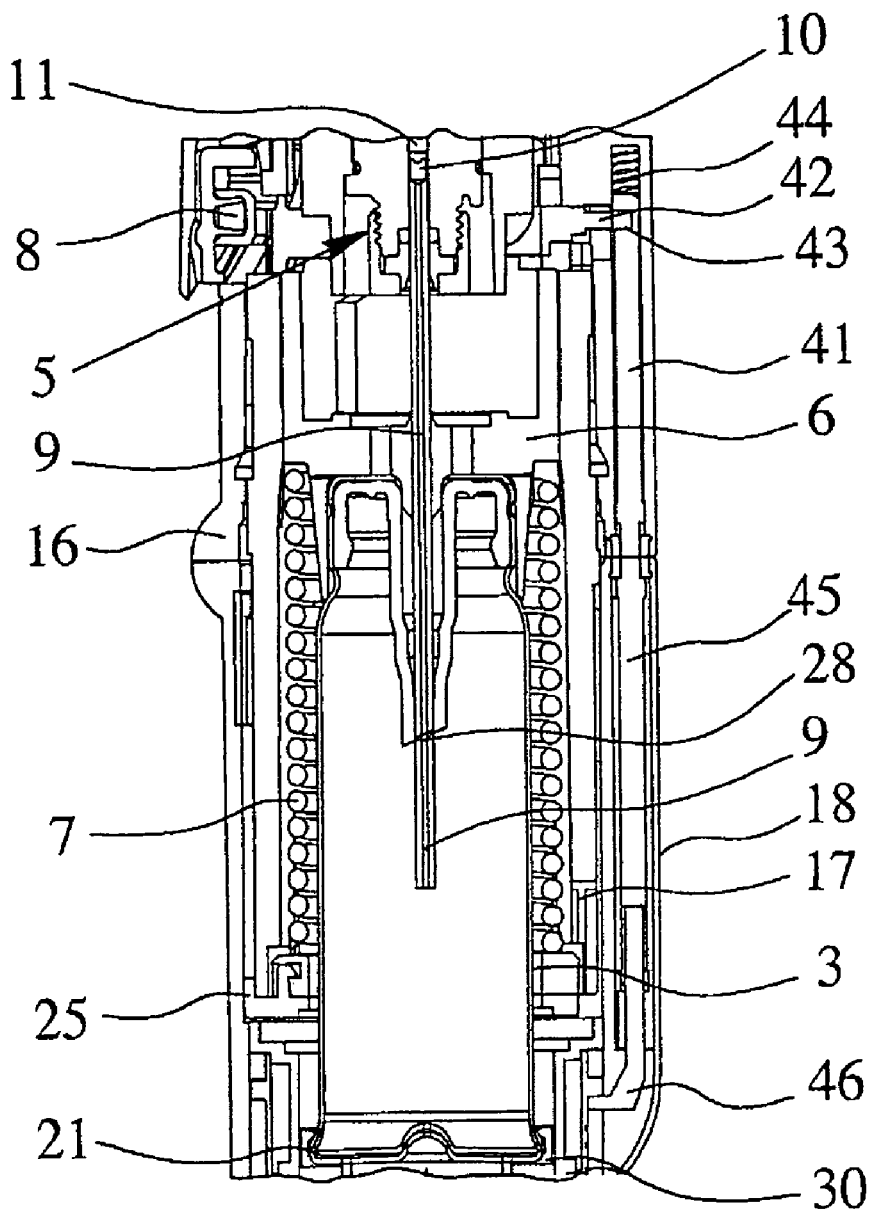
FIG. 12 is a schematic cross-sectional view of a section of the atomizer according to FIG. 10 in the first locked state.

The control part 45 engages with the first counter 31, in particular the second counting ring 35, in such a way that when the number of permitted operations is reached or exceeded the first locked state is brought about, in which control part 45 is released for an axial downward movement. As a result of the force of the spring 44, the lock part 41 is correspondingly displaced axially—in the example shown, downwards—(see FIG. 12), so that in this locked state, the lock part 8 with the projection 42 can no longer engage in the recess 43. This blocks any operation of the locking element 8, and thus, prevents unlocking of the drive spring 7 or the holder 6. Therefore, the atomizer 1 is blocked in the tensioned state if it reaches or exceeds a defined number of permitted operations.

Then, the housing part 18, along with the container 3, can be detached from the housing upper part 16 and exchanged. Particular preference is for the container 3 only to be changeable or replaceable with the counting device 23 or at least with the first counter 3. In the example shown, this is achieved by at least the first counter 31 being arranged in the housing part 18, preferably, in a non-detachable manner, in particular, in a front or far end area of the housing part 18. Furthermore, the container 3, preferably, cannot be detached from the housing part 18 or the first counter 31.

Figure 3:
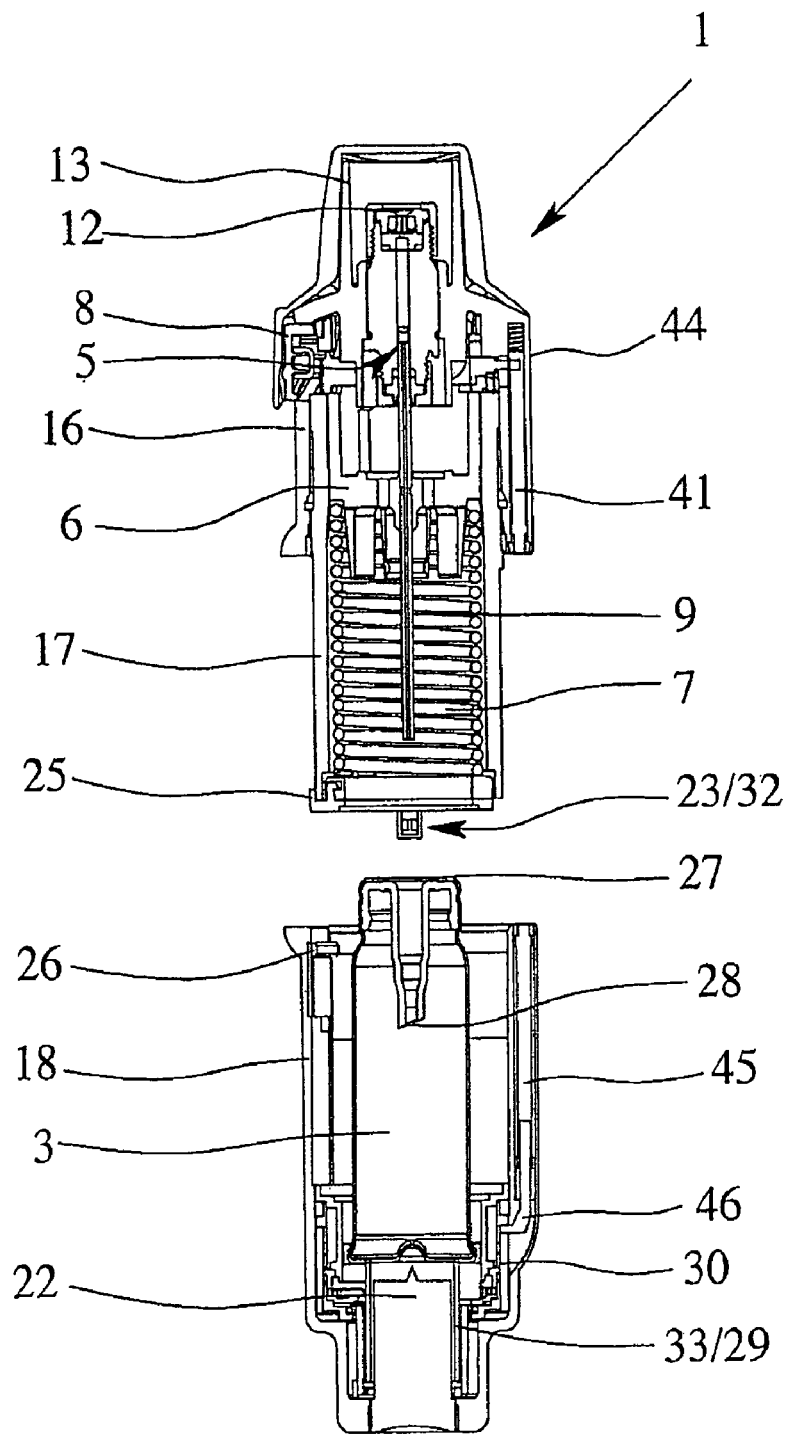
FIG. 3 is a schematic exploded cross-sectional view of an atomizer according to an initial embodiment in the delivered state.

FIGS. 3 & 6 show the lock part 41 in the pushed down and locked state on the housing upper part 18. Only after full mounting of a new housing part 18 with a new, full container 3, and a new first counter 31 is the lock part 41 displaced against the force of the spring into the unlocked, upper position again, as shown in FIGS. 7 & 11. Only in this state can the atomizer 1, in particular, the locking element 8, be operated again, and the atomizer 1 thus have the tension released and be used once more.

Figure 13:
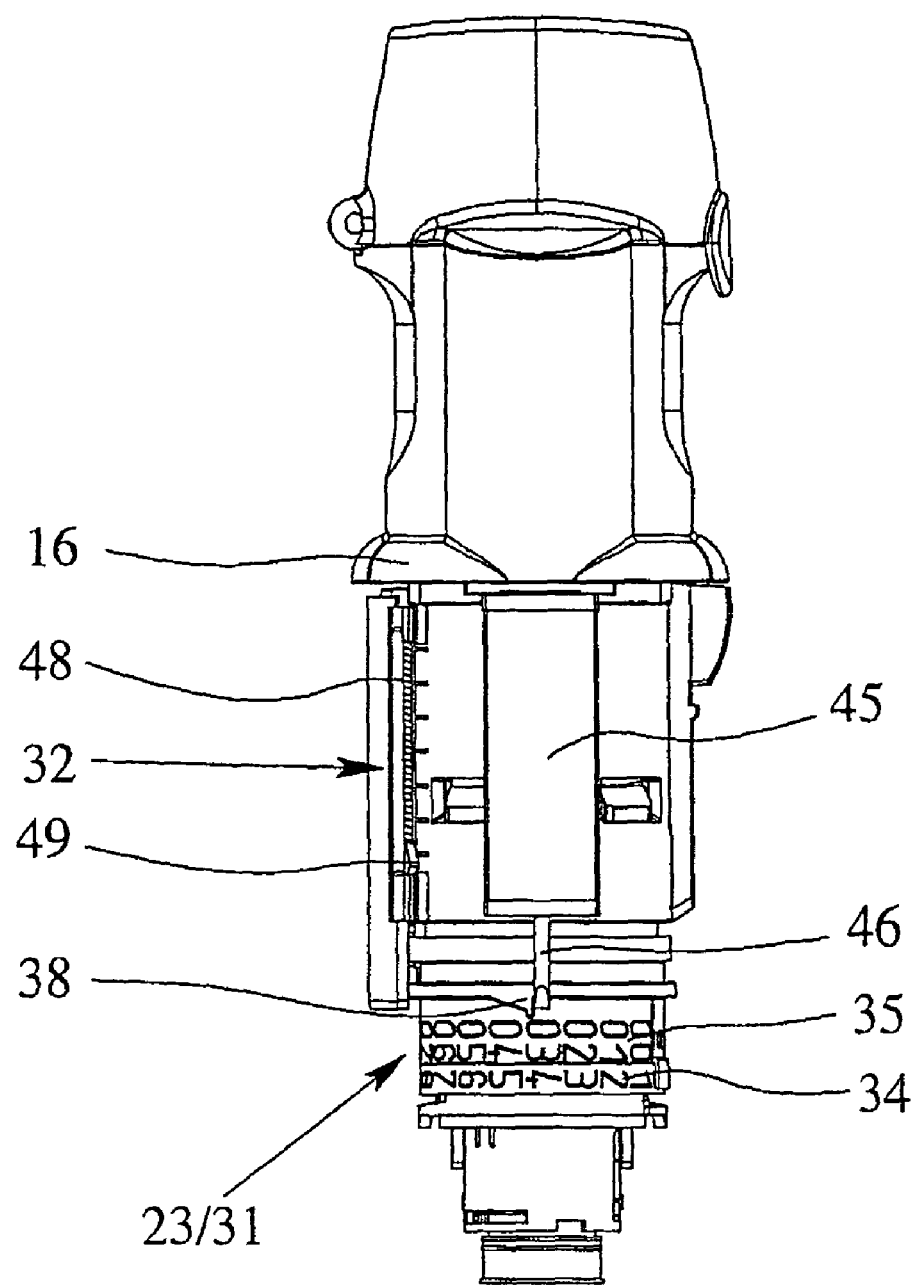
FIG. 13 is a schematic cross-sectional view of the atomizer according to FIG. 12 without the lower housing part.

The schematic representation of the atomizer 1 without housing part 18 according to FIG. 13 shows a possible coupling of the control part 45 with the first counter 31 or the second counting ring 35. A section 46 of the lock part 45 shown in FIG. 12 rests at its front or crown or axially against the second counting ring 35. When the permitted number of operations is reached or exceeded, the operational lock takes place in that, for example, in the rotational position shown in FIG. 13, the lock part 45 engages in the recess 47 formed on the second counting ring 35 so that it is thereby displaced axially downwards. Accordingly, the lock part 41 then displaces downwards into the locking position of the locking element 8 shown in FIG. 12.

Self-evidently, to create the operational lock, other design solutions are also possible. Furthermore, the operational lock illustrated can also be realized independently of the illustrated counter device 23, in particular also for other atomizers, dispensers or dosing devices.

Alternatively or additionally, the housing part 18, which can be rotated for fluid withdrawal, fluid delivery, pressurization and/or atomization or for tensioning the drive spring 7 in one direction of rotation, can be locked in the first locked state against rotation for tensioning.

However, it is also possible for the atomizer 1 to be used with a single container 3. In this case, it can be envisaged that the housing part 18, after the initial complete mounting on the housing upper part 16, can no longer be detached. Accordingly, the container 3 cannot be changed. Thus, an exchange of the first counter 31 is also unnecessary. Furthermore, the second counter 32 can also be dispensed with.

Figure 14:
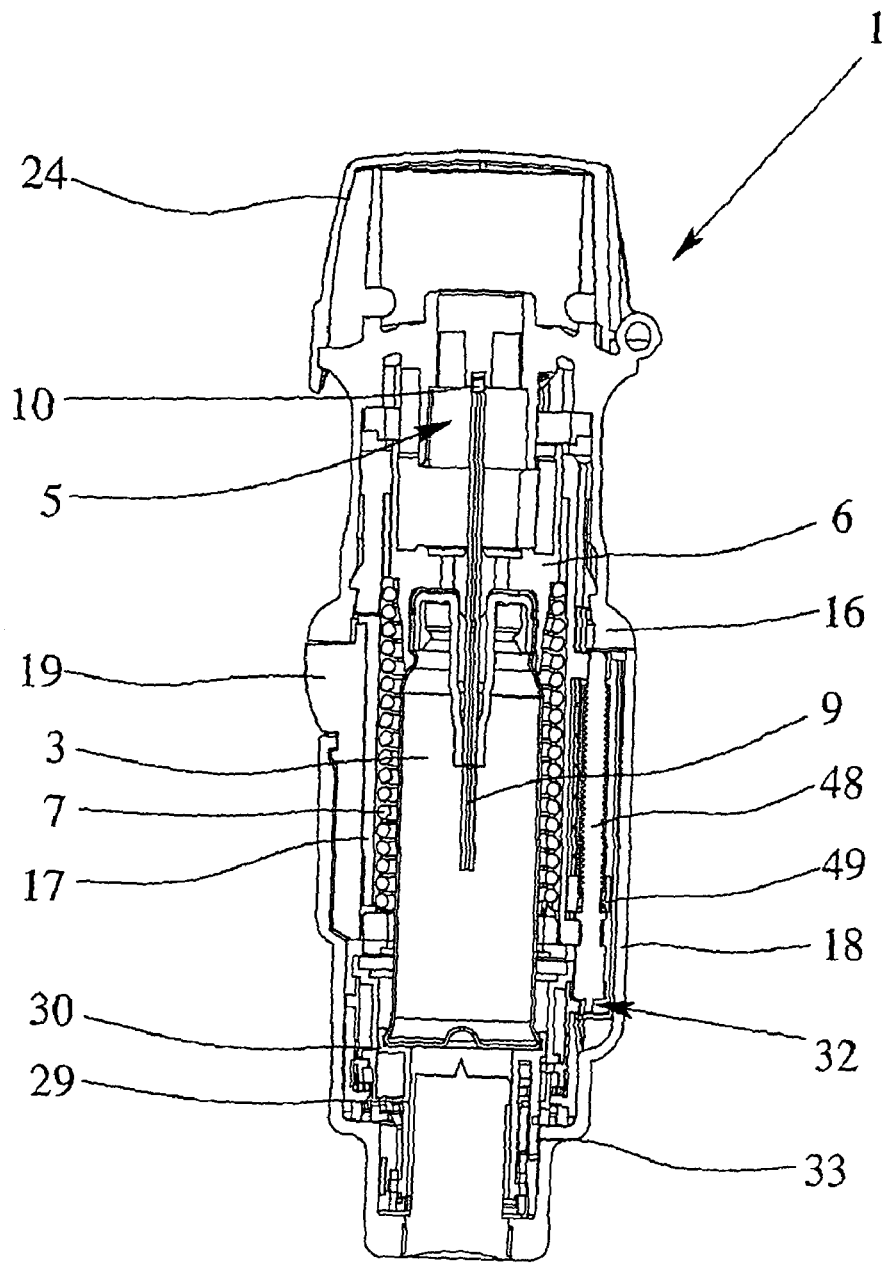
FIG. 14 is a schematic cross-sectional view of the atomizer, rotated by 90° as compared to the view of FIG. 7, with a second counter of a counting device.

FIG. 14 shows the proposed atomizer 1 in a schematic cross-sectional view rotated 90° as compared with FIG. 7. The second counter 32 is shown schematically here. In the example shown, the second counter 32 preferably has a threaded spindle 48 with an assigned rider 49. The threaded spindle 48 can preferably be driven or rotated by the first counter 31 so that the rider 49 is displaced along the threaded spindle 48 according to the counted operations. The position of the rider 49 then represents a measure of the counter value.

Basically, the second counter 32 can count the total—thus with several containers 3—operations of the atomizer 1 performed or still possible. Since with each container 3 only a certain number of operations is permitted, and on the basis of the operational lock explained above, once the defined number has been reached or exceeded, the position of the rider 49 is also a measure of the number of containers 3 used or that can still be used.

Basically, with the present invention the total number of operations already performed or remaining with the atomizer 1 or the number of containers 3 used or still permitted can be used and understood synonymously. In each case, therefore, forward or backward counting is possible as desired.

In the case of container counting—thus, the counting of the number of containers 3 already used or which are still permitted to be used—the second counter 35 is however, according to a particularly preferred design variant, not coupled in a linear fashion with the operational counting, thus the first counter 34. Rather, the container counting or the driving of the second counter 35 or the threaded spindle 48 is not linear but is such that only some of the remaining permissible operations, for example, the last ten permissible operations, with the current container 3 lead to the driving of the threaded spindle, and thus, to container counting. This can be achieved by the appropriate arrangement of cams or other latching elements on the first counter 34, in order to allow the preferred non-linear, in particular quasi-discontinuous container counting. Other solutions are also possible here, however. For example, container counting can take place at the very start of use of a newly inserted container 3.

The optional second counter 35 is preferably driven by the first counter 34. However, it is basically also possible for the container counting to be performed fully independently of the operations counting. In this case, the second counter 35 is preferably driven or operated fully independently of the first counter 34, for example, when the container 3 is inserted, the container 3 floor is pierced, the housing part 18 is fitted, or the like.

The second counter 35 is preferably arranged on the atomizer 1 or housing upper part 16 in a non-detachable fashion. Particular preference is for both counters 34, 35 to be separable from each other, wherein for operations counting the first counter 34, can in each case be exchanged with the container 3 or—according to an alternative that is not described further—reset. In the latter case, the first locked state can be cancelled by removing the housing part 18 and changing the container 3 and the first counter 34 can, for example, be reset to the initial setting. In this case, the container 3 is detachable from the first counter 34 and preferably also from the housing part 18 to allow exchange.

The preferred arrangement of the second counter 35 on the housing upper part 16 or in a non-detachable fashion on the atomizer 1 ensures that the total number of operations already performed or the number of operations still possible of the atomizer 1 and/or the number of containers 3 used or that can still be used—including when the containers 3, the housing part 18 or the like are exchanged—remain available, and in particular, cannot be manipulated by a user.

The counter device 23 or the second counter 32 is preferably designed so that the atomizer 1 is locked against further operation and/or against removal of the current container 3 or the insertion of a new container 3, if a certain number of containers 3 are used, and if necessary, also a certain number of operations of the atomizer 1 with the current container 3 are reached or exceeded. The locking under these conditions is referred to as the "second locked state" for short.

From the above explanations, it can be seen that instead of the criterion that a certain number of containers 3 inserted is reached or exceeded, the number of containers 3 that can still be used can also be assessed. In this case, the locking takes place, if no further containers are permitted to be used, if applicable again only after the defined number of permitted operations of the atomizer 1 with the current container 3 has been reached or exceeded.

Alternatively or additionally, the total number of operations of the atomizer 1 with several containers 3 can be used accordingly and applied as a criterion as can be seen from the above explanations.

In the second locked state, a container locking or an atomizer locking takes place which can no longer be reversed. In the following, a preferred embodiment of the atomizer locking is explained in more detail using FIGS. 15 to 17.

Figure 15:
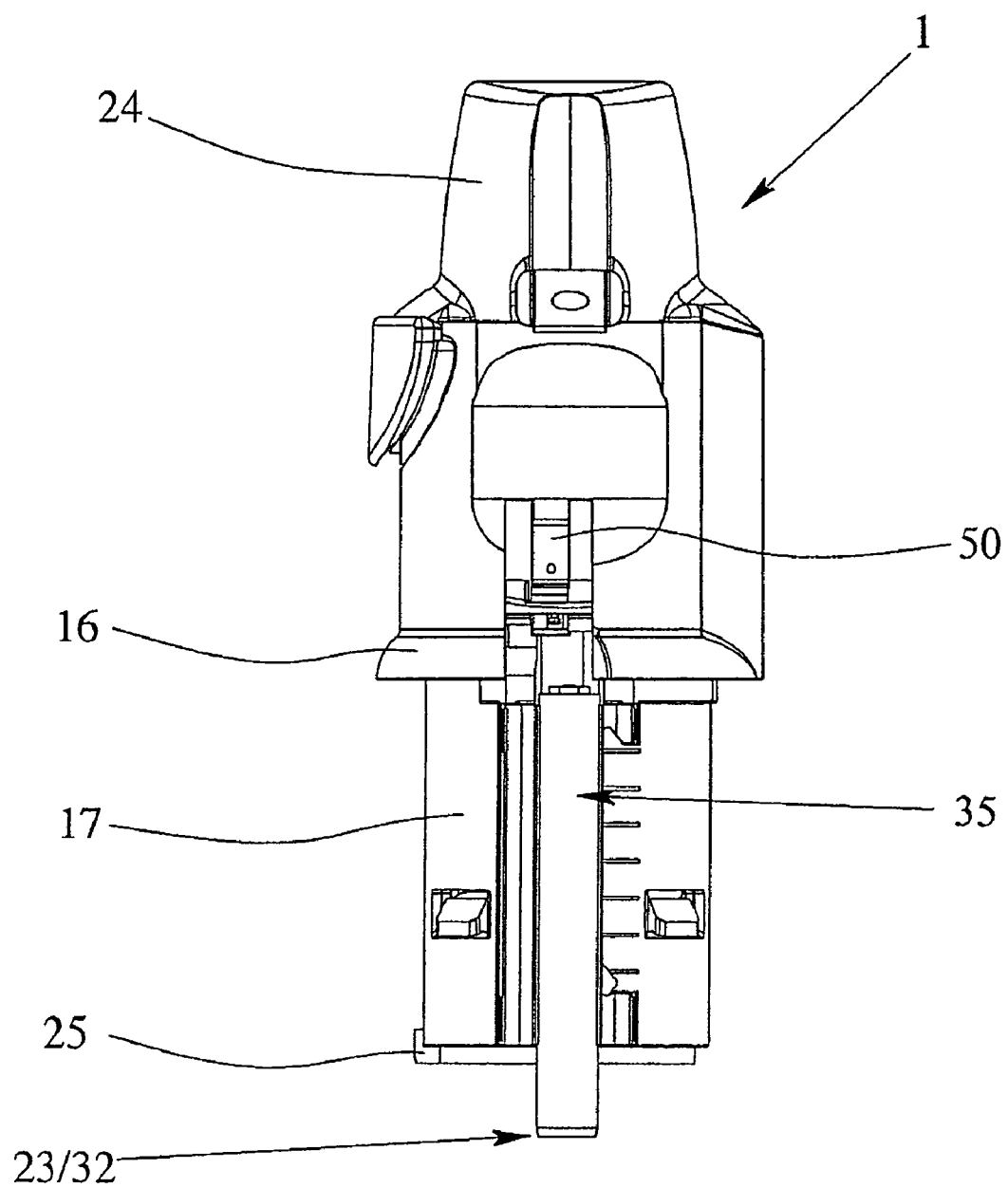
FIG. 15 is a schematic cross-sectional view of a housing upper part of the atomizer according to FIG. 14 with the second counter.

FIG. 15 shows a schematic side view of the housing upper part with the second counter 35, cut away in part for illustration purposes, wherein the threaded spindle 48 and the rider 49 are concealed. In the housing upper part 16, a blocking element 50 is arranged, in particular in the form of a retaining spring.

Figure 16:
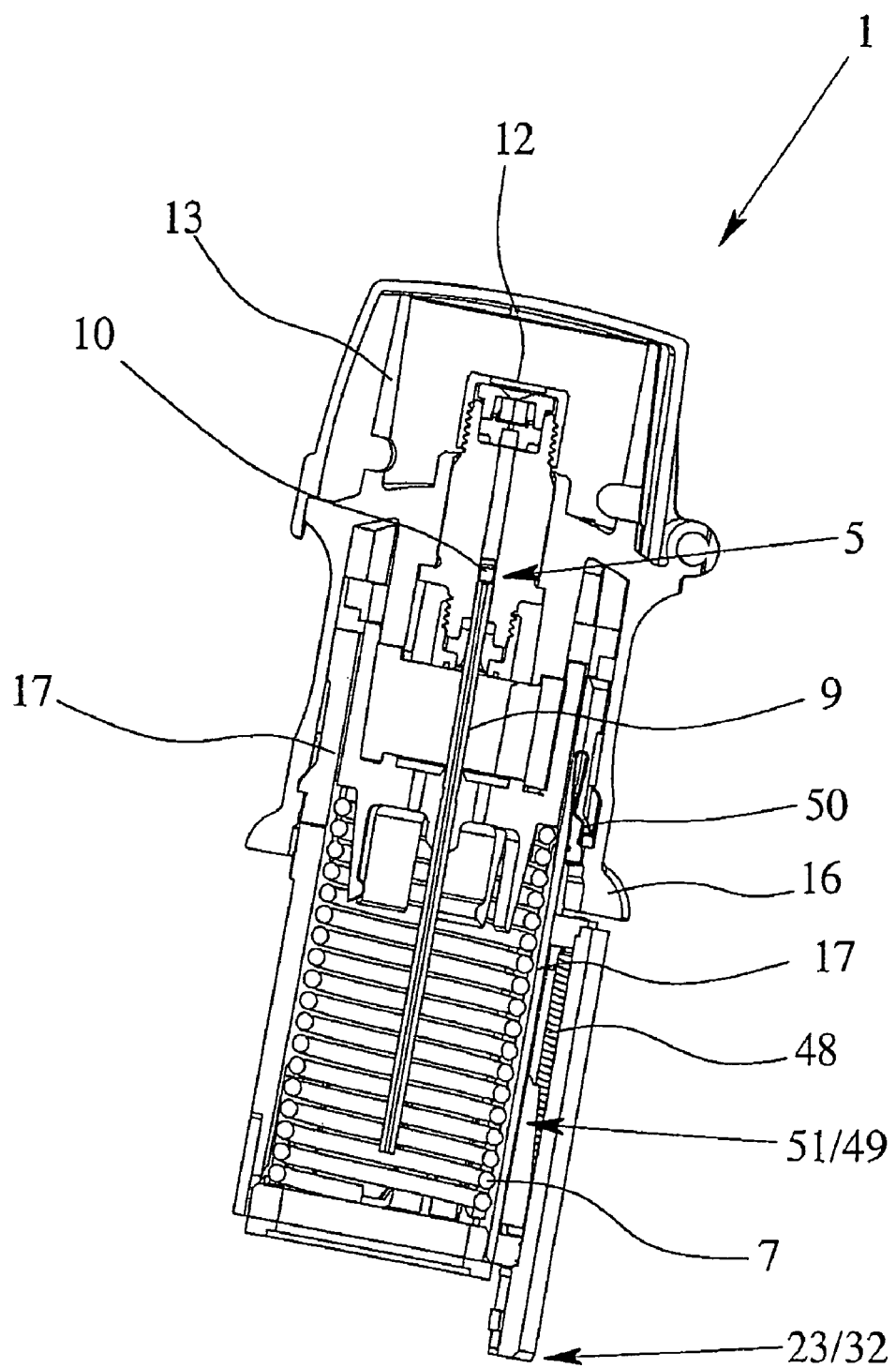
FIG. 16 is a schematic cross-sectional view of a section of part of the second counter according to FIG. 15 in the unlocked state.

The cut-away cross-sectional drawing of FIG. 16 shows that the retaining spring in the unlocked state sits in a recess in the inner part 17, without the rotation of the inner part 17 relative to the housing upper part 16 when the atomizer 1 is tensioned being blocked. In particular, in the unblocked state shown, the retaining spring is held by the housing upper part 16 or an undercut on the inner part 17 in the recess in the inner part 17.

FIG. 16 also shows that an axially adjustable actuator 51 is assigned to the blocking element 50 or the retaining spring and extends as far as the second counter 32 or the threaded spindle 48.

Figure 17:
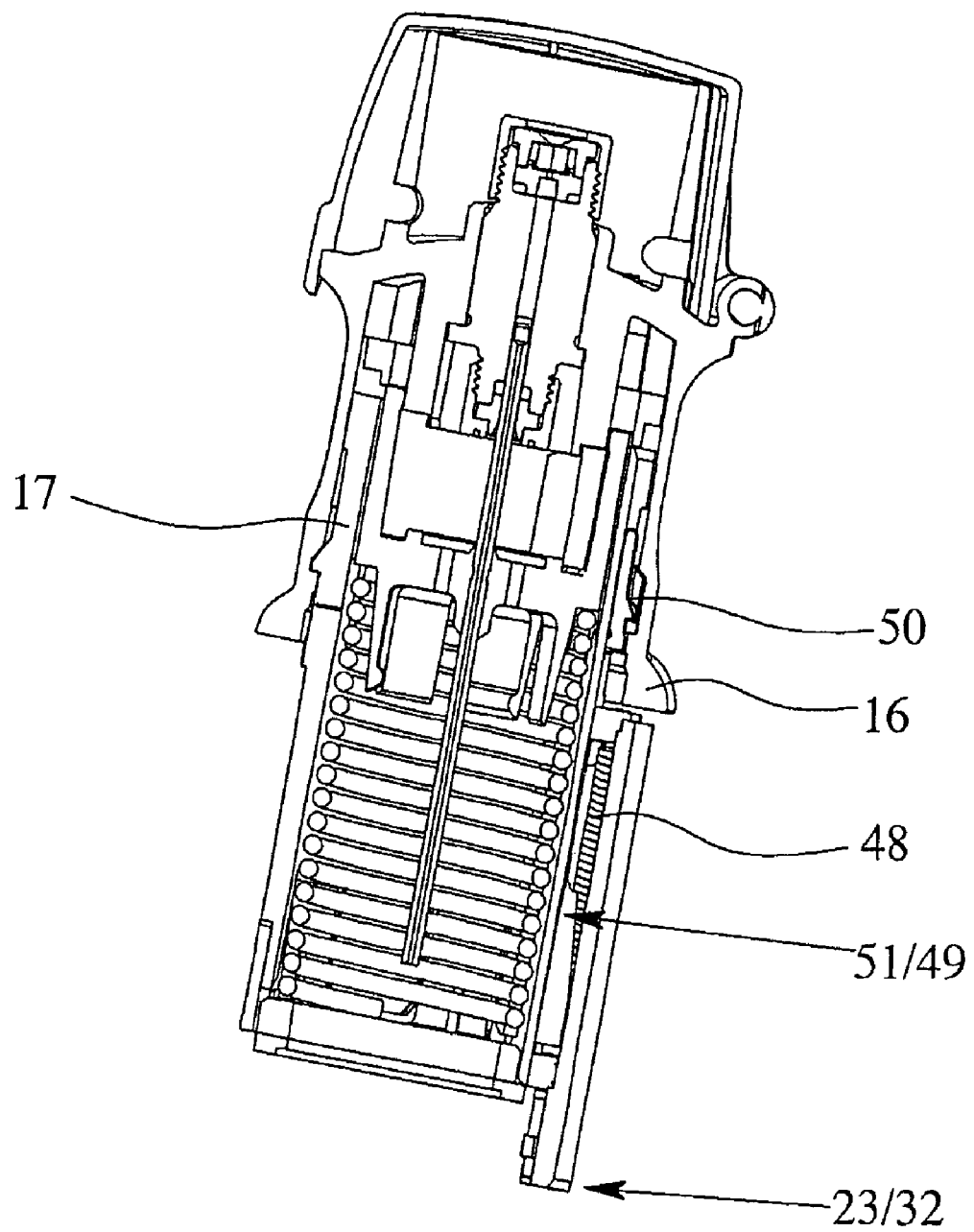
FIG. 17 is a schematic cross-sectional view of the second counter in the second locked state corresponding to FIG. 16.

The actuator 51 is axially displaceable by the rider 49 for atomizer locking, and in the illustration according to FIG. 17, has already been displaced axially upwards by the rider 49. This displacement leads to the blocking element 50 blocking the relative rotation of the housing upper part 16 and inner part 17. In particular, the blocking takes, place in the example shown, through the retaining spring that has been displaced axially upwards rebounding and engaging in a corresponding recess in the housing upper part, so that a preferably undetachable blocking or locking in the second locked state occurs.

The second locked state prevents the atomizer 1 from being used beyond its permitted usage period. Preferably, in the second locked state, a rotation of the inner part 17, and thus, also the housing part 18, for tensioning the atomizer 1 or its drive spring 7 is blocked.

Alternatively or additionally, in the first or second locked state, the detachment of the housing part 18 from the atomizer 1 and/or the operation of the locking element 8 or other operation of the atomizer 1 can also be locked.

In the first embodiment, the second counter 32 does not have a display of the counter value or the position of the rider 49. However, if this is needed, it can be achieved without any problem.

In the following, further preferred embodiments of the proposed atomizer 1 are explained in more detail, wherein, however, only the essential differences compared with the atomizer 1 according to FIGS. 1 & 2 and compared with the atomizer 1 according to the first embodiment are emphasized. The statements made so far, therefore, apply accordingly or in addition.

Figure 18:
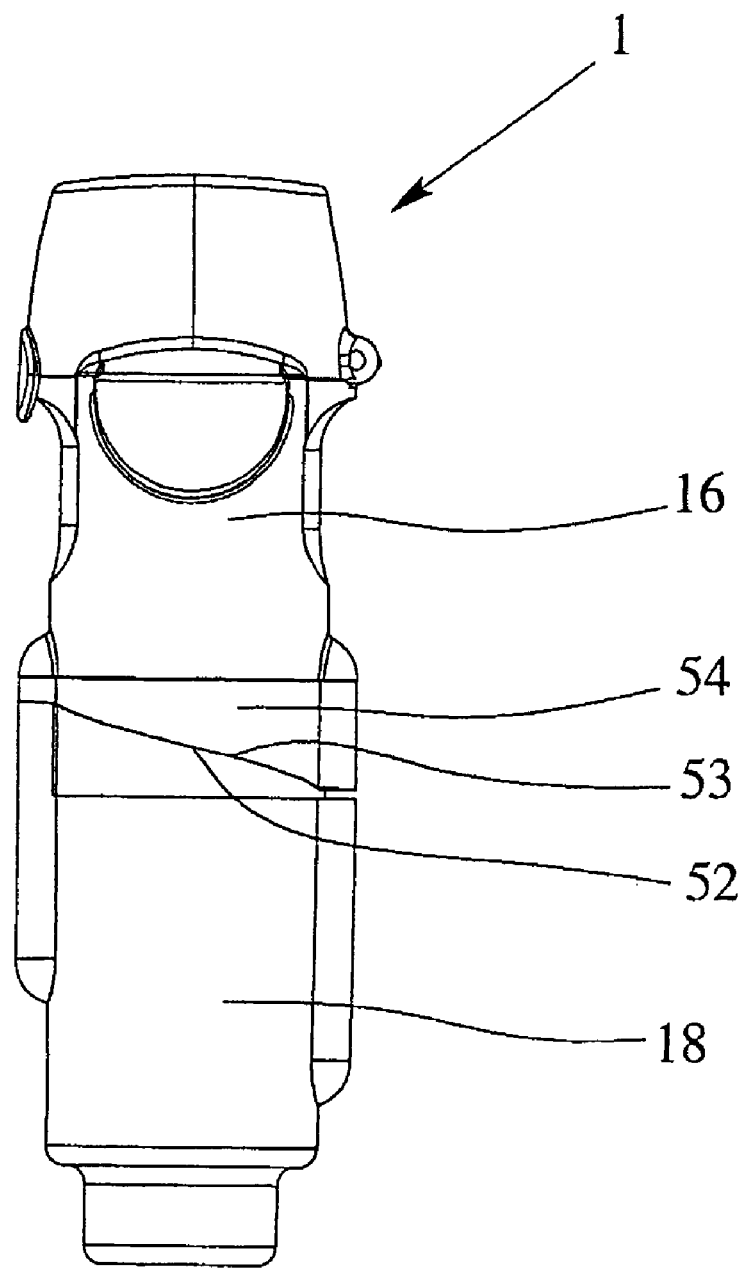
FIG. 18 is a schematic view of an atomizer according to a second embodiment of the invention.

FIG. 18 shows a schematic view of a proposed atomizer 1 according to a second embodiment. The housing part 18 is shown in a see-through manner for illustration purposes. With the second embodiment, also the counter device 23 is envisaged and in particular, in turn, arranged—at least with a first counter 31—in the housing part 18 or on another detachable housing part of the atomizer 1.

With the second embodiment, the housing part is rotatable in the opposite direction to the direction of rotation for tensioning the atomizer 1 or the drive spring 7 in a release direction for axial detachment (preferably also of the container 3). In particular, the rotation in the release direction is only possible with the atomizer 1 tensioned. On the housing part 18 and/or on the atomizer 1, a sliding surface 52, 53, is arranged or formed that is inclined relative to the axis of rotation (longitudinal axis) of the atomizer 1 or the direction of movement of the container 3. When the housing part 18 is rotated in the release direction, according to the principle of inclined planes, an axial release of the housing part 18 and preferably the container 3 from the atomizer 1 or the housing upper part 16 takes place. Accordingly, the release is simplified substantially.

In the example shown, the sliding surface 52 is formed by the diagonally cut end of the housing part 18. A complementing inclined sliding surface 53 is formed by an adapter 54 which, when the housing part 18 is detached from the atomizer 1, remains on the housing upper part 16 or inner pail 17. For axial detachment, the housing part 18 can also be rotated relative to the adapter 54 and can thereby be forcibly moved back axially from the adapter 54.

In the course or for the purpose, of detaching the housing part 18 from the atomizer 1 or housing upper part 16, the holding element 19, which is not shown in FIG. 18, preferably, must be manually operated or depressed.

As explained above, the axial detachment of the housing part 18 and preferably the container 3 through the principle of inclined planes or through rotation in the release direction— and thus, against the tensioning direction—if necessary, can also be performed independently of the proposed counting or counter device 23 in the described atomizer 1 or in other atomizers, dispensers, dosing devices or the like.

Figure 19:
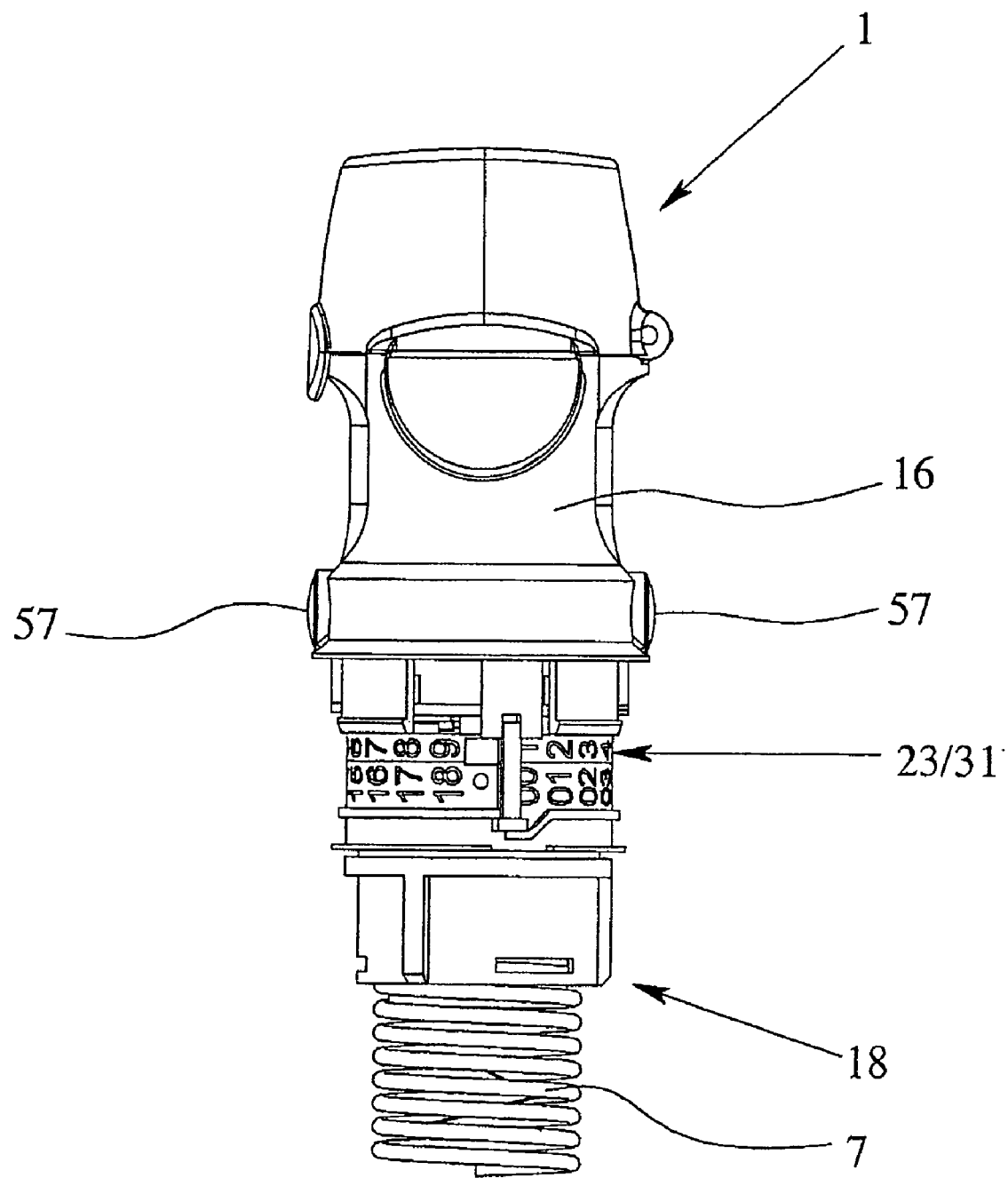
FIG. 19 is a schematic view of an atomizer according to a third embodiment of the invention.

FIG. 19 shows a proposed atomizer 1 according to a third embodiment. The housing part 18 is shown in a see-though manner for illustration purposes.

With the third embodiment, the atomization of fluid 2 preferably takes place, as in the first and second embodiments, exclusively through the force of the drive spring 7. In contrast to the first or second embodiment, however, the drive spring 7 in the third embodiment is arranged in the detachable housing part 18, and therefore, can be detached with the housing part 18 from the atomizer 1 or the housing upper part 16.

Figure 4:
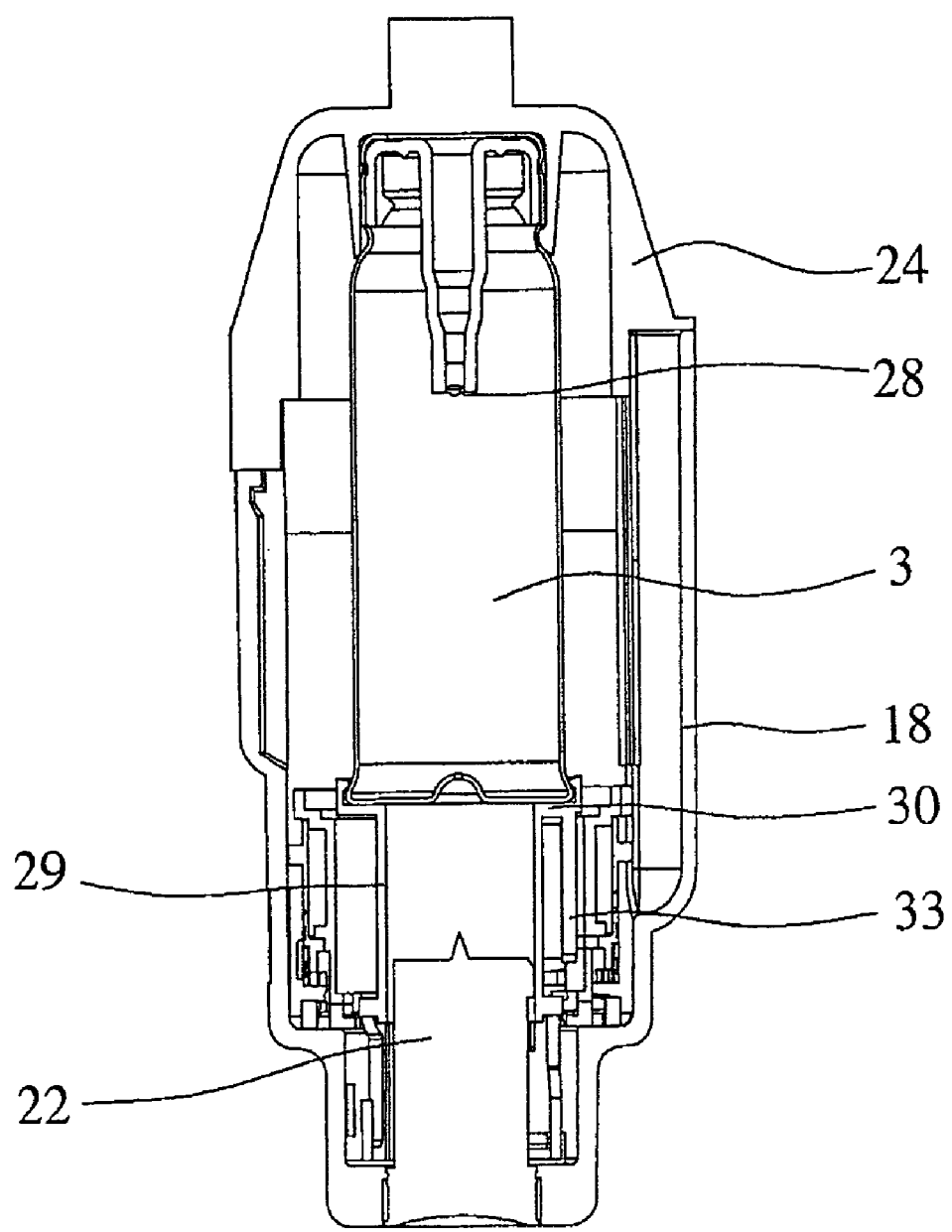
FIG. 4 is a schematic cross-sectional view of the lower housing part of the atomizer of FIG. 3 with the container in the delivered state with an additional protective cap.
Figure 20:
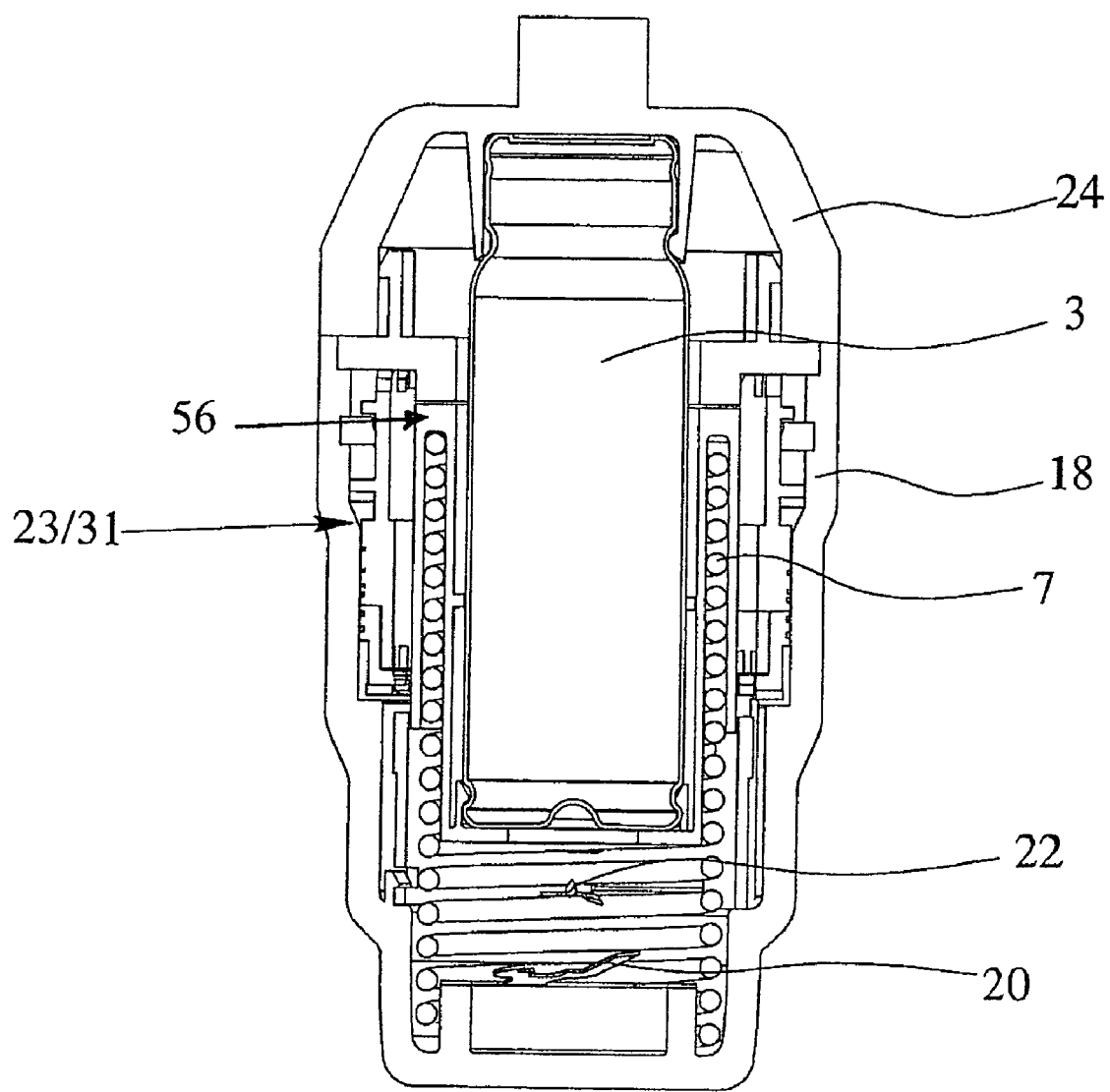
FIG. 20 is a schematic cross-sectional view of a lower housing part of the atomizer according to FIG. 19 with a protective cap in the delivered state.

FIG. 20 shows a schematic cross-section of the housing part 18 with the drive spring 7 and the container 3 in the preferred delivered state, namely separate from the housing upper part 16, in particular with a protective cap 24 according to the first embodiment in accordance with FIG. 4. In the housing part 18, a beaker-shaped seat 56 is preferably arranged for the container 3. In the example shown, the drive spring 7 is supported at one end in annular recess formed by a flange of the container seat 56 and at its other end, in the example shown, in an annular recess formed on the bottom of the housing part 18. The spring 20 and the piercing element 22 correspond in the third embodiment, and at least in essence to the design according to FIGS. 1 & 2.

Figure 21:
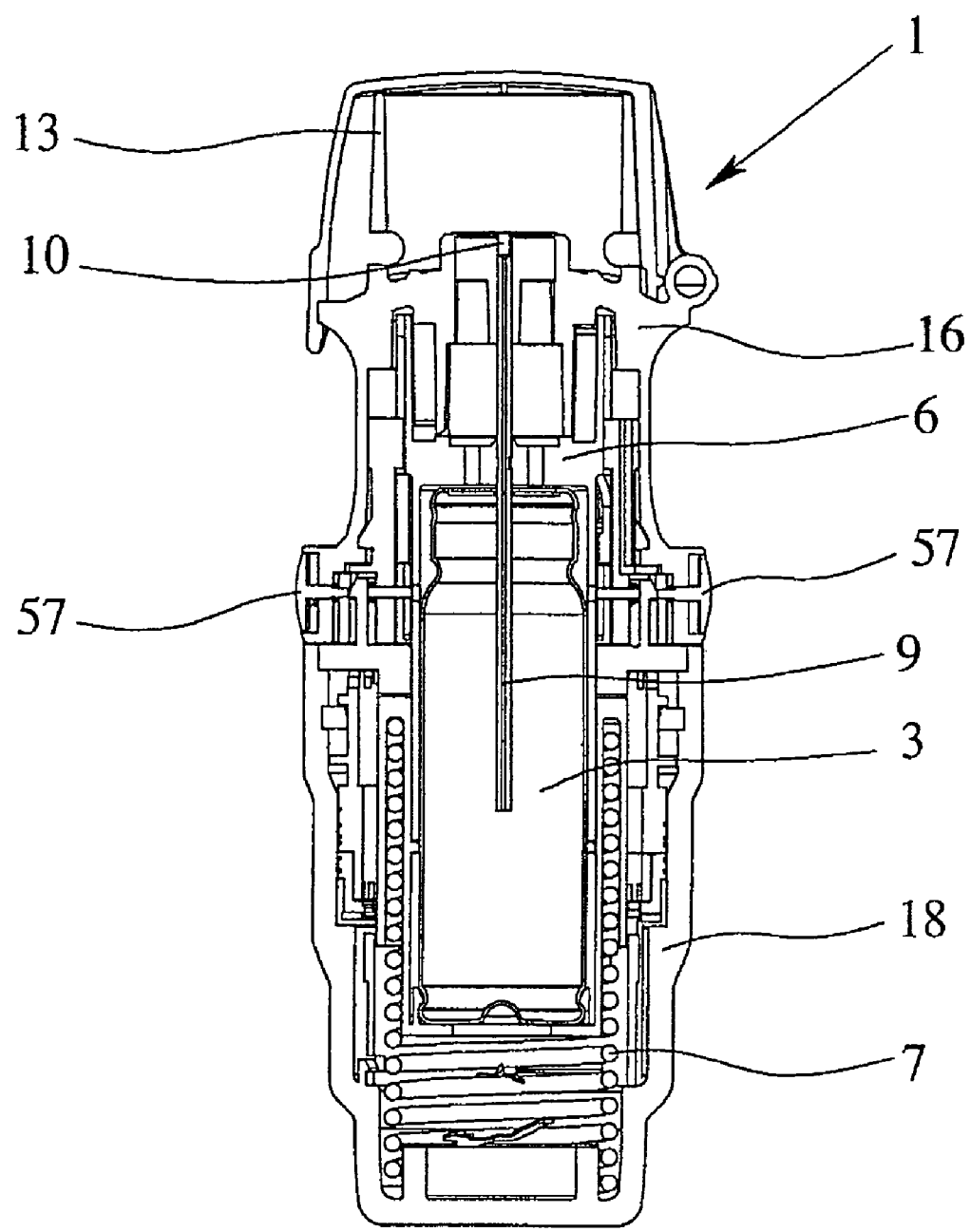
FIG. 21 is a schematic cross-section of the atomizer according to FIG. 19 in the un-tensioned state.

In the delivered state, the drive spring 7 is not tensioned. Following removal of the protective cap 24, the housing part 18 can be mounted oil or slid onto the housing upper part 16, wherein the container 3—as with the first and second embodiment—is pierced or opened by the delivery tube 9 and brought into contact with the holder 6. The schematic cross-section according to FIG. 21 shows this state with the untensioned atomizer 1 and inserted and opened container 3.

In the third embodiment, the holder 6 is preferably extended in a sleeve-like manner to the free end of the housing upper part 16 or to the inlet opening for the holder 3, in particular, beyond the delivery tube 9. This offers a number of advantages.

The delivery tube 9 is protected by the sleeve-like extension against damage.

The sleeve-like extension leads to better guidance of the container 3 when coupling to the holder 6.

The sleeve-like extension is adapted to the seat 56 in the housing part 18 so that good mutual guidance is achieved. Thus, in particular, during tensioning, a possible tilting of the container 3 is at least minimized.

Following insertion of the container 3, when tensioning for the first time, the piercing on the bottom end takes place by the piercing element 22 in the manner already explained previously, in order to aerate the container 3 accordingly.

In the third embodiment, the counter device 23 or the functionality is preferably at least essentially designed to correspond to the first embodiment. The difference is, however, that the first counter 31 is preferably not arranged in the area of the lower end of the housing part 18, but is, instead, in the housing part 18 in the area of the middle of the atomizer 1 or adjacent to the opening of the housing part 18 for accommodating the container 3. The holder 3 and the drive spring 7 are preferably coaxially surrounded by the first counter 3 or the counting rings 34, 35.

The counting, locking or blocking functions correspond, preferably, to those of the first embodiment. However, the counter device 23 with two counters 31, 32, is only an option. If necessary, the counter device 23 can, therefore, be dispensed with or provided for in another way, for example, as in the embodiment according to FIGS. 1 & 2.

A particular advantage of the arrangement of the drive spring 7 in the detachable housing part 18 according to the third embodiment is that, with each change of container, the drive spring 7 is also changed. Thus, in the case of very high multiple use, possible fatigue of the drive spring 7, and thus, an undefined pressurization or atomization behavior can be avoided.

Figure 22:
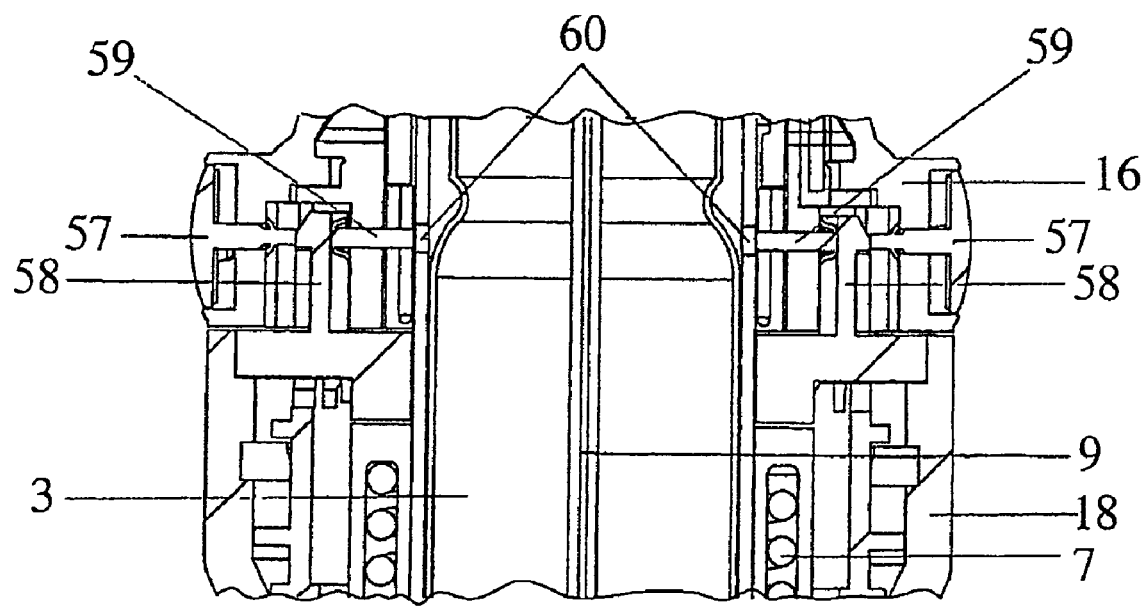
FIG. 22 is an enlarged intermediate section of FIG. 21.

In order to guarantee a secure connection of the housing part 18 with the housing upper part 16, in the third embodiment, a so-called two-finger opener or at least a double lock is preferably provided. In the example shown, in order to detach the housing part 18, two unlocking elements 57 arranged, preferably, on opposite sides of the housing must be operated simultaneously, in particular pressed in. Thus, latching or retaining arms 58 of the housing part 18 from the latching or retaining position shown in FIGS. 21 & 22, in which the housing part 18 is retained in an interlocked manner on the housing upper part 16, can, in the example shown, be deflected elastically inwards, in order to cancel the interlock and allow the housing part 18 to be removed from the housing upper part 16. FIG. 22 is an enlargement of a section of FIG. 21, in order to show the connection of the housing part 18 with the housing upper part 16 by means of the retaining arms 58.

The atomizer 1 is preferably designed so that the housing part 18 can only be removed from the housing upper part 16 when the drive spring is relaxed. This represents a safety measure so that the housing part 18 cannot be removed from the housing upper part 16 when the drive spring 7 is tensioned, in order to prevent the housing part 18 from being catapulted away as the drive spring 7 relaxes.

The locking against detachment or unlocking in the example shown provides for at least a safety bolt 59. Each retaining arm 58 has a safety bolt 59 assigned to it so that—in the un-locked state—when the unlocking element 57 is operated and the retaining arm 58 pivots, the assigned safety bolt 59 is pushed radially inwards into an assigned opening 60 in the sleeve-like extension of the holder 6. In order to release the interlock between the housing part 18 and the housing upper part 16 the retaining arm 58 must be pivoted a long way and the assigned safety bolt 59 displaced a long way radially inwards so that it has to engage in the assigned opening 60.

This radial displacement of the safety bolt 59 is only possible in the un-tensioned state shown in FIGS. 21 & 22 if the openings 60 align with the safety bolts 59.

Figure 23:
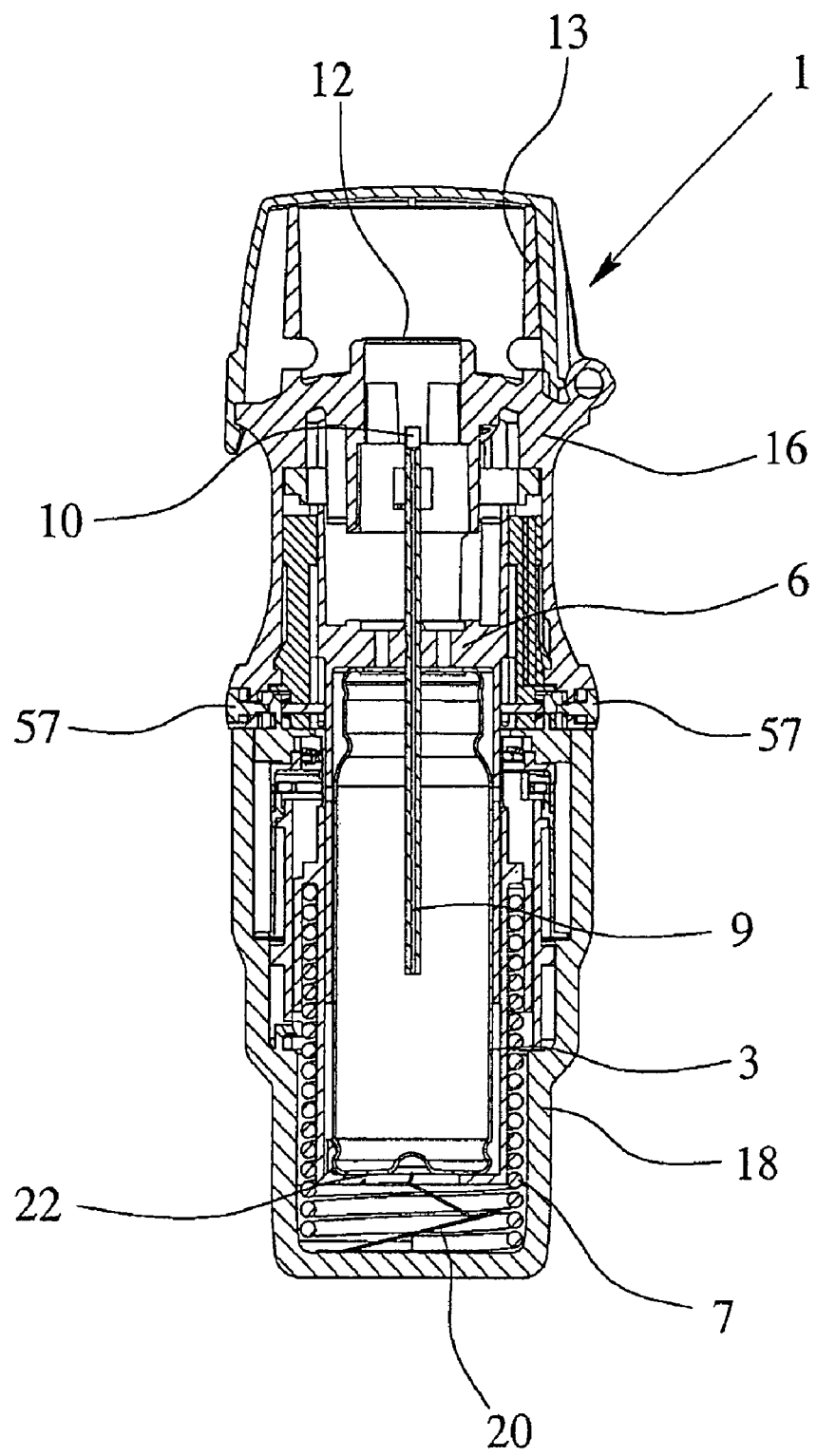
FIG. 23 is a schematic cross-sectional view of the atomizer according to FIG. 19 in the tensioned state.
Figure 24:
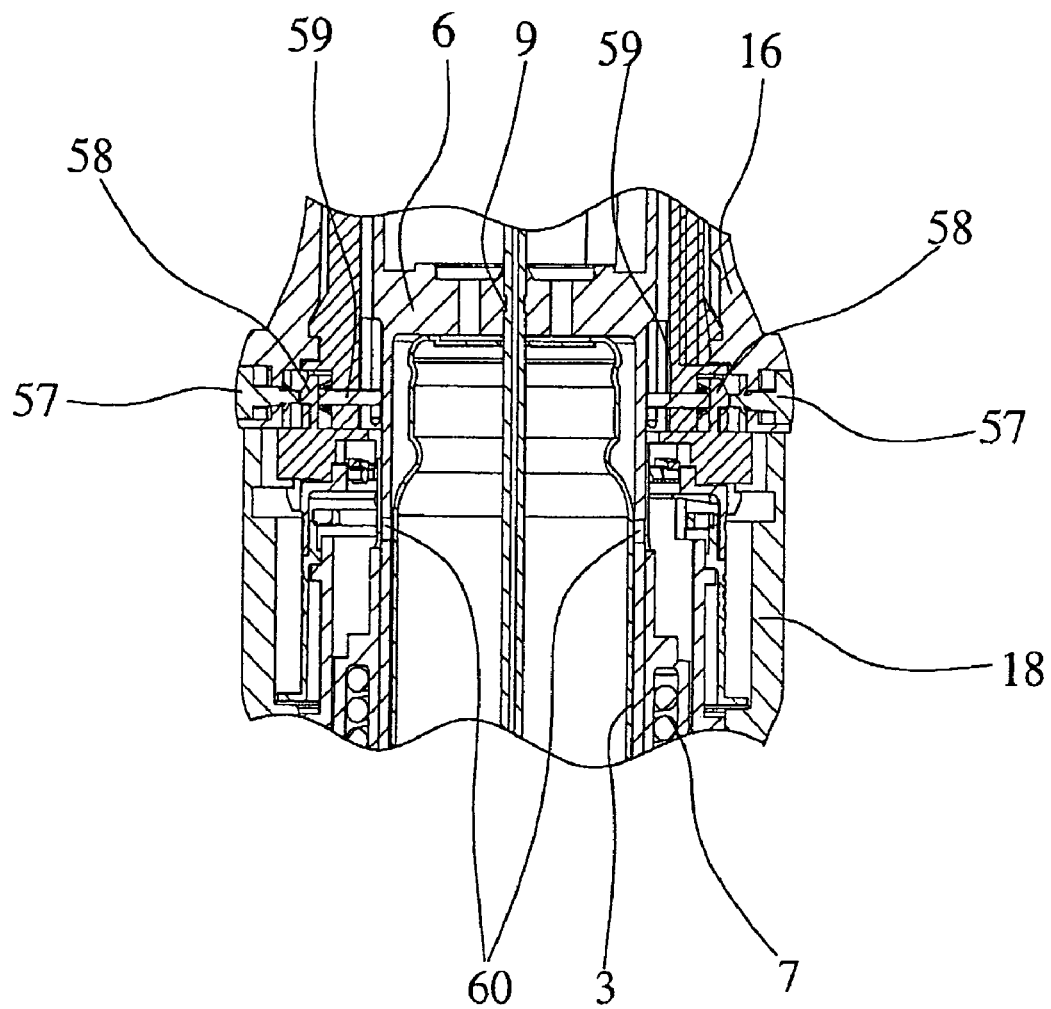
FIG. 24 is an enlarged view of an intermediate section of FIG. 23.

FIGS. 23 & 24 are illustrations corresponding to FIGS. 21 & 22 of the atomizer 1 in the tensioned state. Here, the openings 60 have been displaced downwards. Accordingly, the safety bolts 59 cannot be displaced radially inwards but block a pivoting of the retaining arms 58 when the unlocking elements 57 are operated. Accordingly, the atomizer 1, in this state, cannot be opened or locked. Rather the unlocking and detachment of the housing part 18 is only possible in the fully un-tensioned state of the atomizer 1.

Figure 25:
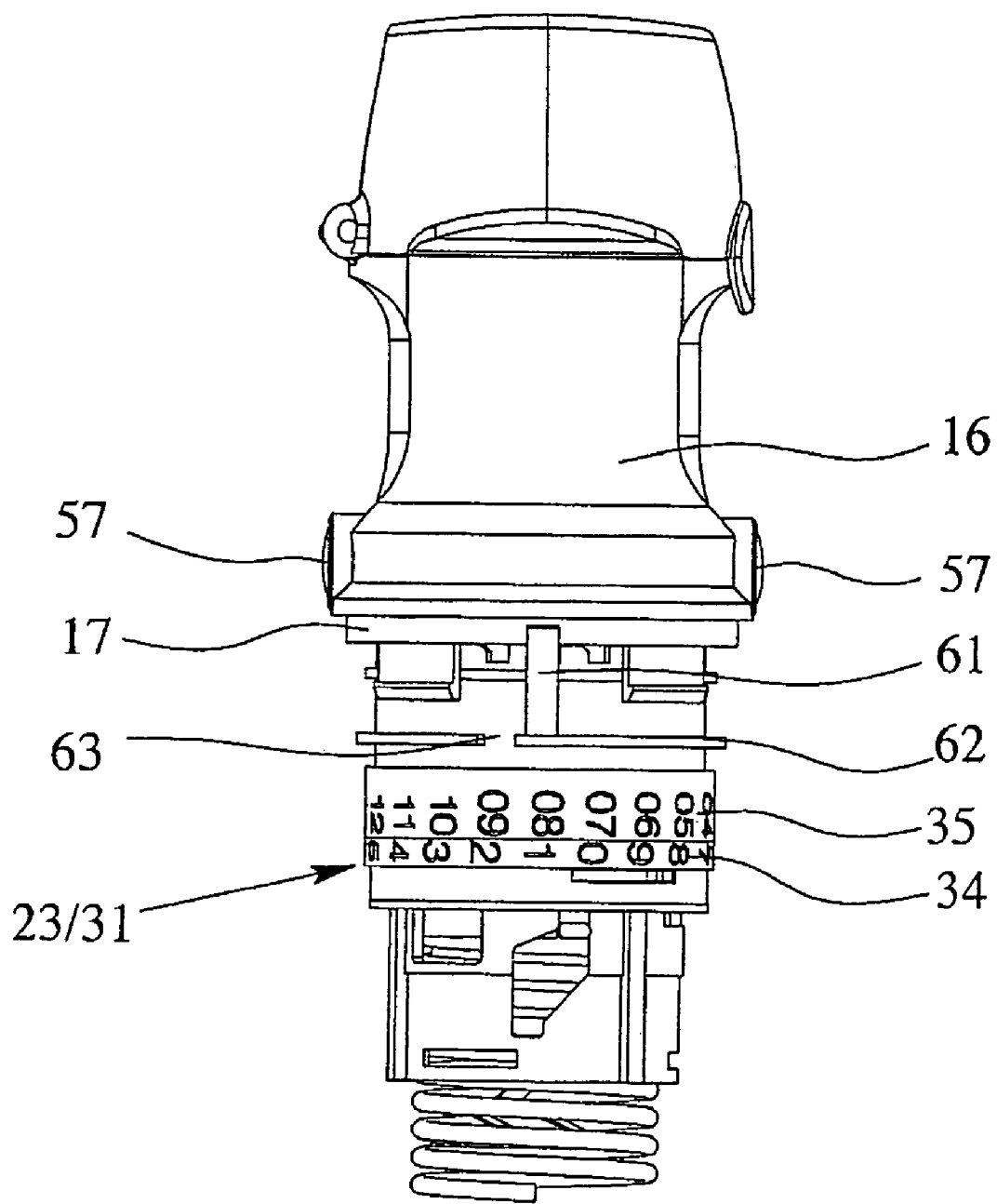
FIG. 25 is a schematic section of a first counter of an atomizer according to a fourth embodiment in the unlocked state.
Figure 26:
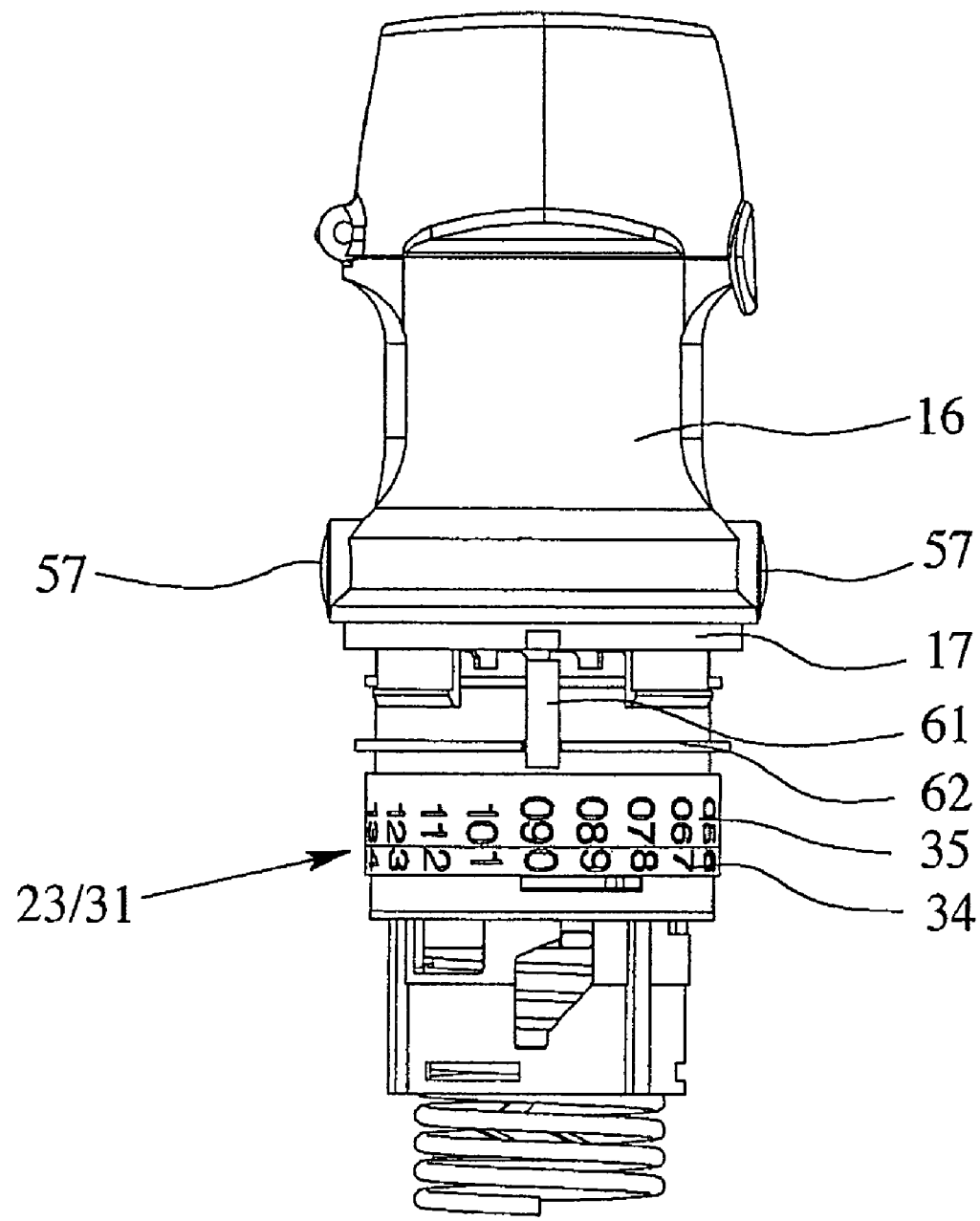
FIG. 26 is a sectional view of the atomizer corresponding to FIG. 25 in the first locked state.

FIGS. 25 & 26 show sections of a proposed atomizer 1 according to a fourth embodiment, wherein the housing part 18 is shown in a see-through manner for illustration purposes.

The fourth embodiment corresponds extensively to the third embodiment, but instead of a blocking of the operation of the locking element 8 in the first locked state, in the fourth embodiment, a blocking of operation preferably takes place by free running of the rotation of the housing part 18 relative to the housing upper part 16 or the housing inner part 17.

In the normal, unlocked state (FIG. 25), the housing part 18 is coupled with the inner part 17 secured against rotation, so that through rotation of the inner part 17 via a gear that has already been mentioned, but is not shown here, the holder 6 can be moved axially against the force of the drive spring 7 and the drive spring 7 can thereby be tensioned. In the fourth embodiment, the rotating coupling is created by means of a coupling element 61, in particular, in the form of a feather key. In the illustration of FIG. 25, in order to create the rotating coupling the coupling element 61 engages axially or at the end in a recess on the inner part 17. The coupling element 61 is preferably guided axially in an axial groove on the housing part 18 in a displaceable manner and coupled with the counter device 23, in particular, the first counter 31 or the second counting ring 35 to determine the axial position.

In the example shown, the counter 31 or the second counting ring 35 has a ring section 62 with a gap 63 assigned to it. In particular, the coupling element 61 is supported axially on the ring section 62 in the engaging state.

Figure 30:
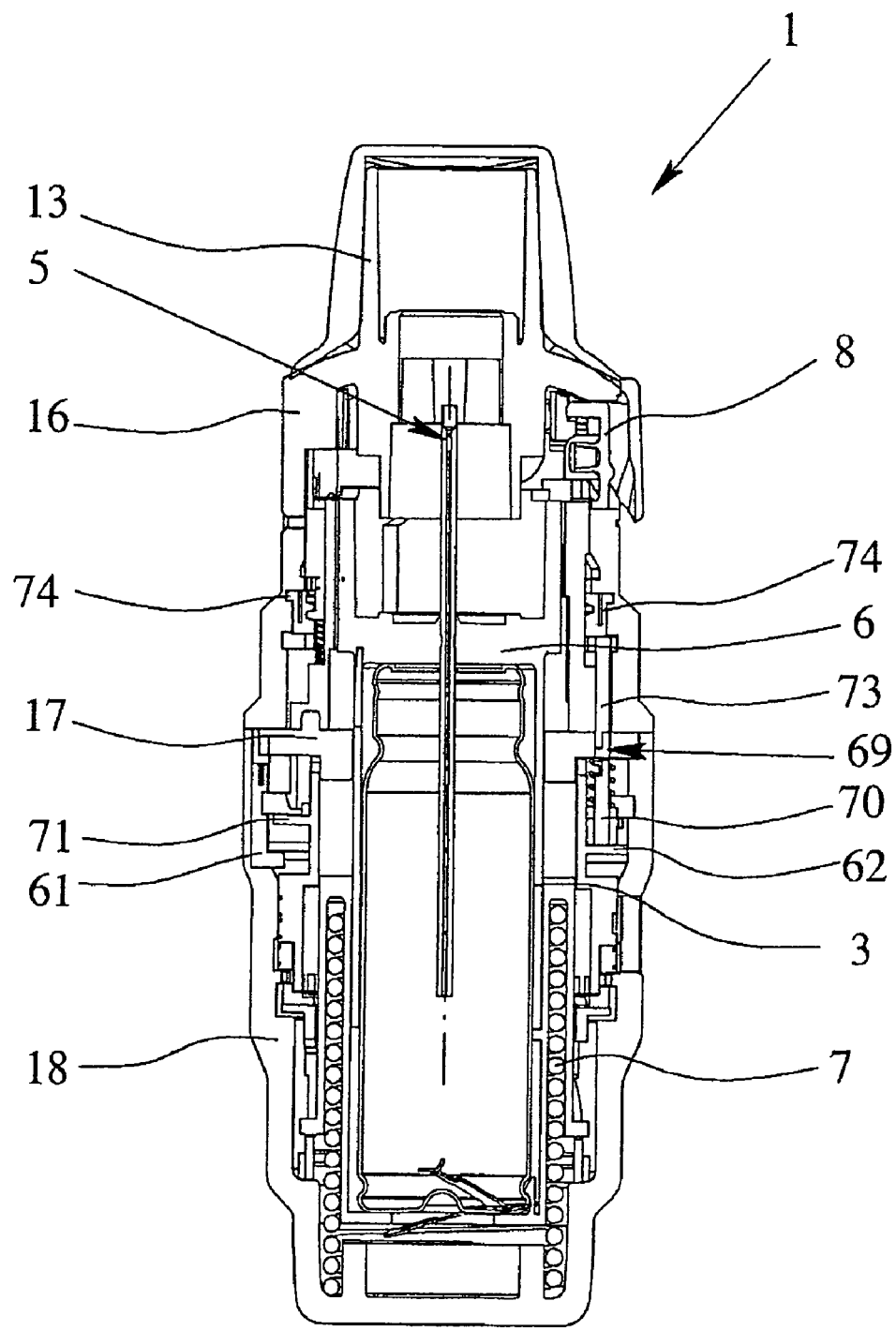
FIG. 30 is a schematic cross-sectional view of the atomizer according to FIG. 29 in the first or second locked state.

When the gap 63 is aligned with the coupling element 61 or the feather key, thus in the first locked state, the coupling element 61 can expand in the axial direction—in particular because of its inherent elasticity—as shown in FIGS. 26 & 30, and thereby release the engagement in the recess in the inner part 17. Thus, the rotating coupling between the housing part 18 (not shown) and the inner part 17 in the first locked state is released in order to lock the atomizer 1 against undesired operation, namely undesired tensioning of the atomizer 1 or the drive spring 7 in the first locked state. Instead of blocking, here, therefore, a release or free running of the rotation of the operational lock takes place.

In the tensioned state, the housing part 18 with the container 3 can be detached from the housing upper part 16 and exchanged for a new housing part 18 with a new container 3. The exchanged first counter 31 is then reset, so that the necessary rotating coupling between the housing part 18 and the inner part 17 is created or recreated and the permitted number of operations of the atomizer 1 or fluid withdrawals from the container 3 can be carried out.

Self-evidently other design solutions for creating the rotating coupling and decoupling in the first locked state or for other free running in the locked state are also possible.

Figure 27A:
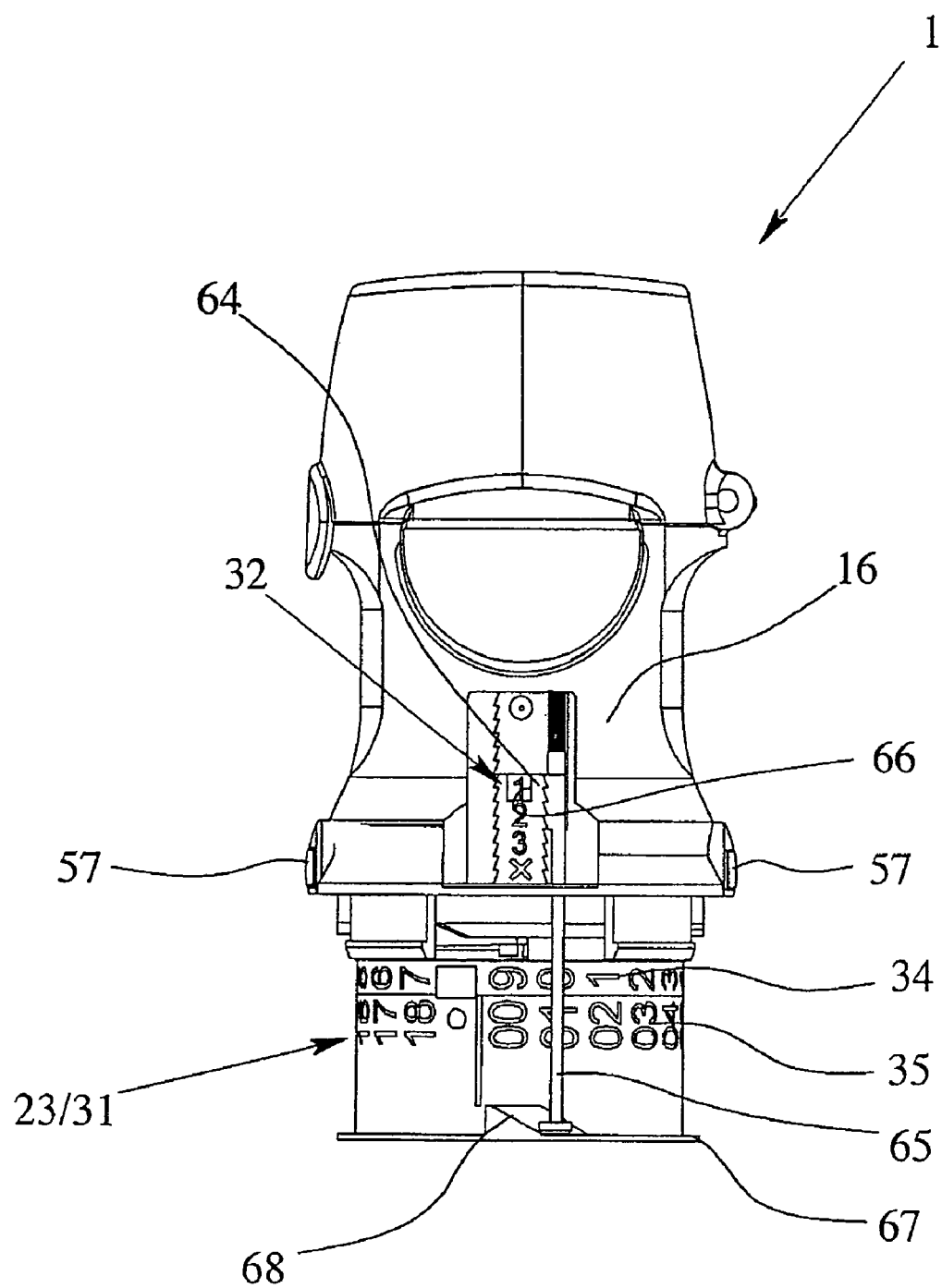
FIGS. 27a-c are schematic views of a counter device with a second counter of the atomizer according to FIG. 25 in various states.
Figure 27B:
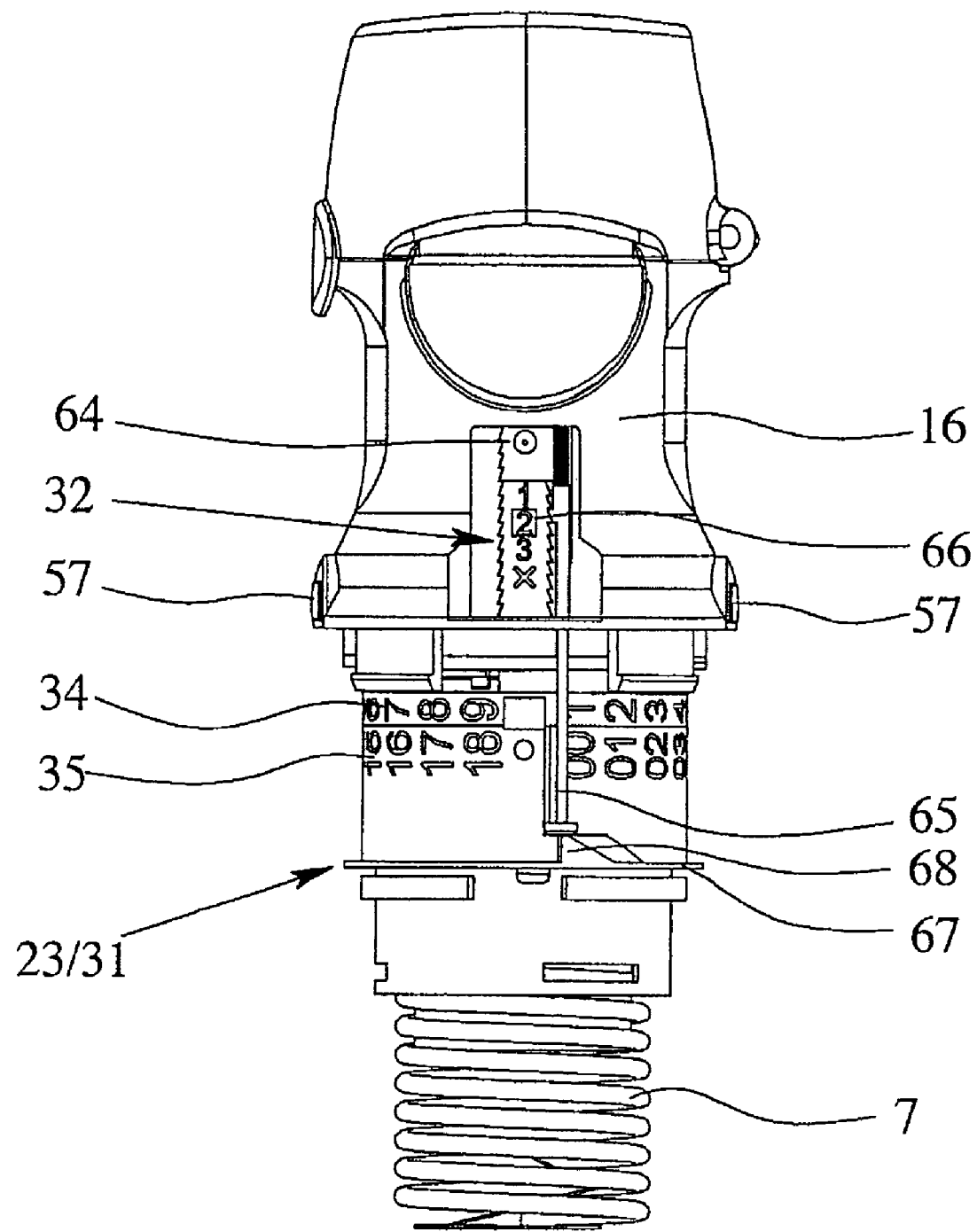
Figure 27C:
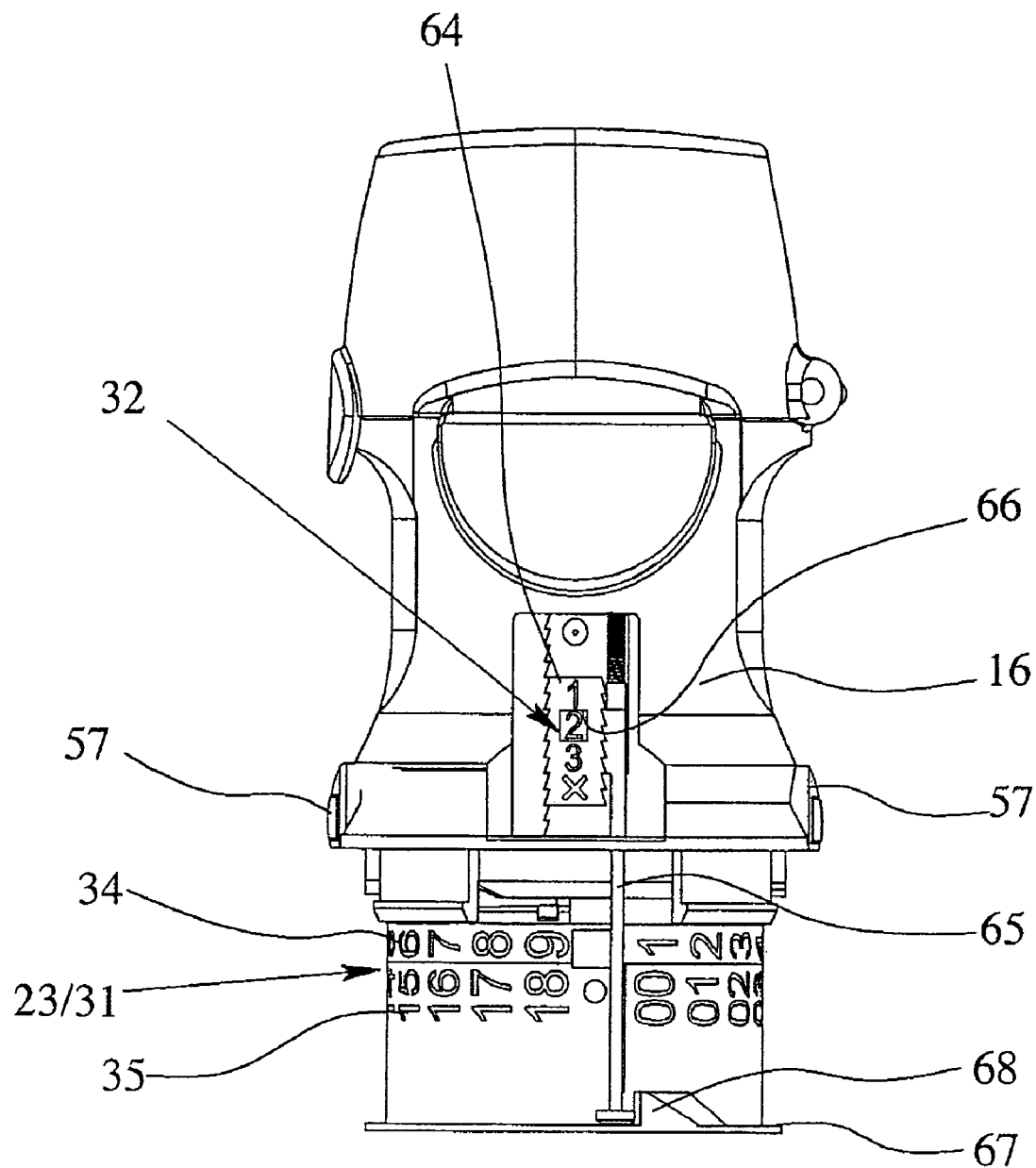

FIGS. 27a to 27c show sections of the fourth embodiment, wherein the housing part 18 is left out for illustration purposes and the housing upper part 16 is shown cut away or in a see-through manner for illustration purposes.

For container counting, the counter device 23 or the second counter 32 in the fifth embodiment has a counter element 64 which, by means of an assigned pin 65 or the like, can be displaced in increments or individual counter steps—preferably in the axial direction. The current counter number is visible to the user through a suitable recess or window 66 in the housing upper part 16. The display of the container number can also be performed through colors, symbols or the like, in particular, rather than numbers.

The second counter 32 in the fourth embodiment is preferably in turn coupled with the first counter 31.

In the example shown, the pin 65 slides on a ring 67 of the first counter 31 or second counting ring 35. FIG. 27a shows an atomizer 1 or the counter device 23 prior to the final permitted operation. After a defined number of permitted operations of the atomizer 1, a ramp 68 on the ring 67 engages below the pin 65 and leads to an axial displacement, as shown in FIG. 27b, wherein the counter element 64 is displaced further by one increment or counter step. Only after the housing part 18 and the first counter 31 have been exchanged does the pin 65 revert to its starting position shown in FIG. 27c, wherein the counter element 64 as a result of latching (not shown) or the like retains its previous counter value and its previous position. Other design solutions are also possible here, however.

Figure 28A:
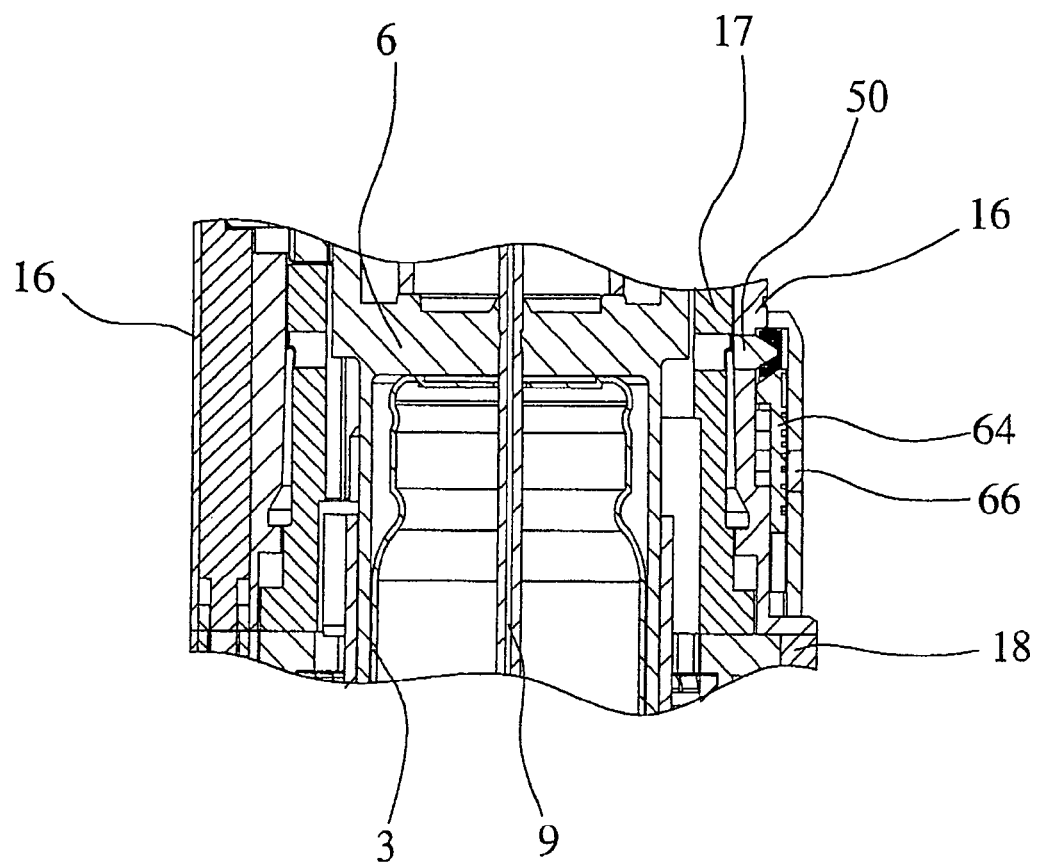
FIGS. 28a & 28b are schematic cross-sectional views of the second counter according to FIG. 27 in the unlocked state and in the second locked state, respectively.
Figure 28B:
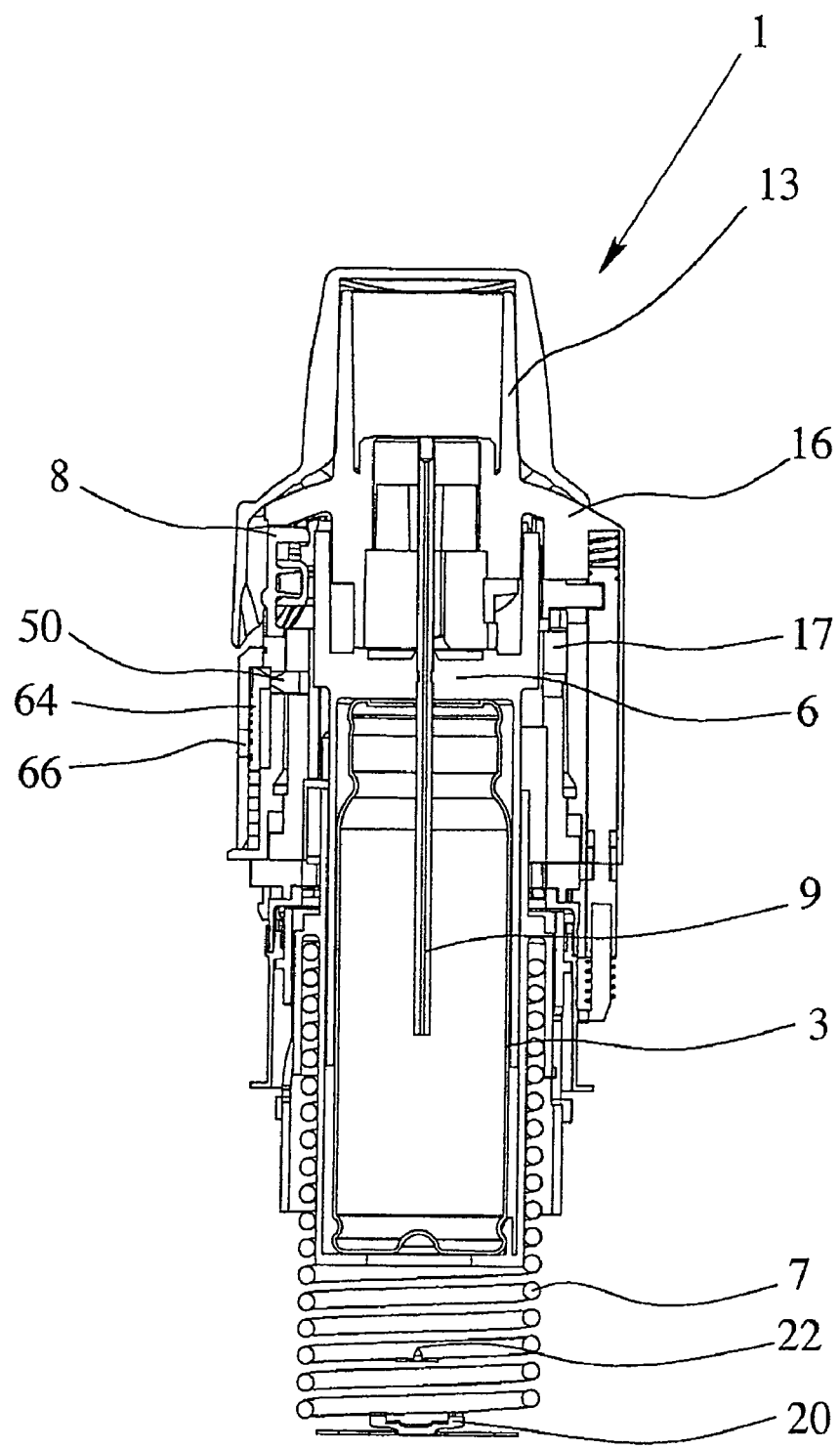

FIGS. 28a & 28b show schematic representations of the preferred design of the locking of the atomizer 1 in the second locked state.

FIG. 28a shows the not yet locked state. The counter element 64 is still not engaged or is distanced from a preferably radially displaceable blocking element 50.

If the second locked state is reached, thus, in particular, if a certain number of used containers 3, and if necessary, also a certain number of operations of the atomizer 1 with the current container 3 have been reached or exceeded, the counter element 64 is further displaced axially by the pin 65—in the representation of FIGS. 28a & 28b, upwards—and the blocking element 50 is thereby brought into the locking position. In particular, the blocking element 50, because of a corresponding sliding slope, is displaced radially—in particular, inwards—and a rotation of the inner part 17 relative to the housing upper part 16 is blocked by a corresponding engagement. The blocking element 50 serves here as a locking bolt. In this way, the atomizer 1 is locked against further tensioning. This locking is preferably no longer reversible. The entire atomizer 1 must then be exchanged.

In the third and fourth embodiments, the diving of the counter device 23, in particular, the first counter 31, if necessary, also directly by the rotation of the housing part 18 relative to the inner part 17 or the sleeve-like extension of the holder 6, can take place via a corresponding engagement or the like.

Figure 29:
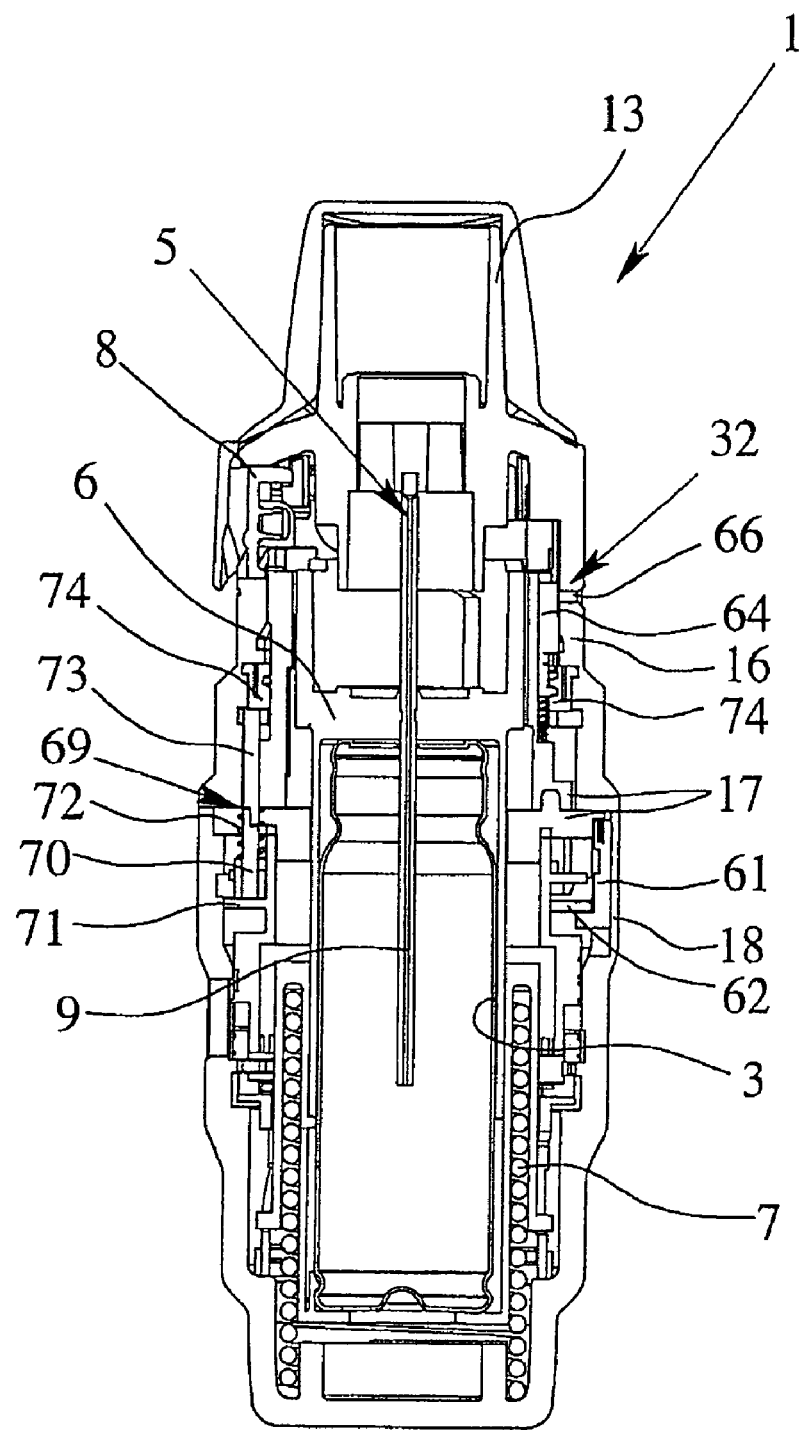
FIG. 29 is a schematic cross-sectional view of a section of an atomizer according to a fifth embodiment in the unlocked state.

FIG. 29 shows a partial cross-section of a proposed atomizer 1 according to a fifth embodiment in the unlocked state; FIG. 30 shows the atomizer 1 in the first or second locked state.

The second counter 32 is coupled via a coupling 69, in particular, a claw coupling, with the first counter 31. FIG. 29 shows the coupled state. In the example shown, a bottom shaft 70 that can be driven by the first counter 31 is supported axially by a ring section 71 against the force of a spring 72, so that the shaft 70, via the coupling 69, engages with the second counter 32 in a driving fashion, in particular, with an upper shaft 73 of the second counter 32 which, for its part, rotates a drive ring 74 in the housing upper part 16.

The drive ring 74 can serve as a counting ring of the second counter 32. Preferably, however, via an internal or external thread, it drives the counter element 64 in an axial direction, so that the axial position of the counter element 64 indicates the counter value—in particular, also in the form of a color coding, symbols or the like—of the second counter 32, which is visible through the window 66.

Further, FIG. 29 shows the coupling element 61 according to the fourth embodiment for rotating coupling, as it connects the housing part 18 with the inner part 17 in a manner secured against rotation and is axially supported by the ring section 62.

In the first or second locked state (FIG. 30), the coupling 69 is opened, and thus, the driving connection between the first counter 31 and the second counter 32 is interrupted. Further, the rotating coupling between the housing part 18 and the inner part 17 is released. This is achieved by corresponding gaps in the rotating ring sections 62, 71 which, in the first or second locked states, align with the coupling element 61 or the shaft 70, so that the coupling element can release the axial engagement in a recess in the inner part 17 and the shaft 70 through the force of the spring 72 can retract axially from the countershaft 73 and thereby open the coupling 69.

In the said state, the housing part 18 with the container 3 and the first counter 31 can be exchanged (in the case of the first locked state), wherein the driving connection between the first counter 311 and the second counter 32 is then recreated, the coupling is thus closed again and the rotating connection is again created via the coupling element 61 between the housing part 18 and the inner part 17, so that the tensioning or operational lock is released.

It is obvious that other design solutions for creating the explained or the like functions are possible.

In the following, using FIGS. 31 to 33, a sixth embodiment of the proposed atomizer 1 is explained with particular essential differences as compared with the previous embodiments being emphasized. Therefore, the statements made previously apply accordingly or in addition.

In the sixth embodiment, in the first and/or second locked state, operational looking and preferably also rotational locking are envisaged. For optional rotational locking, in the example shown, the counter device 23 or its second counter 32 operates the blocking element 50 which, in particular, takes the form of a retaining spring.

The threaded spindle 48 of the counter device 23 or of the second counter 32, in the example shown, is provided with an in particular toothed wheel- or pinion-shaped engagement section 75, which can be driven by assigned projections, cams, noses or the like (not shown), which are formed on the inside of the housing upper part 16, and which, accordingly, can be moved relative to the inner part 17 along a circumference or in an axial plane 76, for turning the threaded spindle 48. The rotation of the inner part 17 relative to the housing upper part which, in particular, for tensioning the atomizer 1 or pressurizer 5—in the example shown, preferably, in 180° steps—always takes place in the same direction of rotation, and therefore, leads to a corresponding rotation of the threaded spindle 48, and thus, to a corresponding axial movement of the rider 49.

Figure 31:
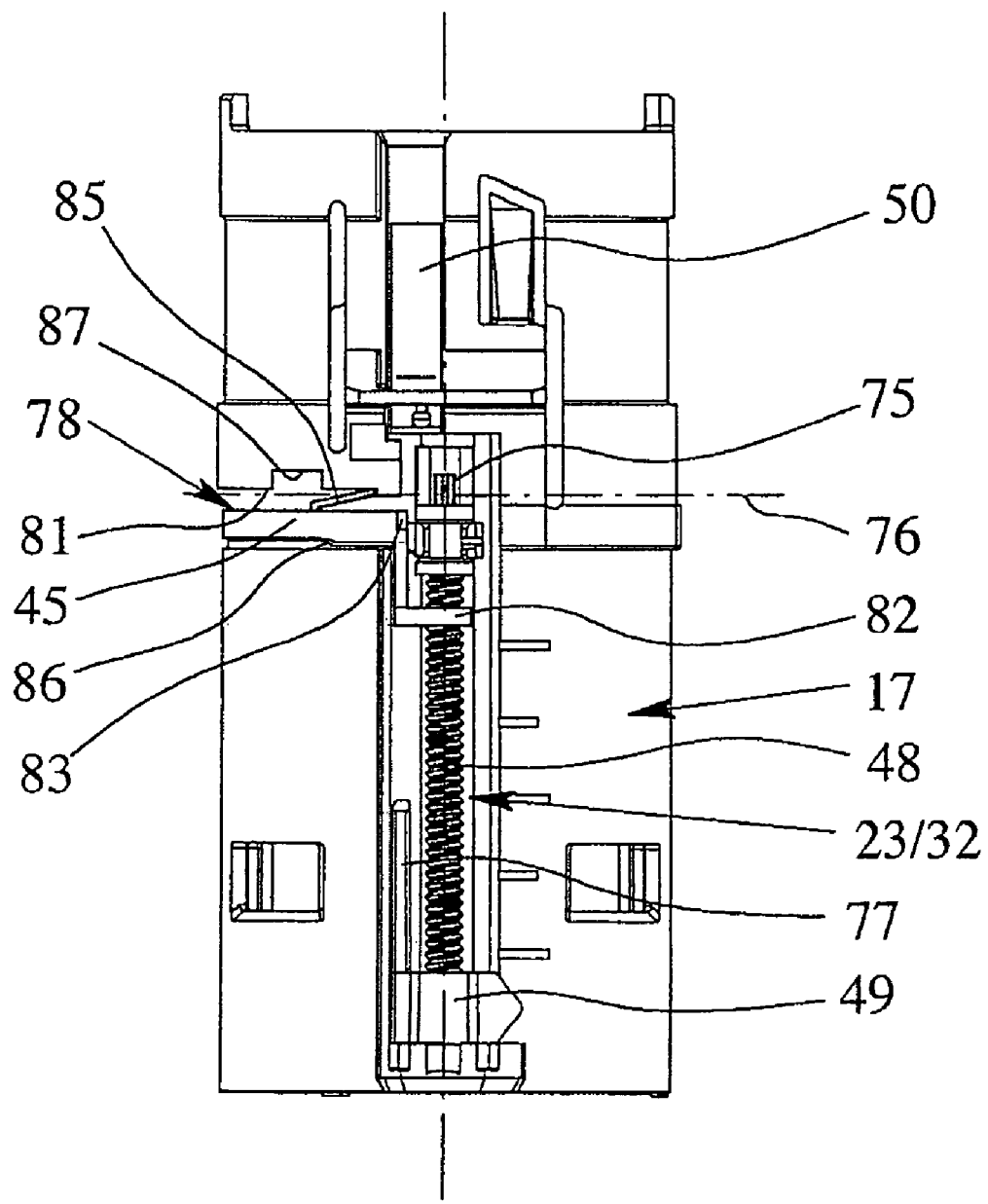
FIG. 31 is a schematic view of part of an atomizer according to a sixth embodiment in the unlocked state.

In particular, when a corresponding number of permitted operations and/or containers 3 has been reached, the rider 49—for example, by means of a finger 77 or the like—can displace the blocking element 50 from the position shown in FIG. 31 upwards so that a radial rebound of a leg of the blocking element 50 takes place. The leg can then engage in a corresponding recess, groove or the like of the housing upper part 16 and thereby block any (further) rotation of the inner part 17 relative to the atomizer 1, and thus, to the housing upper part 16. In this way, rotational or atomizer locking is achieved, as has already been explained using FIGS. 15 to 17. Other designs are, however, also possible.

In the sixth embodiment, the atomizer 1 has a locking device 78 for operational locking which, with particular preference, is designed as a forcibly controlled sliding mechanism, as explained in more detail further on. In particular, the locking device 78, in the first and/or in the second locked state, locks the locking element 8 of the atomizer 1 which must be operated to trigger delivery and/or atomization of fluid 2.

In the example shown, the locking device 78 has the lock part 41, the axis of which can, in particular, can be moved in parallel to the longitudinal, rotational or movement axis of the atomizer 1, and the assigned control part 45, the axis of which can, in particular, be moved peripherally in relation to the longitudinal, rotational or movement axis of the atomizer 1. The lock part 41 has cranked or forcible movement, here by the control part 45, as indicated in FIG. 32. In the locked state, the lock part 41 engages between the locking element 8 and the housing upper part 16, as indicated in the schematic section according to FIG. 33. In particular, the circular shaped locking element 8 is, in this locked state, displaced radially relative to the holder 6, as a result of which the holder 6 is locked against an outwardly directed movement in FIG. 33 for delivering the fluid 2 and pressurization or atomization. The locking element 8, which is preferably provided with a release key on the side opposite the locking or the lock part 41, is unable to be displaced radially in this locked stated to trigger the pressurization or atomization and is, therefore, blocked.

Figure 33:
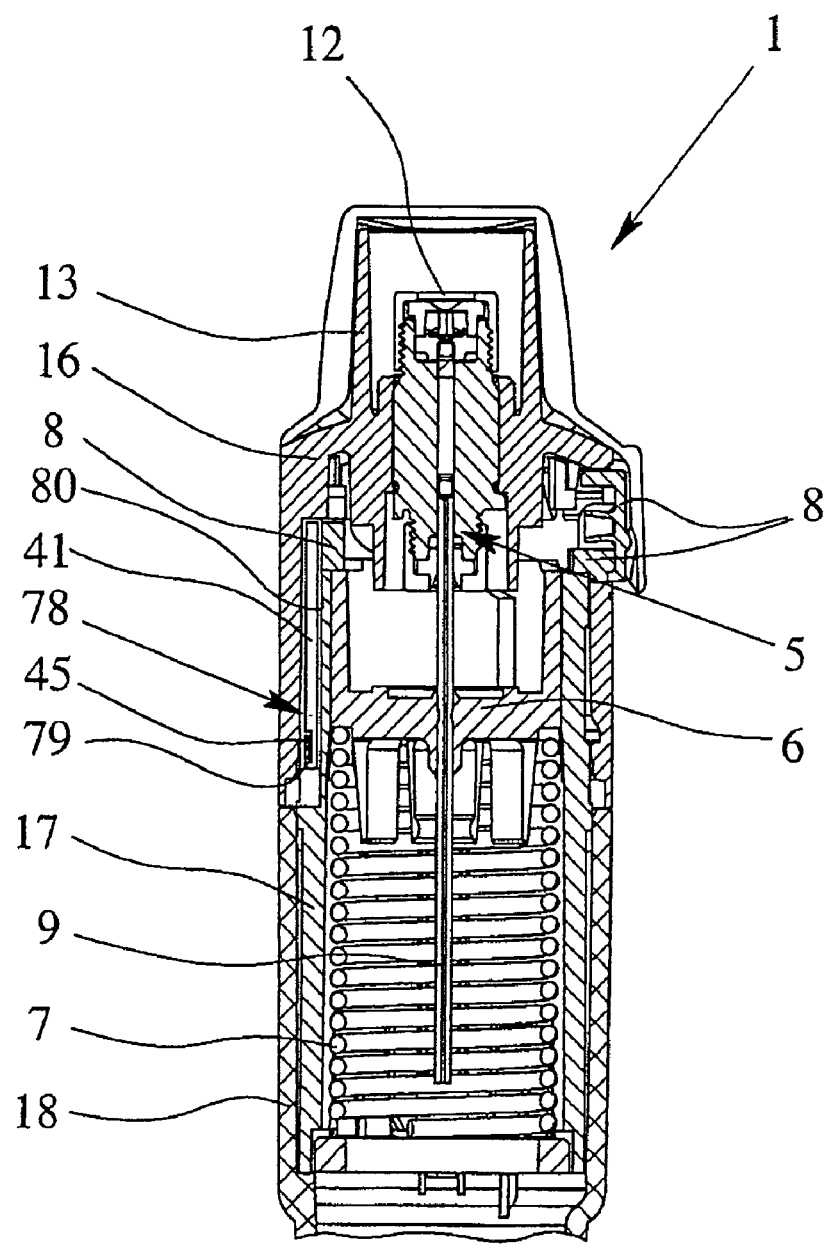
FIG. 33 is a schematic cross-sectional view of the atomizer according to FIG. 31 in the first or second locked state.

FIG. 33 also shows the cranked or forcible guidance by the control part 45, which preferably engages diagonally to the direction of displacement or movement of the lock part 41 in a recess 79 of the lock part 41.

Figure 32:
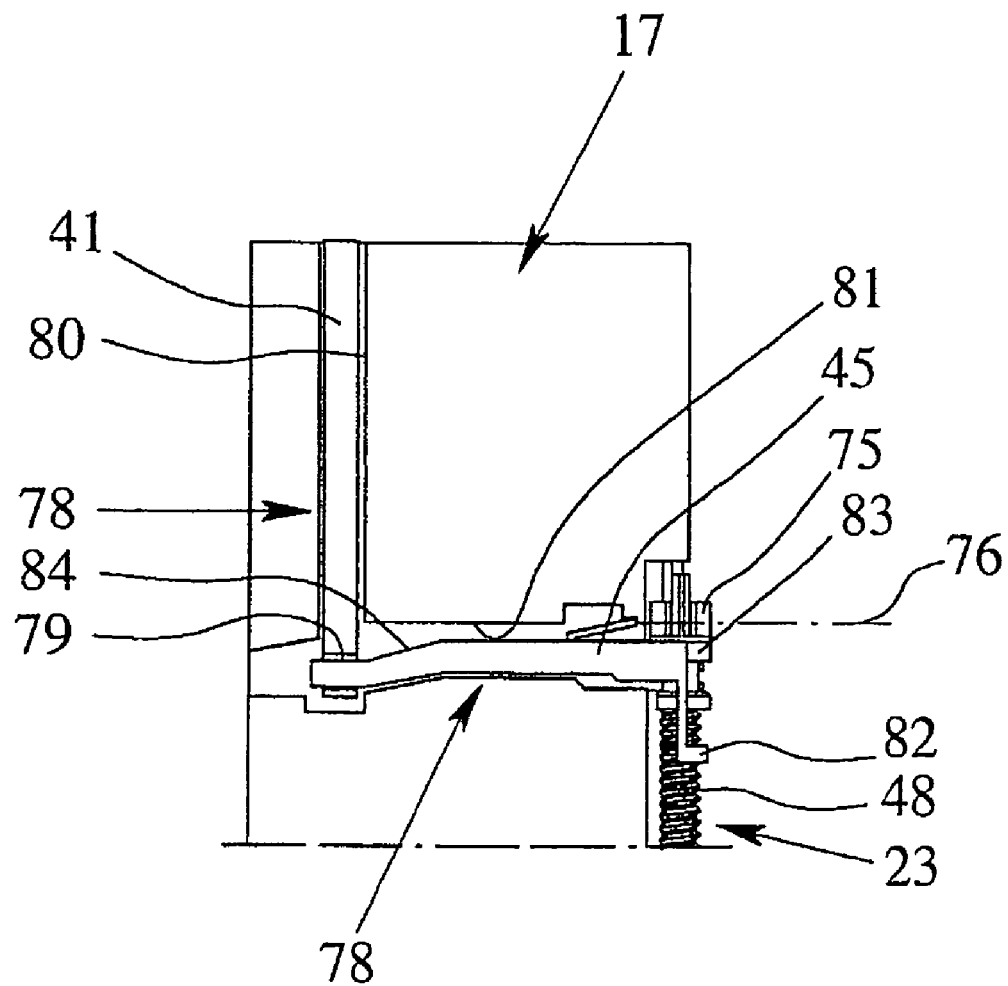
FIG. 32 is a further view of a portion of the atomizer shown in FIG. 31.

FIG. 32 shows a schematic representation of the locking device 78 in the locked state. The lock part 41 is preferably guided in a displaceable manner in a recess or groove 80 formed in the inner part 17 and running parallel to the axis or longitudinally. In particular, the arch-shaped control part 45 is, for its part, guided in a peripherally running recess or groove 81, preferably also formed on the inner part 17, so that it is essentially peripherally moveable or displaceable, more details of which are provided below.

The control part 45 has an arm 82 which extends into the area of movement of the rider 49, as shown in FIGS. 31 and 32. The control part 45 also has a radial stop or projection 83. In the unlocked state shown in FIGS. 31 & 32, the outside arm 82 of the control part 45 is, in particular, in its lower position so that the projection 83 is positioned outside of the movement path or plane 76.

Shortly before arriving at its upper end position shown in the illustrations, the rider 49 engages with the arm 82 and displaces the control element 45 diagonally to its preferably peripheral direction of operation, in the example shown, essentially in the axial direction or upwards. This pushes the projection 83 into the running path or plane 77, so that with the further or next rotation of the inner part 17 relative to the housing upper part 16, the projections, cams, noses or the like (not shown) on the housing upper part engage with the projection 83 and are able to displace these together with the control part 45—in the example shown essentially in the circumferential direction—in FIGS. 31 & 32 to the right—relative to the inner part 17 in the assigned recess or groove 81. This preferably peripheral movement or displacement leads via an inclined plane 84 formed on the control part 45 or another suitable geared connection to the desired locking movement of the lock part 41, here therefore to a displacement of the lock part 41 that is, at least essentially parallel to the axis (in FIG. 32 upwards). This sequence of movements is coupled with the, in particular, radial disengagement of the lock element 8 for blocking the holder 6 in the tensioned state in such a way that the lock part 41 engages in this radially disengaged state between the lock element 8 and the housing upper part 16 or another suitable part, in order to achieve the desired locking of operation or triggering.

The control part 45, in its lower axial position, as shown in FIGS. 31 & 32, is preferably pre-tensioned in an elastic manner, and for this purpose has, for example, the spring arm 85 shown in FIG. 31. The rider 49 can then displace the control part 45 with the radial projection 82, axially, in FIG. 31 upwards, against the force of this spring arm 85.

The pre-tensioning of the control part 45 in the lower axial position serves to prevent an undesired axial and/or peripheral displacement of the control part 45, before the predefined number of containers or operations has been reached.

In order to secure the control part 45 in the lower axial position, a shoulder 86 can be provided which can only be overcome in the upper axial position. Only then can the peripheral movement or displacement of the control part 45 take place.

With the peripheral movement of the control part 45, the recess or groove 80 along with the recess 79 in the lock part 41, in particular, form guides such that the lock part 41 is forcibly and in a defined manner—in particular, in a cranked manner—moved axially upwards into the lock position.

The operational lock, like the optional rotational lock, preferably can no longer be reversed, and thus, leads to an irreversible locking of the atomizer. In order to guarantee this, in the example shown, the lock part 41 can be blocked in the lock position. This takes place by blocking the control part 45 in the position in which it retains the lock part 41 in the lock position, in particular, by engagement of the spring arm 85 in a corresponding recess 87 or the like. The first and/or second lock state, depending on the design of the atomizer 1, cannot be reversed.

It should generally be mentioned that, with the proposed atomizer 1, the container 3 is preferably insertable, and thus, can be incorporated into the atomizer 1. Accordingly, the container 3 is preferably a separate component. However, the container 3 can basically also be foraged directly by the atomizer 1 or a component of the atomizer 1 or be otherwise integrated into the atomizer 1.

As already mentioned individual features, aspects and/or principles of the embodiment described can also be combined with each other as desired and in particular can be used with the known atomizer according to FIGS. 1 & 2, but also with similar or other atomizers, dispenses or the like.

Unlike pedestal-mounted devices or the like, the proposed atomizer 1 is preferably designed to be transportable, in particular, it is a mobile manual device.

The proposed solution can not only be used in the atomizer 1 described here in detail but also in other atomizers or inhalers, such as powder inhalers or so-called metered dose inhalers.

The fluid 2 is preferably a liquid, as already mentioned, in particular, an aqueous drug formulation. However, another drug formulation, such as a suspension or the like may also be involved.

According to a design variant, the fluid 2 can also comprise particles or powder. In this case, in place of the discharge nozzle 12, another delivery device, in particular, a discharge opening (not shown) or a feed channel (not shown), for delivering the fluid 2 or powder or the like into the mouthpiece 13 can be provided. The optional air vent 15 is then used for the preferably parallel feeding of ambient air, in order to generate or allow an air flow of sufficient volume for breathing in or inhalation in the mouthpiece 13.

If necessary the fluid 2 can also be atomized by means of a propellant gas.

In the following, preferred components and/or formulations of the preferably medicinal fluid 2 are listed. As already mentioned these may be aqueous, or non-aqueous solutions, mixtures, ethanol-containing or solvent-free formulations or the like. Preferably the fluid 2 may contain or comprise or consist of:

As pharmaceutically active substances, substance formulations or substance mixtures inhalable compounds are used, such as inhalable macromolecules, as disclosed in EP 1 003 478. Preferably, substances, substance formulations or substances mixtures for the treatment of respiratory tract diseases are used which have applications in the inhalational field.

Particularly preferred in this context are pharmaceutical compositions selected from among the anticholinergics, betamimetics, steroids, phosphodiesterase IV inhibitors, LTD4-antagonists and EGFR-kinase inhibitors, antiallergics, ergot alkaloid derivatives, triptanes, CGRP antagonists, phosphodiesterase-V inhibitors, and combinations of active substances of this kind, e.g. betamimetics plus anticholinergics or betamimetics plus antiallergics. In the case of combinations, at least one of the active substances preferably contains chemically bound water. Anticholinergic-containing active substances are preferably used, as monopreparations or in the form of combined preparations.

The fluid or formulation according to the invention might contain (additional) pharmacologically active substances or mixtures of substances, preferably selected from those groups:

Anticholinergica:

Anticholinergica preferably selected from the group consisting of tiotropium, tiotropiumbromide, oxitropiumbromide, flutropiumbromide, ipratropiumbromide, gly-copyrroniumsalts, trospiumchloride, tolterodin, 2,2-diphenylpropionacidtropenolester-methobromide, 2,2-diphenylpropionacidscopinester-methobromide, 2-fluoro-2,2-diphenylacidicacidscopinester-methobromide, 2-fluoro-2,2-diphenylacidicacidtropenolester-methobromide, 3,3',4,4'-tetrafluorbenzilacidtropenolester-methobromide, 3,3',4,4'-tetrafluorbenzilacidscopinester-methobromide, 4,4'-difluorbenzilacidtropenolester-methobromide, 4,4'-difluorbenzilacidscopinester-methobromide, 3,3'-difluorobenzilacidtropenolester-methobromide, 3,3'-difluorobenzilacidscopinester-methobromide, 9-hydroxy-fluoren-9-carbonacidtropenolester-methobromide, 9-fluoro-fluoren-9-carbonacidtropenolester-methobromide, 9-hydroxy-fluoren-9-carbonacidscopinester-methobromide, 9-fluoro-fluoren-9-carbonacidscopinester-methobromide, 9-methyl-fluoren-9-carbonacidtropenoleste-methobromide, 9-methyl-fluoren-9-carbonacidscopineste-methobromide, benzilacidcyclopropyltropinester-methobromide, 2,2-diphenylpropion-acidcyclopropyltropinester-methobromide, 9-hydroxy-xanthen-9-carbonacidcyclopropyltropinester-methobromide, 9-methyl-fluoren-9-carbonacidcyclopropyl-tropinester-methobromide, 9-methyl-xanthen-9-carbonacidcyclopropyltropinester methobromide, 9-hydroxy-fluoren-9-carbonacidcyclopropyltropinester-methobromide, 4,4'-difluorbenzilacidmethylestercyclopropyltropinester-methobromide, 9-hydroxy-xanthen-9-carbonacidtropenolester-methobromide, 9-hydroxy-xanthen-9-carbonacidscopinester methobromide, 9-methyl-xanthen-9-carbonacidtropenolester-methobromide, 9-methyl-xanthen-9-carbonacidscopinester-methobromide, 9-methyl-xanthen-9-carbonacidtropenolester methobromide, 9-difluormethyl-xanthen-9-carbonacidtropenolester-methobromide, 9-hydroxymethyl-xanthen-9-carbonacid-scopinester methobromide, optionally in the form of the racemates, the enantiomers, the diastereomers and optionally the pharmacologically acceptable acid addition salts, solvates and/or the hydrates thereof.

Beta-Sympathomimetica:

Beta-sympathomimetica preferably selected from the group consisting of albuterol, bambuterol, bitolterol, broxaterol, carbuterol, clenbuterol, fenoterol, formoterol, hexoprenaline, ibuterol, indacaterol, isoetharine, isoprenaline, levosalbutamol, mabuterol, meluadrine, metaproterenol, orciprenaline, pirbuterol, procaterol, reproterol, rimiterol, ritodrine, salmeterol, salmefamol, soterenot, sulphonterol, tiaramide, terbutaline, tolubuterol, CHF-1035, HOKU-81, KUL-1248, 3-(4-{6-[2-hydroxy-2-(4-hydroxy-3-hydroxymethyl-phenyl)-ethylamino]-hexyloxy}-butyl)-benzenesulfoneamide, 5-[2-(5,6-Diethyl-indan-2-ylamino)-1-hydroxy-ethyl]-8-hydroxy-1H-quinolin-2-one, 4-hydroxy-7-[2-{[2-{[3-(2-phenylethoxy)propyl]sulphonyl}ethyl]-amino}ethyl]-2(3H)-benzothiazolone, 1-(2-fluoro-4-hydroxyphenyl)-2-[4-(1-benzimidazolyl)-2-methyl-2-butylamino]ethanol, 1-[3-(4-methoxybenzyl-amino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propy-lamino]ethanol, 1-[2H-5-hydroxy-3-oxo-4H-1,4-benzoxazin-8-yl]-2-{4-[3-(4-methoxy-phenyl)-1,2,4-triazol-3-yl]-2-methyl-2-butylamino}ethanol, 5-hydroxy-8-(1-hydroxy-2-isopropylaminobutyl)-2H-1,4-benzoxazin-3-(4H)-one, 1-(4-amino-3-chloro-5-trifluoromethylphenyl)-2-tert.-butylamino)ethanol and 1-(4-ethoxycarbonylamino-3-cyano-5-fluorophenyl)-2-(tert.-butylamino)ethanol, optionally in the form of the racemates, the enantiomers, the diastereomers and optionally the pharmacologically acceptable acid addition salts, solvates and/or the hydrates thereof.

Steroids:

Steroids preferably selected from the group consisting of prednisolone, prednisone, butixocortpropionate, RPR-106541, flunisolide, beclomethasone, triamcinolone, budesonide, fluticasone, mometasone, ciclesonide, rofleponide, ST-126, dexamethasone, 6α,9α-difluoro-17α-[(2-furanylcarbonyl)oxy]-11β-hydroxy-16α-methyl-3-oxo-androsta-1,4-dien-17β-carbothionacid (S)-fluoromethylester, 6α,9α-difluoro-11β-hydroxy-16α-methyl-3-oxo-17α-propionyloxy-androsta-1,4-dien-17β-carbothionacid (S)-(2-oxo-tetrahydro-furan-3S-yl)ester and etiprednol-dichloroacetat (BNP-166), optionally in the form of the racemates, the enantiomers, the diastereomers and optionally the pharmacologically acceptable acid addition salts, solvates and/or the hydrates thereof.

PDEIV-Inhibitors:

PDE IV-inhibitor preferably selected from the group consisting of enprofyllin, theophyllin, roflumilast, ariflo (cilomilast), CP-325,366, BY343, D-4396 (Sch-351591), AWD-12-281 (GW-842470), N-(3,5-Dichloro-1-oxo-pyridin-4-yl)-4-difluoromethoxy-3-cyclopropylmethoxybenzamide, NCS-613, pumafentine, (−)p-[(4aR*, 10bS*)-9-ethoxy-1,2,3,4,4a,10b-hexahydro-8-methoxy-2-methylbenzo[s][1,6]

naphthyridin-6-yl]-N,N-diisopropylbenzamide, (R)-(+)-1-(4-bromobenzyl)-4-[(3-cyclopentyloxy)-4-methoxyphenyl]-2-pyrrolidone, 3-(cyclopentyloxy-4-methoxyphenyl)-1-(4-N'-[N-2-cyano-S-methyl-iso-thioureido]benzyl)-2-pyrolidone, cis[4-cyano-4-(3-cyclopentyloxy-4-methoxyphenyl)cyclohexan-1-carbonacid], 2-carbomethoxy-4-cyano-4-(3-cyclopropylmethoxy-4-difluoromethoxyphenyl)cyclohexane-1-on, cis[4-cyano-4-(3-cyclopropylmethoxy-4-difluoromethoxyphenyl)cyclohexane-1-ol], (R)-(+)-ethyl[4-(3-cyclopentyloxy-4-methoxyphenyl)pyrrolidin-2-yliden]acetate, (S)-(−)-ethyl[4-(3-cyclopentyloxy-4-methoxyphenyl)pyrrolidin-2-yliden]acetate, CDP840, Bay-198004, D-4418, PD-168787, T-440, T-2585, arofyllin, atizoram, V-11294A, C1-1018, CDC-801, CDC-3052, D-22888, YM-58997, Z-15370, 9-cyclopentyl-5,6-dihydro-7-ethyl-3-(2-thienyl)-9H-pyrazolo[3,4-c]-1,2,4-triazolo[4,3-a]pyridin and 9-cyclopentyl-5,6-dihydro-7-ethyl-3-(tert-butyl)-9H-pyrazolo[3,4-c]-1,2,4-triazolo[4,3-a]pyridine, optionally in the form of the racemates, the enantiomers, the diastereomers and optionally the pharmacologically acceptable acid addition salts, solvates and/or the hydrates thereof.

LTD4-Antagonists:

LTD4-antagonist preferably selected from the group consisting of montelukast, 1-(((R)-(3-(2-(6,7-difluoro-2-quinolinyl)ethyenyl)phenyl)-3-(2-(2-hydroxy-2-propyl)phenyl)thio)methylcyclopropan-acidicacid, 1-(((1 R)-3-(2-(2,3-dichlorothieno[3,2-b]pyridin-5-yl)-(E)-ethenyl)phenyl)-3-(2-(1-hydroxy-1-methyl-ethyl)phenyl)propyl)thio)methyl)cyclopropanacidicacid, pranlukast, zafirlukast, [2-[[2-(4-tert-butyl-2-thiazolyl)-5-benzofuranyl]oxymethyl]phenyl]acidicacid, MCC-847 (ZD-3523), MN-001, MEN-91507 (LM-1507), VUF-5078, VUF-K-8707 and L-733321, optionally in the form of the racemates, the enantiomers, the diastereomers and optionally the pharmacologically acceptable acid addition salts, solvates and/or the hydrates thereof.

EGFR-Kinase-Inhibitors:

cetuximab, trastuzumab, ABX-EGF, Mab ICR-62, 4-[(3-Chlor-4-fluorophenyl)amino]-6-{[4-(morpholin-4-yl)-1-oxo-2-buten-1-yl]amino}-7-cyclopropylmethoxy-chinazolin, 4-[(R)-(1-phenyl-ethyl)amino]-6-{[4-(morpholin-4-yl)-1-oxo-2-buten-1-yl]-amino}-7-cyclopentyloxy-chinazolin, 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofurane-3-yl)oxy]-chinazoline, 4-[(3-chloro-4-fluoro-phenyl)amino]-6-[2-((S)-6-methyl-2-oxo-morpholine-4-yl)-ethoxy]-7-methoxy-chinazolin, 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-chinazoline, 4-[(R)-(1-Phenyl-ethyl)amino]-6-({4-[N-(tetrahydropyrane-4-yl)-N-methyl-amino]-1-oxo-2-buten-1-yl}amino)-7-cyclopropylmethoxy-chinazoline, 4-[(3-chloro-4-fluorophenyl)amino]-6-({4-[N-(2-methoxy-ethyl)-N-methyl-amino]-1-oxo-2-buten-1-yl}amino)-7-cyclopentyloxy-chinazoline, 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-chinazolin, 4-[(3-Ethinyl-phenyl)amino]-6,7-bis-(2-methoxy-ethoxy)-chinazoline, 4-[(R)-(1-phenyl-ethyl)amino]-6-(4-hydroxy-phenyl)-7H-pyrrolo[2,3-d]pyrimidine, 3-cyano-4-[(3-chloro-4-fluorophenyl)amino]-6-{[4-(N,N-dimethylamino)-1-oxo-2-buten-1-yl]amino}-7-ethoxy-chinoline, 4-[(R)-(1-phenyl-ethyl)amino]-6-{[4-((R)-6-methyl-2-oxo-morpholin-4-yl)-1-oxo-2-buten-1-yl]amino}-7-methoxy-chinazoline, 4-[(3-chloro-4-fluorophenyl)amino]-6-{[4-(morpholine-4-yl)-1-oxo-2-buten-1-yl]amino}-7-[(tetrahydrofurane-2-yl)methoxy]-chinazoline, 4-[(3-ethinyl-phenyl)amino]-6-{[4-(5,5-dimethyl-2-oxo-morpholin-4-yl)-1-oxo-2-buten-1-yl]amino}-chinazoline, 4-[(3-chloro-4-fluoro-phenyl)amino]-6-{2-[4-(2-oxo-morpholine-4-yl)-piperidine-1-yl]-ethoxy}-7-methoxy-chinazoline, 4-[(3-chloro-4-fluoro-phenyl)amino]-6-(trans-4-amino-cyclohexan-1-yloxy)-7-methoxy-chinazoline, 4-[(3-chloro-4-fluoro-phenyl)amino]-6-(trans-4-methanesulfonylamino-cyclohexan-1-yloxy)-7-methoxy-chinazoline, 4-[(3-chloro-4-fluoro-phenyl)amino]-6-(tetrahydropyrane-3-yloxy)-7-methoxy-chinazoline, 4-[(3-chloro-4-fluoro-phenyl)amino]-6-{1-[(morpholine-4-yl)carbonyl]-piperidin-4-yloxy}-7-methoxy-chinazoline, 4-[(3-chloro-4-fluoro-phenyl)amino]-6-(piperidine-3-yloxy)-7-methoxy-chinazoline, 4-[(3-chloro-4-fluoro-phenyl)amino]-6-[1-(2-acetylamino-ethyl)-piperidin-4-yloxy]-7-methoxy-chinazoline, 4-[(3-chloro-4-fluoro-phenyl)amino]-6-(tetrahydropyran-4-yloxy)-7-ethoxy-chinazoline, 4-[(3-chloro-4-fluoro-phenyl)amino]-6-{trans-4-[(morpholin-4-yl)carbonylamino]-cyclohexan-1-yloxy}-7-methoxy-chinazoline, 4-[(3-chloro-4-fluoro-phenyl)amino]-6-{1-[(piperidin-1-yl)carbonyl]-piperidin-4-yloxy}-7-methoxy-chinazoline, 4-[(3-chloro-4-fluoro-phenyl)amino]-6-(cis-4-{N-[(morpholin-4-yl)carbonyl]-N-methyl-amino}-cyclohexan-1-yloxy)-7-methoxy-chinazoline, 4-[(3-4-fluoro-phenyl)amino]-6-(trans-4-ethansulfonylamino-cyclohexan-1-yloxy)-7-methoxy-chinazoline, 4-[(3-chloro-4-fluoro-phenyl)amino]-6-(1-methanesulfonyl-piperidin-4-yloxy)-7-(2-methoxy-ethoxy)-chinazoline, 4-[(3-chloro-4-fluoro-phenyl)amino]-6-[1-(2-methoxy-acetyl)-piperidin-4-yloxy]-7-(2-methoxy-ethoxy)-chinazoline, 4-[(3-ethinyl-phenyl)amino]-6-(tetrahydropyran-4-yloxy]-7-methoxy-chinazoline, 4-[(3-chloro-4-fluoro-phenyl)amino]-6-(cis-4-{N-[(piperidin-1-yl)carbonyl]-N-methyl-amino}cyclohexan-1-yloxy)-7-methoxy-chinazoline, 4-[(3-chloro-4-fluoro-phenyl)amino]-6-{cis-4-[(morpholin-4-yl)carbonylamino]-cyclohexan-1-yloxy}-7-methoxy-chinazoline, 4-[(3-chloro-4-fluoro-phenyl)amino]-6-{1-[2-(2-oxopyrrolidin-1-yl)ethyl]-piperidin-4-yloxy}-7-methoxy-chinazoline, 4-[(3-ethinyl-phenyl)amino]-6-(1-acetyl-piperidin-4-yloxy)-7-methoxy-chinazoline, 4-[(3-ethinyl-phenyl)amino]-6-(1-methyl-piperidin-4-yloxy)-7-methoxy-chinazoline, 4-[(3-ethinyl-phenyl)amino]-6-(1-methanesulfonyl-piperidin-4-yloxy)-7-methoxy-chinazolin, 4-[(3-chloro-4-fluoro-phenyl)amino]-6-(1-methyl-piperidin-4-yloxy)-7(2-methoxy-ethoxy)-chinazoline, 4-[(3-ethinyl-phenyl)amino]-6-{1-[(morpholin-4-yl)carbonyl]-piperidin-4-yloxy}-7-methoxy-chinazoline, 4-[(3-chloro-4-fluoro-phenyl)amino]-6-{1-[(N-methyl-N-2-methoxyethyl-amino)carbonyl]-piperidin-4-yloxy}-7-methoxy-chinazoline, 4-[(3-chloro-4-fluoro-phenyl)amino]-6-(1-ethyl-piperidin-4-yloxy)-7-methoxy-chinazoline, 4-[(3-chloro-4-fluoro-phenyl)amino]-6-[cis-4-(N-methanesulfonyl-N-methyl-amino)-cyclohexan-1-yloxy]-7-methoxy-chinazoline, 4-[(3-chloro-4-fluoro-phenyl)amino]-6-[cis-4-(N-acetyl-N-methyl-amino)-cyclohexan-1-yloxy]-7-methoxy-chinazoline, 4-[(3-chloro-4-fluoro-phenyl)amino]-6-(trans-4-methylamino-cyclohexan-1-yloxy)-7-methoxy-chinazoline, 4-[(3-chloro-4-fluoro-phenyl)amino]-6-[trans-4-(N-methansulfonyl-N-methyl-amino)-cyclohexan-1-yloxy]-7-methoxy-chinazoline, 4-[(3-chloro-4-fluoro-phenyl)amino]-6-(trans-4-dimethylamino-cyclohexan-1-yloxy)-7-methoxy-chinazoline, 4-[(3-chloro-4-fluoro-phenyl)amino]-6-(trans-4-{N-[(morpholin-4-yl)carbonyl]-N-methyl-amino}-cyclohexan-1-yloxy)-7-methoxy-chinazoline, 4-[(3-chloro-4-fluoro-phenyl)amino]-6-[2-2,2-dimethyl-6-oxo-morpholin-4-yl)-ethoxy]-7-[(S)-(tetrahydrofuran-2-yl)methoxy]-chinazoline, 4-[(3-chloro- 4-fluoro-phenyl)amino]-6-(1-methansulfonyl-piperidin-4-yloxy)-7-methoxy-chinazoline, 4-[(3-chlor-4-fluoro-phenyl)amino]-6-(1-cyano-piperidin-4-yloxy)-7-methoxy-chinazoline, and 4-[(3-chloro-4-fluoro-phenyl)amino]-6-{1-[(2-methoxyethyl)carbonyl]-piperidin-4-yloxy}-7-methoxy-chinazoline, optionally in the form of the racemates, the enantiomers, the diastereomers and optionally the pharmacologically acceptable acid addition salts, solvates and/or the hydrates thereof.

The pharmacologically acceptable acid addition salts could be from the group of hydrochloride, hydrobromide, hydroiodide, hydrosulfate, hydrophosphate, hydromethansulfonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluolsulfonate, preferably hydrochloride, hydrobromide, hydrosulfate, hydrophosphate, hydrofumarate and hydromethansulfonate.

Moreover, the compound could be from the group of antiallergika, derivates of ergotalcaloids, triptane, CGRP-antagonists, phosphodiesterase-V-inhibitors, optionally in the form of the racemates, the enantiomers, the diastereomers and optionally the pharmacologically acceptable acid addition salts and the hydrates thereof.

As antiallergika: disodiumcromoglicate, nedocromil.

As derivates of alkaloides: dihydroergotamine, ergotamine.

Moreover, inhalable macromolecules can be used as pharmacologically active substances, as disclosed in EP 1 003 478.

For inhalation purposes pharmaceuticals, formulations and mixtures of pharmaceuticals with the above named pharmacologically active substances can be used, as well as their pharmacologically active salts, esters and combinations of the pharmacologically active substances, salts and esters.

What is claimed is:

1. Atomizer for a fluid, comprising:
   a container with a fluid,
   at least one counter device for counting at least one of the operations of the atomizer and the number of containers inserted, and
   a housing part formed of a plurality of housing parts, one of which is detachable from the atomizer for at least one inserting and exchanging the container,
   a pressure generator for pressurizing the fluid from the container which is separate from the container and is mounted in one of the housing parts,
   wherein the at least one counter device comprises at least a first counter for counting the operations of the atomizer, the first counter being arranged on one of the housing parts, the first counter being adapted to lock the atomizer against further operation of the current container if a certain number of operations of the atomizer is reached or exceeded in a first locked state, and
   wherein the first counter is only exchangeable or replaceable with the container to which it is permanently connected thereto.

2. Atomizer for a fluid, comprising:
   a container with a fluid,
   a pressurizer for pressurizing of the fluid that is separate from the container,
   a counter device for counting operations of the atomizer, and
   a housing part detachable from the atomizer for at least one inserting and exchanging the container,
   wherein the counter device comprises a first counter for counting the operations of the atomizer, the first counter being adapted to lock the atomizer against further operation of the current container if a certain number of operations of the atomizer is reached or exceeded in a first locked state, and
   wherein the counter device is adapted to lock the atomizer against further operation if a certain number of containers have been used or a certain number of total operations of the atomizer with the current container has been reached or exceeded in a second locked state,
   wherein the counter device is mechanically driven by tensioning of the pressurizer, and
   wherein the first counter is only exchangeable or replaceable with the container to which it is permanently connected thereto.

3. Atomizer according to claim 2, wherein a locking element of the atomizer necessary for at least one delivery and atomization of fluid is locked in one of the first and the second locked states.

4. Atomizer according to claim 2, wherein at least one counter device is constructed and arranged to register each tensioning of the pressurizer and to count the tensioning as an operation of the atomizer.

5. Atomizer according to claim 2, wherein tensioning of at least one of the pressurizer and a drive spring for the pressurizer is locked in one of the first and second locked state.

6. Atomizer according to claim 2, wherein the housing part is rotatable for at least one of extraction, fluid delivery, pressurization and atomization of the fluid, and wherein the housing part is locked against rotation in one of the first and second locked states.

7. Atomizer according to claim 2, wherein the first locked state is resettable by detaching the housing part and changing the container.

8. Atomizer according to claim 2, wherein the housing part is secured against detachment from the atomizer in the second locked state.

9. Atomizer according to claim 2, wherein the counter device is a purely mechanically operating device.

10. Atomizer according to claim 2, wherein the counter device has a display device for displaying at least one of the number of operations already performed or still possible by the atomizer and the number of containers inserted or that can still be inserted in the atomizer.

11. Atomizer according to claim 2, wherein the housing part is rotatable in one direction of rotation for at least one of tensioning of a pressurizing drive spring and for delivering fluid.

12. Atomizer according to claim 2, wherein the pressurizer is provided with a drive spring, the drive spring being operable for producing a force for causing atomization of the fluid.

13. Atomizer for a fluid, comprising:
    a container with a fluid,
    at least one counter device for counting at least one of the operations of the atomizer and the number of containers inserted, and
    a housing part detachable from the atomizer for at least one inserting and exchanging the container,
    wherein the at least one counter device comprises at least a first counter for counting the operations of the atomizer arranged on the housing part, the first counter being adapted to lock the atomizer against at least one of further operation and removal of the current container or insertion of a new container if a certain number of operations of the atomizer is reached or exceeded in a first locked state, wherein the counter device comprises a second counter adapted to lock the atomizer against further operation if a certain number of containers have been used, wherein the first and second counters are drivingly coupled, and wherein the first counter is only exchangeable or replaceable with the container to which it is permanently connected thereto.

14. Atomizer according to claim 13, further comprising a pressure generator for pressurizing the fluid in the container which is separate from the container.

15. Atomizer according to claim 13, wherein the fluid is a liquid in an unpressurized state.

16. Atomizer according to claim 13, wherein in one of the first and the second locked states, a locking element of the atomizer necessary for at least one delivery and atomization of fluid is locked.

17. Atomizer according to claim 13, further comprising at least one of a pressurizer and a drive spring, wherein tensioning of the at least one of the pressurizer and the drive spring is locked in one of the first and second locked state.

18. Atomizer according to claim 13 wherein the housing part is rotatable for at least one of extraction, fluid delivery, pressurization and atomization of the fluid, and wherein the housing part is locked against rotation in one of the first and second locked states.

19. Atomizer according to claim 13, wherein the first locked state is resettable by detaching the housing part and changing the container.

20. Atomizer according to claim 13, wherein the housing part is secured against detachment from the atomizer in the second locked state.

21. Atomizer according to claim 13, wherein the container is adapted to perform an axial movement during at least one of fluid extraction, fluid delivery, pressurization and atomization, and wherein the counter device registers said movement of the container or an end position of said movement and counts the registering thereof as an operation of the atomizer.

22. Atomizer according to claim 21, wherein an operating element for the counter is provided on the container, the counter device registering the movement or a position of the container by interaction with the operating element.

23. Atomizer according to claim 22, wherein the operating element is rotatably mounted on the container.

24. Atomizer according to claim 22, wherein the operating element has an arm-shaped section which interacts with at least one counting ring of the counter device so that, when the container moves, the counting ring is rotated by an increment or counter step.

25. Atomizer according to claim 22, wherein the counter device is operable to cause the atomizer to be locked against at least one of further operation and removal of the current container or insertion of a new container, when at least one of a certain number of operations of the atomizer have been performed and a certain number of containers has been inserted.

26. Atomizer according to claim 21, wherein the counter device registers the reaching or passing of an end position of the container, an end position of the tensioned atomizer, or a movement of the container when tensioning or releasing the atomizer or a drive spring and counts the registering thereof as an operation of the atomizer.

27. Atomizer according to claim 21, wherein the counter device is adapted to register the movement of the container in a contact-free manner.

28. Atomizer according to claim 13, wherein the counter device is a purely mechanically operating device.

29. Atomizer according to claim 13, wherein the counter device is adapted to register an action from among each extraction of fluid from the container, each tensioning of a drive spring of a pressurizer of the atomizer and each atomization and to count the registering thereof as an operation of the atomizer.

30. Atomizer according to claim 13, the counter device is adapted to count the number of operations performed by the atomizer or that can still be performed with the current container.

31. Atomizer according to claim 30, wherein the counter is resettable when the container is changed, and wherein the resetting is locked in the assembled state of the atomizer.

32. Atomizer according to claim 13, wherein the counter device is adapted to count and display the total number of all operations of the atomizer that have been performed or are still possible with more than one container.

33. Atomizer according to claim 13, wherein the counter device has a display device for displaying at least one of the number of operations already performed or still possible by the atomizer and the number of containers inserted or that can still be inserted in the atomizer.

34. Atomizer according to claim 13, wherein the housing part is rotatable in one direction of rotation for at least one of tensioning of a pressurizing drive spring and for delivering fluid.

35. Atomizer according to claim 13, further comprising a pressurizer with a drive spring, the drive spring being operable for producing a force for causing atomization of the fluid.

36. Atomizer according to claim 13, wherein the first and second counters are separable from each other for changing of the container.

37. Atomizer according to claim 36, wherein the first counter is exchangeable when changing the container.

38. Atomizer according to claim 13, wherein at least the first counter is connected in a non-detachable manner to the housing part.

39. Atomizer according to claim 38, wherein the first counter is arranged in an axial front end area of the housing part.

40. Atomizer according to claim 38, wherein the first counter surrounds the container in a circular fashion.

41. Atomizer according to claim 13, wherein the housing part along with the container and the first counter form an exchangeable unit.

42. Atomizer according to claim 13, further comprising a housing upper part to which said housing part is detachably connectable and wherein the second counter is rotatably connected with the housing upper part in a undetachable manner.

43. Atomizer according to claim 35, further comprising a movable or rotatable inner part for tensioning said drive spring.

44. Atomizer according to claim 43, wherein the second counter is arranged on said inner part.

45. Atomizer according to claim 43, wherein the counter device comprises a threaded spindle with a rider, the threaded spindle being rotated by a rotation of said inner part.

46. Atomizer according to claim 45, wherein the rider is operable as a blocking element in one of the first and second locked states, so that rotation of the inner part is blocked.

47. Atomizer according to claim 35, further comprising a locking device for locking a locking element, the locking device being operable for releasing the locking element to trigger delivery of the fluid.

48. Atomizer according to claim 47, further comprising a movable or rotatable inner part for tensioning said drive spring and wherein the locking device is arranged on said inner part.

49. Atomizer according to claim 48, wherein, in at least one of the first and second locked state, at least one of rotation of the inner part and operation of the locking element is blocked.

50. Atomizer according to claim 47, wherein the locking device has a lock part which is movable parallel to a longitudinal axis of the atomizer, said lock part, in a locked state, blocking operation of the atomizer.

51. Atomizer according to claim 50, further comprising a housing upper part to which said housing part is detachably connectable, wherein the lock part, in the locked state, engages between the locking element and the housing upper part.

52. Atomizer according to claim 50, wherein the locking device has a control part that is peripherally movable in relation to the longitudinal axis of the atomizer for operation of the lock part.

53. Atomizer according to claim 45, further comprising a locking device for locking a locking element, the locking device being operable for releasing the locking element to trigger delivery of the fluid; wherein the locking device has a lock part which is movable parallel to a longitudinal axis of the atomizer, said lock part, in a locked state, blocking operation of the atomizer, wherein the locking device has a control part that is peripherally movable in relation to the longitudinal axis of the atomizer for operation of the lock part, and wherein the control part is operably moved by the rider to block operation of the atomizer.

54. Atomizer according to claim 53, wherein the control part, during operation of the atomizer, is peripherally movable for operation of the lock part.

55. Atomizer according to claim 13, wherein at least one of the first and second locked states is irreversable.

56. Atomizer according to claim 13, further comprising a purely mechanical means for atomization of the liquid.

57. Atomizer according to claim 13, wherein the atomizer is a portable inhaler for medicinal aerosol therapy.

* * * * *